(12) United States Patent
Johnson et al.

(10) Patent No.: US 6,972,286 B2
(45) Date of Patent: Dec. 6, 2005

(54) OXAZOLIDINONES HAVING A BENZANNULATED 6- OR 7-MEMBERED HETEROCYCLE

(75) Inventors: Paul D. Johnson, Kalamazoo, MI (US); Paul Adrian Aristoff, Kalamazoo, MI (US); Toni-Jo Poel, Wayland, MI (US); Lisa Marie Thomasco, Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/992,660

(22) Filed: Nov. 14, 2001

(65) Prior Publication Data

US 2002/0133021 A1 Sep. 19, 2002

Related U.S. Application Data

(60) Provisional application No. 60/249,550, filed on Nov. 17, 2000.

(51) Int. Cl.[7] .................... G07D 223/16; A61K 31/55
(52) U.S. Cl. ......................................... 514/221; 540/593
(58) Field of Search .......................... 540/593; 514/221

(56) References Cited

U.S. PATENT DOCUMENTS

| | | | |
|---|---|---|---|
| 5,032,605 A | 7/1991 | Wang et al. | 514/376 |
| 5,036,092 A | 7/1991 | Wang et al. | 514/376 |
| 5,036,093 A | 7/1991 | Wang et al. | 514/376 |
| 5,039,690 A | 8/1991 | Wang et al. | 514/376 |
| 5,164,510 A | 11/1992 | Brickner | 548/231 |

FOREIGN PATENT DOCUMENTS

| | | | |
|---|---|---|---|
| DE | 19802239 | 7/1999 | C07D/417/04 |
| EP | 359418 | 8/1989 | C07D/413/04 |
| EP | 113016 | 11/1999 | C07D/263/22 |
| WO | WO 96/05194 | 2/1996 | C07D/403/04 |
| WO | WO98/54161 | 12/1998 | C07D/263/20 |
| WO | WO 99/64416 | 12/1999 | C07D/413/14 |
| WO | WO 99/64417 | 12/1999 | C07D/413/14 |
| WO | WO 00/10566 | 3/2000 | A61K/31/42 |
| WO | WO 00/21960 | 4/2000 | C07D/413/14 |
| WO | WO 00/73301 | 12/2000 | C07D/413/04 |

OTHER PUBLICATIONS

M. Carmack, "The Willgerodt–Kindler Reactions. 7. The Mechanisms," J. Heterocyclic Chem., 26:1319–1323 [1989];.

B. Pecherer; Sunbury, R.C.; and A. Brossi, "The Synthesis of Some 7- and 7,8–Substituted 2,3,4, 5–Tetrahydro–1H–3–benzazepines," J. Heterocyclic Chem. 779–783 [1971];.

J. David Margerum; and C.T. Petrusis, "The Photodecarboxylation of Nitrophenylacetate Ions," J. Amer. Chem. Society 91:2467–2472 [1969];.

"Thallium in Organic Synthesis. XXVII. A Simple One–Step Conversion of Acetophenones into Methyl Phenylacetates Using Thallium (III) Nitrate (TTN)," J. Amer. Chem. Society 93:4919–4920 [1971];.

G.J. Quallich; Makowski, T.W.; Sanders, A.F.; Urban, F.J.; and E. Vazquez, "Synthesis of 1,2,3,4–Tetrahydroisoquinolines Containing Electron–Withdrawing Groups," J. Org. Chem. 63:4116–4119 [1998];.

S.E. Schaus; and E.N. Jacobsen, "Dynamic Kinetic Resolution of Epichlorohydrin via Enantioselective Catalytic Ring Opening with TMSN$_3$. Practical Synthesis of Aryl Oxazolidinone Antibacterial Agents," Tetrahedron Letters 37(44):7937–7940 [1996].

*Primary Examiner*—Kamal A. Saeed
(74) *Attorney, Agent, or Firm*—John H. Engelmann; Lucy X. Yang

(57) ABSTRACT

The present invention provides oxazolidinones having a benzannelated 6- or 7-membered heterocycle as antibacterial agents.

21 Claims, No Drawings

OXAZOLIDINONES HAVING A BENZANNULATED 6- OR 7-MEMBERED HETEROCYCLE

CROSS REFERENCE TO RELATED APPLICATION

This application claims the benefit of the following provisional application: U.S. Ser. No. 60/249550, filed Nov. 17, 2000, under 35 USC 119(e)(i), and is incorporated herein by reference in its entirety.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, gram-negative aerobic bacteria such as *H. influenzae* and *M. catarrhalis*, as well as anaerobic organisms such as bacteroides and clostridia species, and acid-fast organisms such as *Mycobacterium tuberculosis* and *Mycobacterium avium*.

The present invention relates to benzazepine, tetrahydroisoquinoline, tetrahydroisochroman, tetrahydroisothiochroman, and benzothiepin oxazolidinones, their use as antibacterials, and their preparation.

INFORMATION DISCLOSURE

U.S. Pat. No. 5,164,510 discloses indoline oxazolidinones useful as antibacterial agents.

PCT patent application US00/08224 discloses tetrahydroquinoline oxazolidinones useful as antibacterial agents.

PCT publications, WO 99/64416, WO91/64417, and WO 00/21960 disclose oxazolidinone derivatives useful as antibacterial agents.

PCT publication, WO 00/10566 discloses isoxazolinones useful as antibacterial agents.

SUMMARY OF THE INVENTION

The present invention provides a compound of formula I

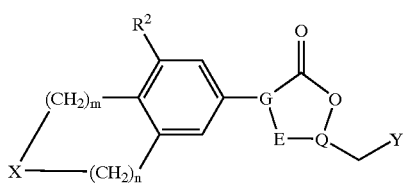

or a pharmaceutically acceptable salt thereof wherein
Y is
  a) —NHC(=W)R$^1$,
  b) —O-het, —S-het, or —NH-het;
X is
  a) —O—,
  b) —NR$^3$—,
  c) —S(=O)$_i$—, or
  d) —S(=O)(=NR$^4$)—;
W is
  a) O, or
  b) S;
R$^1$ is
  a) H,
  b) C$_{1-8}$alkyl,
  c) C$_{3-6}$cycloalkyl,
  d) OC$_{1-4}$alkyl,
  e) SC$_{1-4}$alkyl,
  f) NH$_2$,
  g) NHC$_{1-6}$alkyl, or
  h) N(C$_{1-6}$alkyl)$_2$;
R$^2$ is
  a) H,
  b) halo, or
  c) C$_{1-4}$alkyl;
R$^3$ is
  a) H,
  b) C$_{1-8}$alkyl,
  c) aryl,
  d) het,
  e) C(=W)R$^5$,
  f) C(=O)OR$^6$, or
  g) S(=O)$_i$R$^7$;
R$^4$ is
  a) H, or
  b) C$_{1-8}$alkyl;
R$^5$ is
  a) H,
  b) aryl,
  c) het,
  d) NR$^8$R$^9$, or
  e) C$_{1-8}$alkyl;
R$^6$ is
  a) C$_{1-8}$alkyl,
  b) aryl, or
  c) het;
R$^7$ is
  a) aryl,
  b) het,
  c) NR$^8$R$^9$, or
  d) C$_{1-8}$alkyl;
R$^8$ and R$^9$ are independently
  a) H,
  b) C$_{1-8}$alkyl, or
  c) aryl;
wherein >G-E- is >N—C— and Q is a carbon atom, or >G-E is >C=C— and Q is a nitrogen atom; (wherein > represents two single bonds) aryl is a phenyl radical or an ortho-fused bicyclic carbocyclic radical wherein at least one ring is aromatic;
het is a C-linked five- (5) or six- (6) membered saturated or unsaturated heterocyclic ring having 1, 2, or 3 heteroatoms selected from the group consisting of oxygen, sulfur, and nitrogen, which is optionally fused to a benzene ring;
at each occurrence, alkyl or cycloalkyl is optionally substituted with one or more OR$^8$, halo, aryl, S(=O)$_i$R$^7$, C(=W)R$^8$, OC(=O)C$_{1-6}$alkyl, or NR$^8$R$^9$;
at each occurrence, aryl is optionally substituted with one or more halo, OH, CF$_3$, OC$_{1-6}$alkyl, CN, C$_{1-6}$alkyl, S(=O)$_i$R$^7$, C(=W)R$^8$, OC(=O)R$^8$, NHC(=O)R$^8$, or NR$^8$R$^9$;
at each occurrence, het is optionally substituted with one or more halo, OH, CF$_3$, OC$_{1-6}$alkyl, CN, C$_{1-6}$alkyl, S(=O)$_i$R$^7$, C(=W)R$^8$, OC(=O)R$^8$, NHC(=O)R$^8$, or NR$^8$R$^9$, oxo, or oxime;

m is 0, 1, 2, 3, or 4;

n is 0, 1, 2, 3, or 4; with the proviso that m and n taken together are 3 or 4; and i is 0, 1, or 2.

In another aspect, the present invention also provides:

a pharmaceutical composition comprising a compound of formula I or a pharmaceutically acceptable salt thereof and a pharmaceutically acceptable carrier, or a method for treating microbial infections in humans or other warm-blooded animals by administering to the subject in need a therapeutically effective amount of a compound of formula I or a pharmaceutically acceptable salt thereof The invention also provides some novel intermediates and processes that are useful for preparing compounds of formula I.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Specific and preferred values listed below for radicals, substituents, and ranges are for illustration only; they do not exclude other defined values or other values within defined ranges for the radicals and substituents.

The following definitions are used, unless otherwise described.

Alkyl denotes both straight and branched groups; but reference to an individual radical such as "propyl" embraces only the straight chain radical, a branched chain isomer such as "isopropyl" being, specifically referred to. Specifically, $C_{1-8}$alkyl can be methyl, ethyl, propyl, isopropyl, butyl, iso-butyl, sec-butyl, pentyl, 3-pentyl, hexyl, heptyl, octyl and their isomeric forms thereof. Specifically, $C_{1-4}$alkyl can be methyl, ethyl, propyl, isopropyl, butyl, iso-butyl, sec-butyl, and their isomeric forms thereof.

At each occurrence, alkyl may be substituted with one or more group as defined in the summary of the invention or in claims.

$C_{3-6}$ cycloalkyl denotes a cycloalkyl having three to six carbon atoms. Specifically, $C_{3-6}$ cycloalkyl can be cyclopropyl, cyclobutyl, cyclopentyl, or cyclohexyl.

The term "halo" refers to fluoro (F), chloro (Cl), bromo (Br), or iodo (I).

The term "aryl" refers to a phenyl radical or an ortho-fused bicyclic carbocyclic radical wherein at least one ring is aromatic. At each occurrence, aryl may be substituted with one or more group as defined in the summary of the invention or in claims. A specific value for aryl is phenyl.

The term "het" refers to a five- (5) or six- (6) membered saturated or unsaturated heterocyclic ring having 1, 2, or 3 heteroatoms selected from the group consisting of oxygen, sulfur, and nitrogen, which is optionally fused to a benzene ring.

Examples of unsaturated "het" include pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrizinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

Examples of saturated "het" include piperdinyl, piperazinyl, morpholinyl, thiomorpholinyl, azetidinyl, pyrrolidinyl, hydantoin, oxathiolane, oxazolidine, dioxolane, or imidazolidine.

At each occurrence, het may be substituted with one or more group as defined in the summary of the invention or in claims.

A specific value for het is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

Mammal denotes human and other warm blooded animals.

Pharmaceutically acceptable salts denotes those salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, methanesulfonic acid salt and etc.

Compounds of the present invention may be in a form of pharmaceutically acceptable salts.

It is to be understood that the present invention encompasses any racemic, optically-active, polymorphic, tautomeric, or stereoisomeric form, or mixture thereof.

A specific value for $R^2$ is H.

A specific value for $R^2$ is F.

A specific value for $R^1$ is $C_{1-6}$alkyl.

A specific value for $R^1$ is methyl.

A specific value for X is $NR^3$.

A specific value for $R^3$ is $C(=O)R^5$.

A specific value for $R^3$ is $C(=O)H$.

A specific value for $R^3$ is $C(=O)CH_2OH$.

A specific value for $R^5$ is $C_{1-4}$alkyl, optionally substituted with $C(=O)C_{1-4}$alkyl, $OC(=O)C_{1-4}$alkyl, $C(=O)$phenyl, or phenyl, wherein said phenyl is optionally substituted with an iodo atom, or $CF_3$.

A specific value for $R^5$ is phenyl.

A specific value for $R^3$ is $C(=O)OR^6$.

A specific value for $R^6$ is $C_{1-4}$alkyl.

A specific value for $R^3$ is $C(=S)R^5$, wherein $R^5$ is phenyl, alkyl or $NR^8R^9$, wherein $R^8$ and $R^9$ are independently H, $C_{1-4}$alkyl or aryl.

A specific value for $R^3$ is $S(=O)_tC_{1-4}$alkyl,

A specific value for $R^3$ is H, alkyl, or aryl.

A specific value is wherein m is 1 and n is 3.

A specific value is wherein wherein m is 2 and n is 2.

A specific value is wherein wherein m is 0 and n is 4.

A specific value is wherein wherein m is 1 and n is 2.

A specific value is wherein wherein m is 2 and n is 1.

A specific value is wherein m is 0 and n is 3

A specific value is wherein m and n taken together are 3.

A specific value is wherein m and n taken together are 4.

A specific value for W is O.

A specific value for W is S.

A specific value for X is S, SO or $SO_2$.

A specific value for X is O.

A specific compound of the present invention is a compound of formula IA:

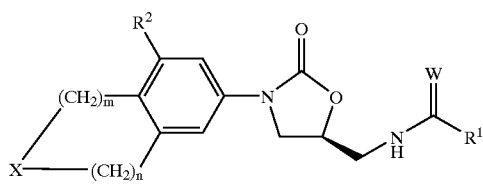

IA wherein X, W, $R^1$ and $R^2$ are as defined above.

Another specific compound of the present invention is a compound of formula IB:

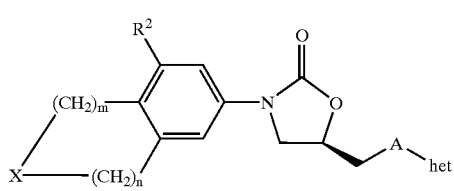

IB wherein A is O, S or NH and het is as defined above, preferably isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

Another specific compound of the present invention is a compound of formula IC:

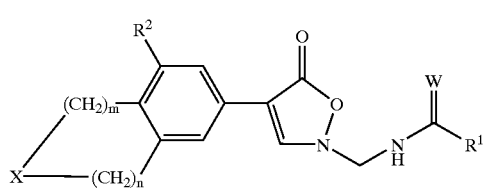

IC wherein X, W, $R^1$ and $R^2$ are as defined above.

Another specific compound of the present invention is a compound of formula ID:

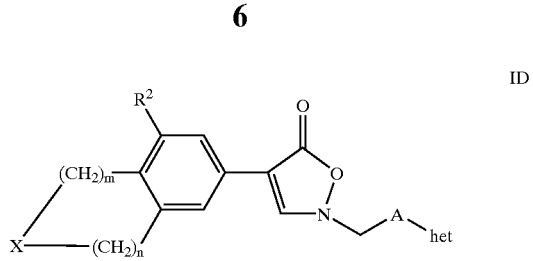

ID wherein A is O, S or NH and het is as defined above, preferably isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

Examples of the present invention include:
a) (−)-methyl 6-[(5S)-5-[(acetylamino)methyl]-2-oxo-3-oxazolidinyl]-3,4-dihydro-2(1H)-isoquinolinecarboxylate,
b) (−)-N-[[(5S)-3-[2-formyl-1,2,3,4-tetrahydro-6-isoquinolinyl]-2-oxo-5-oxazolidinyl]methyl]acetamide,
c) (−)-N-[[(5S)-3-[2-[(acetyloxy)acetyl]-1,2,3,4-tetrahydro-6-isoquinolinyl]-2-oxo-5-oxazolidinyl]methyl]acetamide,
d) (−)-N-[[(5S)-3-[2-[(hydroxy)acetyl]-1,2,3,4-tetrahydro-6-isoquinolinyl]-2-oxo-5-oxazolidinyl]methyl]acetamide,
e) (+)-methyl 6-[(5S)-5-[(ethanethioylamino)methyl]-2-oxo-3-oxazolidinyl]-3,4-dihydro-2(1H)-isoquinolinecarboxylate,
f) (+)-N-[[(5S)-3-[2-formyl-1,2,3,4-tetrahydro-6-isoquinolinyl]-2-oxo-5-oxazolidinyl]methyl]ethanethioamide, or
g) (+)-N-[[(5S)-3-[2-[(hydroxy)acetyl]-1,2,3,4-tetrahydro-6-isoquinolinyl]-2-oxo-5-oxazolidinyl]methyl]ethanethioamide.

Examples of the present invention further include:
a) (+)-N-[[(5S)-3-[2-formyl-1,2,3,4-tetrahydro-7-isoquinolinyl]-2-oxo-5-oxazolidinyl]methyl]ethanethioamide, or
b) (+)-N-[[(5S)-3-[2-[(hydroxy)acetyl]-1,2,3,4-tetrahydro-7-isoquinolinyl]-2-oxo-5-oxazolidinyl]methyl]ethanethioamide.

Examples of the present invention further include:
a) (−)-N-[[(5S)-3-(3,4-dihydro-1H-2-benzopyran-6-yl)-2-oxo-5-oxazolidinyl]methyl]acetamide,
b) (+)-N-[[(5S)-3-(3,4-dihydro-1H-2-benzopyran-6-yl)-2-oxo-5-oxazolidinyl]methyl]ethanethioamide,
c) (−)-N-[[(5S)-3-(3,4-dihydro-1H-2-benzothiopyran-6-yl)-2-oxo-5-oxazolidinyl]methyl]acetamide,
d) (+)-N-[[(5S)-3-(3,4-dihydro-1H-2-benzothiopyran-6-yl)-2-oxo-5-oxazolidinyl]methyl]ethanethioamide, or
e) (+)-N-[[(5S)-3-(3,4-dihydro-2,2-dioxido-1H-2-benzothiopyran-6-yl)-2-oxo-5-oxazolidinyl]methyl]ethanethioamide.

Examples of the present invention further include:
a) (+)-N-[[(5S)-3-(3,4-dihydro-1H-2-benzopyran-7-yl)-2-oxo-5-oxazolidinyl]methyl]ethanethioamide,
b) (−)-N-[[(5S)-3-(3,4-dihydro-1H-2-benzopyran-7-yl)-2-oxo-5-oxazolidinyl]methyl]acetamide,
c) (+)-N-[[(5S)-3-(3,4-dihydro-1H-2-benzopyran-7-yl)-2-oxo-5-oxazolidinyl]methyl]ethanethioamide,
d) (+)-N-[[(5S)-3-(3,4-dihydro-2,2-dioxido-1H-2-benzothiopyran-7-yl)-2-oxo-5-oxazolidinyl]methyl]ethanethioamide, or
e) N-[[(5S)-3-(3,4-dihydro-2-oxido-1H-2-benzothiopyran-7-yl)-2-oxo-5-oxazolidinyl]methyl]acetamide.

Examples of the present invention further include:
a) N-{[(5S)-3-(3-formyl-1,2,4,5-tetrahydro-1H-3-benzazepin-7-yl)-2-oxo-1,3-oxazolidin-5-yl]methyl}acetamide, b) N-{[(5S)-3-(3-glycoloyl-1,2,4,5-tetrahydro-1H-3-benzazepin-7-yl)-2-oxo-1,3-oxazolidin-5-yl]methyl}acetamide, c) benzyl 7-{(5S)-5-[(acetylamino)methyl]-2-oxo-1,3-oxazolidin-3-yl}-1,2,4,5-tetrahydro-3H-3-benzazepine-3-carboxylate, d) N-{[(5S)-3-(3-glycoloyl-1,2,4,5-tetrahydro-1H-3-benzazepin-7-yl)-2-oxo-1,3-oxazolidin-5-yl]methyl}ethanethioamide, e) N-{[(5S)-3-(3-acetyl-1,2,4,5-tetrahydro-1H-3-benzazepin-7-yl)-2-oxo-1,3-oxazolidin-5-yl]methyl}acetamide, f) methyl 7-{(5S)-5-[(acetylamino)methyl]-2-oxo-1,3-oxazolidin-3-yl}-1,2,4,5-tetrahydro-3H-3-benzazepine-3-carboxylate, g) N-{[(5S)-3-(3-benzoyl-1,2,4,5-tetrahydro-1H-3-benzazepin-7-yl)-2-oxo-1,3-oxazolidin-5-yl]methyl}acetamide, h) N-({(5S)-3-[3-(5-amino-1,3,4-thiadiazol-2-yl)-1,2,4,5-tetrahydro-1H-3-benzazepin-7-yl]-2-oxo-1,3-oxazolidin-5-yl}methyl)acetamide i) N-({(5S)-3-[3-(methylsulfonyl)-1,2,4,5-tetrahydro-1H-3-benzazepin-7-yl]-2-oxo-1,3-oxazolidin-5-yl}methyl)acetamide, j) N-({(5S)-3-[3-(5-methylthio-1,3,4-thiadiazol-2-yl)-1,2,4,5-tetrahydro-1H-3-benzazepin-7-yl]-2-oxo-1,3-oxazolidin-5-yl}methyl)acetamide, k) N-({(5S)-3-[3-(5-methyl-1,3,4-thiadiazol-2-yl)-1,2,4,5-tetrahydro-1H-3-benzazepin-7-yl]-2-oxo-1,3-oxazolidin-5-yl}methyl)acetamide, l) phenyl 7-{(5S)-5-[(acetylamino)methyl]-2-oxo-1,3-oxazolidin-3-yl}-1,2,4,5-tetrahydro-3H-3-benzazepine-3-carboxylate, m) N-[((5S)-3-{3-(phenyl)acetyl-1,2,4,5-tetrahydro-1H-3-benzazepin-7-yl}-2-oxo-1,3-oxazolidin-5-yl)methyl]acetamide, n) N-[((5S)-3-{3-[5-(formylamino)-1,3,4-thiadiazol-2-yl]-1,2,4,5-tetrahydro-1H-3-benzazepin-7-yl}-2-oxo-1,3-oxazolidin-5-yl)methyl]acetamide, o) N-[5-(7-{(5S)-5-[(acetylamino)methyl]-2-oxo-1,3-oxazolidin-3-yl}-1,2,4,5-tetrahydro-3H-3-benzazepin-3-yl)-1,3,4-thiadiazol-2-yl]-2-hydroxyacetamide, p) N-[((5S)-3-{3-[(4-iodophenyl)acetyl]-1,2,4,5-tetrahydro-1H-3-benzazepin-7-yl}-2-oxo-1,3-oxazolidin-5-yl)methyl]acetamide, q) N-[((5S)-3-{3-[(3-trifluoromethyl)phenyl)acetyl]-1,2,4,5-tetrahydro-1H-3-benzazepin-7-yl}-2-oxo-1,3-oxazolidin-5-yl)methyl]acetamide, r) 2-(7-{(5S)-5-[(acetylamino)methyl]-2-oxo-1,3-oxazolidin-3-yl}-1,2,4,5-tetrahydro-3H-3-benzazepin-3-yl)-2-oxoethyl 4-[(dimethylamino)methyl]benzoate, s) N-[((5S)-3-{3-[(4-trifluoromethyl)phenyl)acetyl]-1,2,4,5-tetrahydro-1H-3-benzazepin-7-yl}-2-oxo-1,3-oxazolidin-5-yl)methyl]acetamide, t) N-({(5S)-2-oxo-3-[3-(5-oxopentanoyl)-1,2,4,5-tetrahydro-1H-3-benzazepin-7-yl]-1,3-oxazolidin-5-yl}methyl)acetamide, u) N-({(5S)-2-oxo-3-[3-(5-oxohexanoyl)-1,2,4,5-tetrahydro-1H-3-benzazepin-7-yl]-1,3-oxazolidin-5-yl}methyl)acetamide, v) N-{[(5S)-3-(2-formyl-1,3,4,5-tetrahydro-1H-2-benzazepin-7-yl)-2-oxo-1,3-oxazolidin-5-yl]methyl}acetamide, w) N-{[(5S)-3-(2-glycoloyl-1,3,4,5-tetrahydro-1H-2-benzazepin-7-yl)-2-oxo-1,3-oxazolidin-5-yl]methyl}acetamide, x) benzyl 7-{(5S)-5-[(acetylamino)methyl]-2-oxo-1,3-oxazolidin-3-yl}-1,3,4,5-tetrahydro-3H-2-benzazepine-2-carboxylate, y) N-{[(5S)-3-(2-acetyl-1,3,4,5-tetrahydro-1H-2-benzazepin-7-yl)-2-oxo-1,3-oxazolidin-5-yl]methyl}acetamide, z) methyl 7-{(5S)-5-[(acetylamino)methyl]-2-oxo-1,3-oxazolidin-3-yl}-1,3,4,5-tetrahydro-3H-2-benzazepine-2-carboxylate, aa) 7-{(5S)-5-[(acetylamino)methyl]-2-oxo-1,3-oxazolidin-3-yl}-N-phenyl-1,3,4,5-tetrahydro-2H-2-benzazepine-2-carboxamide, bb) N-{[(5S)-3-(1-formyl-2,3,4,5-tetrahydro-1H-1-benzazepin-7-yl)-2-oxo-1,3-oxazolidin-5-yl]methyl}acetamide, or cc) N-{[(5S)-3-(1-formyl-2,3,4,5-tetrahydro-1H-1-benzazepin-7-yl)-2-oxo-1,3-oxazolidin-5-yl]methyl}ethanethioamide.

Examples of the present invention further include:

a) N-[[(5S)-2-oxo-3-(1,2,4,5-tetrahydro-3-benzothiepin-7-yl)-5-oxazolidinyl]methyl]acetamide, b) N-[[(5S)-2-oxo-3-(1,2,4,5-tetrahydro-3,3-dioxido-3-benzothiepin-7-yl)-5-oxazolidinyl]methyl]acetamide, c) N-[[(5S)-2-oxo-3-(1,2,4,5-tetrahydro-3-benzothiepin-7-yl)-5-oxazolidinyl]methyl]ethanethioamide, or d) N-[[(5S)-2-oxo-3-(1,2,4,5-tetrahydro-3,3-dioxido-3-benzothiepin-7-yl)-5-oxazolidinyl]methyl]ethanethioamide.

Schemes A–H describe the preparation of compounds of the present invention. All of the starting materials are prepared by procedures described in these schemes or by procedures that would be well known to one of ordinary skill in organic chemistry. The variables used in the Schemes are as defined below or as in the claims.

Scheme A illustrates the preparation of tetrahydroisoquinoline, A-11. The known diol A-1 ($R_2$ is hydrogen)(*J. Org. Chem.*, 1998, 63, 4116–4119) is converted to the bis-mesylate A-2 upon treatment with methanesulfonyl chloride in the presence of an appropriate base such as triethylamine. Treatment of A-2 with benzylamine in an appropriate solvent such as methylene chloride then provides the ring-closed product, N-benzyl-6-nitrotetrahydroisoquinoline A-3. Simultaneous reduction of the nitro group and removal of the N-benzyl moiety by hydrogenation in the presence of an appropriate catalyst such as palladium-on-carbon in solvents such as methanol, ethanol, tetrahydrofuran or mixtures thereof and subsequent treatment with two equivalents of benzyl chloroformate and an appropriate base such as sodium bicarbonate provides the bis Cbz-protected 6-aminotetrahydroisoquinoline A-4. Structure A-4 can then be converted to A-11 through A-5 and A-6 by methods outlined in Scheme E. Alternatively, the amino methyl oxazolidinone intermediate A-6 can be protected as its Boc derivative A-7 using di-t-butyl dicarbonate and sodium bicarbonate. Then, the Cbz protecting group of A-7 can be removed via hydrogenation in the presence of an appropriate catalyst such as Pearlman's catalyst in a solvent such as methanol, ethanol, ethyl acetate, tetrahydrofuran or mixtures thereof to give the deprotected tetrahydroisoquinoline A-8 which can be acylated by reactions well known to those skilled in the art to give the intermediates A-9. Treatment of A-9 with HCl in a solvent such as methanol or dioxine or mixtures thereof provides the aminomethyl oxazolidinones A-10 as their hydrochloride salts which can then be converted to the acetamide analogs A-11 (W=O) upon treatment with acetic anhydride in the presence of a base such as pyridine or to the thioacetamide analogs A-11 (W=S) upon treatment with ethyl dithioacetate in the presence of a base such as triethylamine.

Scheme B illustrates the preparation of the 2-acyl-1,2,3,4-tetrahydro-7-isoquinoline analogs B-5. The know 4-nitrohomophthalic acid ($R_2$ is hydrogen)(*J. Amer. Chem. Soc.,* 1969, 91, 2467) can be reduced to the diol B-2 according to the method described for the preparation of diol A-1 in Scheme A (*J. Org. Chem.,* 1998, 63, 4116–4119). Diol B-2 can then be converted to the bis Cbz-protected 7-aminotetrahydroisoquinoline B-3 using steps similar to those described in Scheme A for the conversion of A-1 to A-4. Deprotonation of B-3 with a base such as lithium t-butoxide in a suitable solvent such as tetrahydrofuran, dimethylformamide or mixtures thereof in the presence of t-butyl (2S)-3-chloro-2-hydroxypropylcarbamate at a suitable temperature, typically in a range from 0° C. to ambient temperature, then provides the Boc-protected aminomethyloxazolidinone B-4. The remaining steps which lead to the desired compounds B-5 are similar to those described in Scheme A for the conversion of A-7 to A-11.

Scheme C illustrates the preparation of the isochroman-6-yl and isothiochroman-6-yl oxazolidinone analogs. The nitro group of the known isochroman C-1 ($R_2$ is hydrogen) (*J. Org. Chem.,* 1998, 63, 4116–4119) is reduced by hydrogenation in the presence of an appropriate catalyst such as platinum oxide in a solvent such as methanol, ethanol, tetrahydrofuran or mixtures thereof, and the resulting amine can be converted to its Cbz derivative C-2 upon treatment with benzyl chloroformate as described previously. For the corresponding isothiochroman, the bismesylate C-3 can be treated with potassium thioacetate in an appropriate solvent such as dimethylformamide to afford the benzyl thioacetate C-4 which is then S-deacetylated in the presence of ammonia in methanol with concomitant ring closure to give the isothiochroman C-5. In this case, the nitro group is reduced with stannous chloride in refluxing ethanol to afford the amine which is then converted to its Cbz derivative C-6. The carbamates C-7 (X=O, S) can be converted to the desired analogs C-8 using methods similar to those described in Scheme A. Alternatively, they can be deprotonated with a base such as lithium t-butoxide in a suitable solvent such as tetrahydrofuran, hexane, dimethylformamide or mixtures thereof in the presence of (1S)-2-acetylamino-1-(chloromethyl)ethyl acetate (*Tel. Lett.* 1996, 37 (44) pp 7937–7940) at a suitable temperature, typically in a range from 0° C. to ambient temperature, to provide the desired acetylaminomethyl oxazolidinones C-8 (X=O, S; Y=O). Where X is S, the sulfur group can be oxidized with an appropriate oxidizing agent such as sodium periodate in an appropriate solvent such as a mixture of methanol and water or osmium tetroxide and N-methylmorpholine N-oxide in an appropriate solvent such as mixtures of acetone and water to give the corresponding sulfoxide and sulfone. In addition, where X is O, S, or $SO_2$, treatment with Lawesson's reagent in refluxing tetrahydrofuran, dioxane or toluene gives the corresponding thioacetamides (Y=S).

Scheme D illustrates the preparation of the isochroman-7-yl and isothiochroman-7-yl oxazolidinone analogs. Diol D-1 can be converted to the isochroman D-2 using a modified Mitsunobu reaction according to the method described for the preparation of isochroman C-1 in Scheme C (*J. Org. Chem.,* 1998, 63, 4116–4119). Using steps outlined previously in Scheme C, the nitro group of D-2 is then reduced and the amine protected as its Cbz derivative to give D-3. Likewise, the nitro group of diol D-1 can be reduced and the amine protected as its Cbz derivative to give diol D-4. Treatment of this diol with 2–3 equivalents of methanesulfonyl chloride in the presence of a base such as triethylamine provides the bismesylate D-5 which, when treated with excess sodium sulfide in dimethylsulfoxide at a suitable temperature, typically in a range from 20–60° C., affords the isothiochroman D-6. The Cbz-protected 7-aminoisochroman and isothiochroman D-7 (X=O, or S) are then converted to the desired analogs D-8 using methods similar to those described in Scheme C.

Scheme E illustrates the preparation of the benzazepine compounds of the present invention. As shown in Scheme E, the known E-1 (*J. Hetrocyclic Chem.,* 1971, pp 779–783) is treated with benzyl chloroformate (2 equivalents) in acetone and water with sodium bicarbonate to give E-2. The protected benzazepine thus prepared can be converted to the final oxazolidinone analogs as outlined in Scheme E. The carbamate derivatives E-2 can be deprotonated with a lithium base such as n-butyllithium, lithium diisopropylamide (LDA), or lithium bis(trimethylsilyl)amide (LHMDS) in a suitable solvent such as THF, N,N-dimethylformamide (DMF), or mixtures thereof, at a suitable temperature, typically in a range from −78° C. to −40° C. to give a lithiated intermediate which is directly treated with R-(−)-glycidyl butyrate. Warming to room temperature then affords (hydroxymethyl)oxazolidinones E-3. In cases where racemic starting materials are used, E-3 is obtained as a mixture of two enantiomers. In the event that enantiomerically pure intermediates are employed, E-3 is obtained as one enantiomer.

As shown in Scheme E, the hydroxymethyl derivatives can be converted to the corresponding E-4 as mesylate (R'=Me) or nosylate (R'=3-$NO_2$Ph) by treatment with methanesulfonyl chloride in the presence of triethylamine or pyridine, or meta-nitrophenylsulfonyl chloride in the presence of pyridine respectively. The resulting sulfonate can be treated with an alkali metal azide, such as potassium or sodium azide in an aprotic solvent such as DMF, or N-methylpyrrolidinone (NMP) with an optional catalyst such as 18-crown-6 at a temperature in the range of 50–90° C. to afford azides. The azides can be reduced to the corresponding amine E-5 by hydrogenation in the presence of a palladium, platinum or nickel catalyst, in an appropriate solvent such as THF, ethyl acetate, or methanol. Alternatively, azides can be reduced to amines by treatment with triphenylphosphine or other trivalent phosphorous compounds in a solvent such as THF, followed by addition of water and heating to temperatures up to 65° C. A more direct route to the amines E-5 is to reflux the sulfonates in isopropanol (or methanol)/THF/ammonium hydroxide under a dry ice/acetone condenser or in a pressure vessel. The amines E-5 thus obtained can be acylated by reactions well known to those skilled in the art to give (acylaminomethyl)oxazolidinones of structural formula E-8. Furthermore, treatment of E-8 (W=O) with Lawesson's reagent in refluxing toluene or THF will afford the corrsponding thioamides (W=S). The Cbz-group of the (acylaminomethyl)oxazolidinones E-6 can be removed via hydrogenation in the presence of an appropriate catalyst such as palladium on carbon in solvents such as THF, methanol, ethyl acetate, dichloromethane or mixtures thereof to afford deprotected intermediates of general structure E-7 ($R^3$=H). Alternatively, solvolysis of Cbz-derivatives E-6 in 40% HBr/acetic acid followed by removal of solvent provides deprotected intermediates as hydrobromide salts. The deprotected materials can be acylated by reactions well known to those skilled in the art to give oxazolidinones E-8 wherein R3 is acyl. It can also be seen that other acyl derivatives, such as carbamates, can be prepared under similar conditions. In addition, the deprotected materials can be alkylated by reactions well known to those skilled in the art to give oxazolidinones of structural formula E-8 wherein $R^3$=alkyl.

As shown in Scheme F, the commercially available compound F-1 is treated with hydroxyl amine and sodium acetate in ethanol and water followed by treatment with polyphosphoric acid to give the ring expanded structure F-2. Protection of the aryl amine of F-2 with 2,5-hexanedione in toluene with an appropriate acid catalyst such as p-toluenesulfonic acid gives F-3. The amide is then reduced to the amine with lithium aluminum hydride in THF to give F-4. The protecting group is removed with hydroxyl amine and triethyl amine in ethanol and water to give the diamine F-5 which is converted to F-6 with benzyl chloroformate (2 equivalents) in acetone and water with sodium bicarbonate. The remaining steps which lead to the desired oxazolidinone analogs of type F-7 are similar to these described in Scheme E.

As shown in Scheme G, beginning with the commercially available compound G-1, ring expansion with hydrazoic acid in chloroform or dichloromethane and sulfuric acid gives the lactam G-2. Nitration of G-2 with nitric acid in sulfuric acid gives G-3. Structure G-3 is then reacted with a suitable borane such as borane in THF or borane-methyl sulfide complex in THF to give G-4. The nitro group can then be reduced by catalytic hydrogenation in the presence of a suitable catalyst such as palladium on carbon in a suitable solvent such as methanol, ethanol, ethyl acetate, THF or combinations thereof provides amino intermediates. Alternatively, one can reduce the nitro group with palladium on carbon and hydrazine in methanol or ethanol. Treatment of the amino intermediates with benzyl chloroformate (2 equivalents) in THF with an appropriate base, such as sodium carbonate, potassium carbonate or triethyl amine provides the bis-Cbz protected G-5. The remaining steps which lead to G-5 to the desired oxazolidinone analogs of type G-6 are similar to these described in Scheme E.

As shown in Scheme H, nitration of the known compound H-1 can be accomplished using nitric acid in concentrated sulfuric acid (Himmelsbach DE 4429079) to afford H-2. The resulting diacid is reduced to the corresponding diol H-3 using borane in THF or other appropriate reducing agents. Treatment of the diol with methanesulfonyl chloride, as described in Scheme D, affords the bismesylate H-4. Using steps outlined previously in Scheme C, the nitro group of H-4 is then reduced and the amine protected as its Cbz derivative to give H-5. Similarly, the nitro group of H-4 can be reduced using tin II chloride in ethanol at 70° C. followed by Cbz protection of the free amine as described. Cyclization to the benzothiepin ring system is accomplished using sodium sulfide in dimethylsulfoxide as described in Scheme D to give H-6. The Cbz-protected benzothiepin H-6 is then converted to the desired analog H-7 using methods similar to those described in Scheme C.

Scheme I illustrates the preparation of the sulfoxide and sulfone analogs of I-1. Treatment of sulfide I-1 with sodium metaperiodate in methanol and water affords the sulfoxide I-2. Likewise, oxidation to the sulfone I-3 is accomplished using osmium tetroxide and N-methylmorpholine N-oxide. Similarly, oxidation can be accomplished using Oxone as the oxidant.

As shown in Scheme J, the Cbz-protected benzothiepin, J-1 is converted to the Boc-protected aminomethyloxazolidinone J-2 using conditions described in Scheme B. Removal of the Boc-protecting group and reaction of the resulting free amine with ethyl dithioacetate affords compound J-3 using conditions described in Scheme A for the conversion of A-9 to A-11. Using conditions described in Scheme I, J-2 is first oxidized to the sulfoxide and then converted to the thioacetamide, J-5, using conditions described in Scheme A. Similarly, J-2 can be oxidized to the sulfone using conditions described in Scheme I and then converted to the thioacetamide using the conditions described in Scheme A to give J-4.

As outlined in Scheme K, the carbamate derivatives K-1 (R=$C_{1-6}$alkyl or benzyl) can be deprotonated with a lithium base such as n-butyllithium in a suitable solvent such as THF at a suitable temperature, typically in a range from −78° C. to −40° C., to give a lithiated intermediate which is directly treated with R-(−)-glycidyl butyrate. Warming to room temperature then affords the (5R)-hydroxymethyl oxazolidinones K-2. In cases where racemic starting materials are used, K-2 is obtained as a mixture of two enantiomers. The heteroaryl ethers K-4 (A=O) can be obtained directly from the alcohols K-2 under Mitsunobu conditions by treatment with het-OH (het is a heteroaryl ring defined previously) in the presence, for example, of free or polymer-bound triphenylphosphine and diethyl (or diisopropyl) azodicarboxylate. Additionally, the alcohols K-2 can be deprotonated with a base such as sodium hydride in a solvent such as DMF. Treatment with het-Lg, wherein Lg is an appropriate leaving group such as Br or Cl, then affords the heteroaryl ethers K-4 (A=O).

Alternatively, the alcohols K-2 can be converted to their alkyl halides, mesylates or tosylates K-3 (Lg=Hal, OMs, OTs) using methods known to those skilled in the art. Treatment of K-3 then with HET-OM, wherein M is an alkali metal or silver for example, provides the heteroaryl ethers K-4 (A=O) as well. The heteroaryl thioethers K-4 (A=S) can similarly De prepared from the alkyl halides, mesylates or tosylates K-3 by treatment with het-SM (M as defined above) or with het-SH in the presence of a base such as DBU. The alcohols K-2 can also be treated with het-NH-Pg, wherein Pg is a protecting group such as BOC, in the presence, for example, of tributylphosphine and 1,1′-(azodicarbonyl)dipiperidine (Mitsunobu conditions). The protecting group (Pg) can then be removed using methods known to those skilled in the art to provide the corresponding heteroaryl amines K-4 (A=NH). Alternatively, the alkyl halides, mesylates or tosylate K-3 can be treated with het-NM-Pg or het-NHM, wherein M is lithium or sodium for example, and the protecting group (Pg) can be removed as before to afford the heteroaryl amines K-4 (A=NH). The het starting materials used in these procedures (i.e., het-OH, het-SH, het-Lg, het-NH$_2$ and het-NH-Pg) are either commercially available or can be prepared by methods described in WO 99/64416, WO 99/64417 and WO 00/21960 or by methods known to those skilled in the art.

As shown in Scheme L, acetophenones which are commercially available or readily accessed by those skilled in the art when treated with thallium (III) nitrate trihydrate and 70% perchloric acid in methanol or ethanol (*JACS*, 1971, 93, 4919–4920) will yield the esters L-2. Alternatively, L-1 may be converted to L-2 under Willgerodt-Kindler conditions (*J. Heterocyclic Chem.* 1989, 26, 1319–1323) by heating L-1 with sulfur in morpholine followed by hydrolysis with hydrochloric acid. Treatment of L-2 with sodium hydride in ethylformate will yield the formylated derivatives L-3. The isoxazolinone rings can be prepared by treating L-3 with aqueous hydroxylamine in methanol. The solvent can be stripped off in vacuo and the residue treated with N-(hydroxymethyl)acetamide acetate in dichloromethane with a suitable base such as potassium carbonate. This process yields the products L-4. The requisite N-(hydroxymethyl)acetamide acetate is prepared as described by WO 00/10566.

The thioamides L-5 (W=S) can be prepared by treating L-4 with Lawesson's reagent in tetrahydrofuran, dioxane or toluene at temperatures ranging from 50–110° C.

These compounds are useful for the treatment of microbial infections, including ophthalmologic infections, in humans and other warm blooded animals, under both parenteral and oral administration.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 150, more preferably about 3.0 to about 100 mg/kg of body weight/day. A single 600 mg dose per day by IV or oral is preferred. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formula I according to this invention are advantageously administered orally in solid and liquid dosage forms.

The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa. USA. The activity of compounds of this invention against, *Streptococcus pneumoniae*, is shown in Table 1.

TABLE 1

Antibacterial Activity Minimum Inhibitory Concentration ($\mu$g/mL)

| Example No. | SPNE 9912 |
| --- | --- |
| 1 | 1 |
| 2 | 1 |
| 3 | 1 |
| 4 | 1 |
| 5 | <0.5 |
| 6 | <0.5 |
| 7 | <0.5 |
| 8 | 4 |
| 9 | 1 |
| 10 | 1 |
| 11 | 0.25 |
| 12 | 1 |
| 13 | 1 |
| 14 | 0.5 |
| 15 | 0.125 |
| 16 | 1 |
| 17 | 2 |
| 18 | 1 |
| 19 | 2 |
| 20 | <0.5 |
| 21 | <0.5 |
| 22 | <0.5 |
| 23 | <0.5 |
| 24 | <0.5 |
| 25 | 1 |
| 26 | 1 |
| 27 | 1 |
| 28 | 4 |
| 29 | 2 |
| 30 | 1 |
| 31 | 1 |
| 32 | 2 |
| 33 | 2 |
| 34 | 2 |
| 35 | 1 |
| 36 | <0.5 |
| 37 | 1 |
| 38 | 2 |
| 38 | 2 |
| 40 | 1 |

TABLE 1-continued

Antibacterial Activity Minimum Inhibitory Concentration (μg/mL)

| Example No. | SPNE 9912 |
|---|---|
| 41 | 0.125 |
| 42 | 0.5 |
| 43 | 0.5 |
| 44 | 1 |
| 45 | 0.5 |
| 46 | 0.5 |
| 47 | 2 |
| 48 | 8 |
| 49 | 0.5 |
| 50 | 1 |

EXAMPLES

Example 1

(−)-Methyl 6-[(5S)-5-[(acetylamino)methyl]-2-oxo-3-oxazolidinyl]-3,4-dihydro-2(1H)-isoquinolinecarboxylate

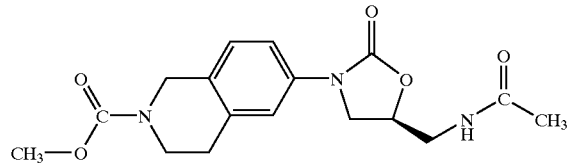

Step 1 Preparation of N-benzyl-6-nitro-1,2,3,4-tetrahydroisoquinoline

A solution of 2-[2-(hydroxymethyl)-5-nitrophenyl] ethanol (5.95 g, 30.17 mmol, J. Org. Chem., 1998, 63, 4116–4119) and triethylamine (10.51 mL, 75.42 mmol) in dry $CH_2Cl_2$ (121 mL) at 0° C. under $N_2$ is treated with methanesulfonyl chloride (5.37 mL, 69.39 mmol) dropwise and stirred at 0° C. for 30 mins. The mixture is then washed with 1M aqueous HCl (100 mL), saturated aqueous $NaHCO_3$ (100 mL) and brine (100 mL), dried over $Na_2SO_4$ and concentrated under reduced pressure to give the dimesylate intermediate [$R_f$=0.77 by TCL (MeOH/$CHCl_3$, 10/90)] as a partially crystalline oil. To a solution of this oil in $CH_2Cl_2$ (151 mL) under $N_2$ is added benzylamine (16.48 mL, 150.8 mmol), and the resulting mixture is stirred at ambient temperature for 22 hrs and is then washed with water (100 mL) and brine (100 mL), dried over anhydrous $Na_2SO_4$ and concentrated under reduced pressure. The crude product is purified by silica gel chromatography (350 g, 230–400 mesh), eluting with EtOAc/heptane (10/90), to give 7.76 g (96%) of the title compound [$R_f$=0.43 by TLC (EtOAc/hexane, 25/75)] as a light yellow solid, mp 76–78° C.

Step 2 Preparation of phenylmethyl 3,4-dihydro-6-[[(phenylmethoxy)carbonyl]amino]-2(1H)-isoquinolinecarboxylate A solution of N-benzyl-6-nitro-1,2,3,4-tetrahydroisoquinoline (Step 1, 7.75 g, 28.99 mmol) in THF/MeOH (20/80, 290 mL) is added to two Parr bottles containing 10% Pd/C (1.54 g each), and the mixtures are shaken under 45 psi $H_2$ for a total of 3.5 hrs. The catalyst is then removed by filtration through Celite and the combined filtrate is concentrated under reduced pressure to give the crude 6-amino-1,2,3,4-tetrahydroisoquinoline intermediate as a partially crystalline oil [$R_f$=0.03 by TLC (MeOH/$CHCl_3$, 10/90)]. A mixture of this intermediate and $NaHCO_3$ (5.36 g, 63.78 mmol) in THF/$H_2O$ (2/1, 116 mL) at 0° C. is treated with benzyl chloroformate (9.11 mL, 63.78 mmol) dropwise, and the resulting mixture is stirred at 0° C. for approximately 45 mins, additional THF/$H_2O$ (2/1, 116 mL) being added after 15 mins. The layers are then separated, the organic phase is washed with saturated aqueous $NaHCO_3$ (100 mL), the combined aqueous phase is reextracted with EtOAc (100 mL), and the combined organic phase is washed with brine (50 mL), dried over anhydrous $Na_2SO_4$, and concentrated under reduced pressure to give the crude product which is then chromatographed on silica gel (350 g, 230–400 mesh), eluting with a gradient of EtOAc/heptane (7.5/92.5–20/80). Pooling and concentration of those fractions with an $R_f$=0.24 by TLC (EtOAc/hexane, 25/75) and recrystallization from EtOAc (75 mL)/hexane (175 mL) provides 7.10 g (59%) of the title compound as a white solid, mp 115–116° C. An additional 2.0 g of impure product is isolated in the recrystallization.

Step 3 Preparation of (+)-phenylmethyl 6-[(5R)-5-(hydroxymethyl)-2-oxo-3-oxazolidinyl]-3,4-dihydro-2(1H)-isoquinolinecarboxylate A solution of 3,4-dihydro-6-[[(phenylmethoxy)carbonyl]amino]-2(1H)-isoquinolinecarboxylate (Step 2, 7.05 g, 16.93 mmol) in dry THF (85 mL) at −78° C. under $N_2$ is treated with n-butyllithium (11.1 mL, 1.6M in hexanes, 17.77 mmol) dropwise over 10 mins. The resulting mixture is stirred at −78° C. for 45 mins and is then treated with (R)-(−)-glycidyl butyrate (2.52 mL, 17.77 mmol) dropwise. The resulting mixture is stirred at −78° C. for 30 mins and is then warmed to ambient temperature and stirred for an additional 20 hrs. The reaction is then quenched with saturated aqueous $NH_4Cl$ (25 mL), diluted with $H_2O$ (25 mL) and extracted with EtOAc (100 mL). The organic phase is washed with $H_2O$ (2×50 mL) and brine (25 mL), dried over anhydrous $MgSO_4$ and concentrated under reduced pressure to give the crude product which is then chromatographed on silica gel (350 g, 230–400 mesh), eluting with a gradient of MeOH/$CH_2Cl_2$ (1/99–3/97). Pooling and concentration of those fractions with an $R_f$=0.29 by TLC (MeOH/$CHCl_3$, 5/95) provides 4.48 g (69%) of the title compound as an amorphous, white solid. $^1$H NMR (400 MHz, $CDCl_3$) δ 7.37 (m, 7H), 7.11 (m, 1H), 5.19 (s, 2H), 4.75 (m, 1H), 4.63 (s, 2H), 4.00 (m, 3H), 3.75 (m, 3H), 2.86 (m, 2H) 1.65 (bs, 1H); MS (ESI+) for $C_{21}H_{22}N_2O_5$ m/z 383 (M+H)$^+$; [α]$^{25}_D$=16° (c 0.52, chloroform).

Step 4 Preparation of (−)-phenylmethyl 6-[(5S)-5-(aminomethyl)-2-oxo-3-oxazolidinyl]-3,4-dihydro-2(1H)-isoquinolinecarboxylate A solution of phenylmethyl 6-[(5R)-5-(hydroxymethyl)-2-oxo-3-oxazolidinyl]-3,4-dihydro-2(1H)-isoquinolinecarboxylate (Step 3, 4.36 g, 11.40 mmol) and triethylamine (2.38 mL, 17.10 mmol) in dry $CH_2Cl_2$ (57 mL) at 0° C. under $N_2$ is treated with methanesulfonyl chloride (0.97 mL, 12.54 mmol) dropwise and stirred at 0° C. for 1 hr. The mixture is then diluted with $CH_2Cl_2$ (60 mL), washed with $H_2O$ (25 mL) and brine (25 mL), dried over $Na_2SO_4$ and concentrated under reduced pressure to give the mesylate intermediate [$R_f$=0.61 by TLC (MeOH/$CHCl_3$, 5/95)] as an amorphous, white solid which is used without further purification. A mixture of this intermediate and concentrated aqueous $NH_4OH$ (9.1 mL) in isopropanol (4.6 mL) and acetonitrile (9.1 mL) is placed in a thick-walled screw-cap tube and immersed in an oil bath maintained at 80° C. and the contents are stirred at this temperature for 40 hrs, during which additional concentrated aqueous $NH_4OH$ (4 mL) is added. The mixture is then cooled to ambient temperature, diluted with half-saturated aqueous NaCl (50 mL) and extracted with $CH_2Cl_2$ (2×100 mL). The combined organic phase is dried over anhydrous $Na_2SO_4$ and concentrated under reduced pressure, and the crude product is chromatographed on silica gel (350 g, 230–400 mesh), eluting with a gradient of $MeOH/CH_2Cl_2$ (1/99–5/95). Pooling and concentration of those fractions with an $R_f$=0.09 by TLC (MeOH/$CHCl_3$, 5/95) provides 2.97 g (68%) of the title compound as an amorphous, glassy solid. $^1$H NMR (400 MHz, $CDCl_3$) δ 7.37 (m, 7H), 7.10 (m, 1H), 5.19 (s, 2H), 4.72 (m, 1H), 4.62 (s, 2H), 4.05 (t, 1H), 3.85 (dd, 1H), 3.71 (m, 2H), 3.20–3.00 (m, 2H), 2.86 (m, 2H); MS (ESI+) for $C_{21}H_{23}N_3O_4$ m/z 382 (M+H)$^+$; $[α]^{25}_D$=–27° (c 0.28, DMSO).

Step 5 Preparation of (–)-phenylmethyl 6-[(5S)-5-[(acetylamino)methyl]-2-oxo-3-oxazolidinyl]-3,4-dihydro-2(1H)-isoquinolinecarboxylate A solution of phenylmethyl 6-[(5S)-5-(aminomethyl)-2-oxo-3-oxazolidinyl]-3,4-dihydro-2(1H)-isoquinolinecarboxylate (Step 4, 1.75 g, 4.59 mmol) and pyridine (1.11 mL, 13.77 mmol) in dry $CH_2Cl_2$ (23 mL) under $N_2$ is treated with acetic anhydride (0.649 mL, 6.88 mmol), and the mixture is stirred at ambient temperature for 3.5 hrs. The mixture is then washed with $H_2O$ (2×15 mL) and brine (10 mL), dried over $Na_2SO_4$ and concentrated under reduced pressure. The crude product is chromatographed on a Flash 40S silica gel (40 g, 32–63 μm) cartridge, eluting with a gradient of $MeOH/CH_2Cl_2$ (0.5/99.5–2/98), and those fractions with an $R_f$=0.25 by TLC (MeOH/$CHCl_3$, 5/95) are pooled and concentrated to give 1.81 g (93%) of the title compound as an amorphous, white solid. $^1$H NMR (400 MHz, $CDCl_3$) δ 7.35 (m, 7H), 7.11 (m, 1H), 6.11 (m, 1H), 5.19 (s, 2H), 4.78 (m, 1H), 4.62 (s, 2H), 4.05 (t, 1H), 3.78 (dd, 1H), 3.70 (m, 3H), 3.60 (m, 1H), 2.86 (m, 2H), 2.02 (s, 3H); MS (ESI+) for $C_{23}H_{25}N_3O_5$ m/z 424 (M+H)$^+$; $[α]^{25}_D$=–17° (c 0 77, DMSO).

Step 6 Preparation of N-[[(5S)-3-[1,2,3,4-tetrahydro-6-isoquinolinyl]-2-oxo-5-oxazolidinyl]methyl]acetamide A mixture of phenylmethyl 6-[(5S)-5-[(acetylamino)methyl]-2-oxo-3-oxazolidinyl]-3,4-dihydro-2(1H)-isoquinolinecarboxylate (Step 5, 1.71 g, 4.04 mmol) and 20% Pd(OH)$_2$/C (567 mg) in MeOH (40 mL) in a Parr bottle is shaken under 20 psi $H_2$ for 1 hr. The resulting slurry is then diluted with MeOH (100 mL) and THF (100 mL), filtered through Celite to remove the catalyst, and concentrated under reduced pressure to give a quantitative yield of the title compound as an amorphous solid which is used without further purification. $^1$H NMR (400 MHz, $CD_3OD$) δ 7.36 (bd, 1H), 7.31 (s, 1H), 7.08 (d, 1H), 4.78 (m, 1H), 4.14 (t, 1H), 3.98 (s, 2H), 3.82 (dd, 1H), 3.57 (m, 2H), 3.13 (m, 2H), 2.88 (m, 2H), 1.98 (s, 3H); MS (ESI+) for $C_{15}H_{19}N_3O_3$ m/z 290 (M+H)$^+$.

Step 7 Preparation of (–)-methyl 6-[(5S)-5-[(acetylamino)methyl]-2-oxo-3-oxazolidinyl]-3,4-dihydro-2(1H)-isoquinolinecarboxylate A mixture of N-[[(5S)-3-[1,2,3,4-tetrahydro-6-isoquinolinyl]-2-oxo-5-oxazolidinyl]methyl]acetamide (Step 6, 450 mg, 1.55 mmol) and $NaHCO_3$ (260 mg, 3.10 mmol) in THF (15.5 mL) under $N_2$ is treated with methyl chloroformate (0.144 mL, 1.87 mmol) with vigorous stirring. A thick, white slurry results which is redissolved by the addition of $H_2O$ (approx. 2 mL). The mixture is stirred at ambient temperature for 1 hr and is then diluted with $H_2O$ (10 mL) and EtOAc (20 mL) and the layers are separated. The aqueous phase is reextracted with $CH_2Cl_2$ (20 mL), and the combined organic phase is washed with brine (10 mL), dried over anhydrous $Na_2SO_4$ and concentrated under reduced pressure. The crude product is chromatographed on silica gel (45 g, 230–400 mesh), eluting with MeOH/$CHCl_3$ (2/98), and those fractions with an $R_f$=0.51 by TLC (MeOH/$CHCl_3$, 10/90) are pooled and concentrated to give 475 mg (88%) of the title compound as a glassy solid. $^1$H NMR (400 MHz, $CDCl_3$) δ 7.32 (m, 2H), 7.11 (m, 1H), 6.19 (m, 1H), 4.76 (m, 1H), 4.59 (s, 2H), 4.05 (t, 1H), 3.78 (dd, 1H), 3.75 (s, 3H), 3.75–3.50 (m, 4H), 2.85 (m, 2M), 2.02 (s, 3H); MS (ESI+) for $C_{17}H_{21}N_3O_5$ m/z 348 (M+H)$^+$; $[α]^{25}_D$=–20° (c 1.04, DMSO).

Example 2

(–)-N-[[(5S)-3-[2-Formyl-1,2,3,4-tetrahydro-6-isoquinolinyl]-2-oxo-5-oxazolidinyl]methyl]acetamide

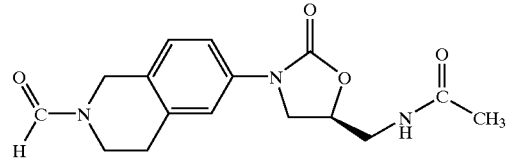

A solution of N-[[(5S)-3-[1,2,3,4-tetrahydro-6-isoquinolinyl]-2-oxo-5-oxazolidinyl]methyl]acetamide (Example 1, Step 6, 200 mg, 0.691 mmol) in THF is treated with EDC.HCl (172 mg, 0.899 mmol) and formic acid (34 μL, 0.899 mmol) to give a white slurry which is then diluted with $H_2O$ (approx. 2 mL) to give a homogeneous mixture. The mixture is stirred at ambient temperature for 1.25 hrs and is then diluted with $H_2O$ (10 mL) and extracted with $CH_2Cl_2$ (4×20 mL). The combined organic phase is washed with brine (10 mL), dried over anhydrous $Na_2SO_4$ and concentrated under reduced pressure, and the crude product is chromatographed on a Flash 40S silica gel (40 g, 32–63 μm) cartridge, eluting with a gradient of $MeOH/CH_2Cl_2$ (1/99–5/95). Those fractions with an $R_f$=0.41 by TLC (MeOH/$CHCl_3$, 10/90) are pooled and concentrated and the resulting glassy solid is triturated with $Et_2O$ and filtered to give 161 mg (74%) of the title compound as a white solid, mp 139–141° C. (dec.). $[α]^{25}_D$=–22° (c 0.92, DMSO).

Example 3

(–)-N-[[(5S)-3-[2-[(Acetyloxy)acetyl]-1,2,3,4-tetrahydro-6-isoquinolinyl]-2-oxo-5-oxazolidinyl]methyl]acetamide

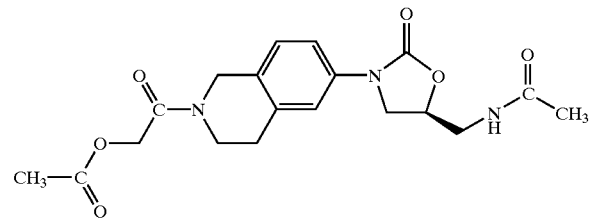

A solution of N-[[(5S)-3-[1,2,3,4-tetrahydro-6-isoquinolinyl]-2-oxo-5-oxazolidinyl]methyl]acetamide (Example 1, Step 6, 350 mg, 1.21 mmol) and triethylamine (0.252 mL, 1.81 mmol) in dry $CH_2Cl_2$ (6 mL) under $N_2$ is cooled to 0° C. and treated with acetoxyacetyl chloride (0.156 mL, 1.45 mmol). The resulting mixture is stirred at 0° C. for 1 hr and is then warmed to ambient temperature, diluted with $CH_2Cl_2$ (20 mL), washed with $H_2O$ (10 mL)

and brine (10 mL), dried over Na₂SO₄ and concentrated under reduced pressure. The crude product is chromatographed on a Flash 40S silica gel (40 g, 32–63 μm) cartridge, eluting with a gradient of MeOH/CH₂Cl₂ (1/99–3/97), and those fractions with an R$_f$=0.44 by TLC (MeOH/CHCl₃, 10/90) are pooled and concentrated to give 323 mg (69%) of the title compound as a glassy solid. An analytical sample is prepared by trituration and filtration from Et₂O. MS (ESI+) for C₁₉H₂₃N₃O₆ m/z 390 (M+H)⁺; Anal. Calcd for C₁₉H₂₃N₃O₆: C, 58.60; H, 5.95; N, 10.79. Found: C, 58.46; H, 6.06; N, 10.66; [α]$^{25}_D$=−18° (c 0.93, DMSO).

Example 4

(−)-N-[[(5S)-3-[2-[(Hydroxy)acetyl]-1,2,3,4-tetrahydro-6-isoquinolinyl]-2-oxo-5-oxazolidinyl]methyl]acetamide

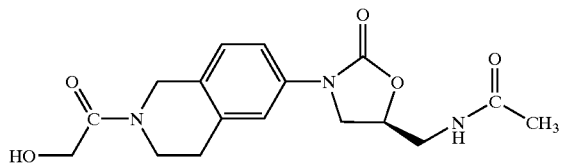

A solution of N-[[(5S)-3-[2-[(acetyloxy)acetyl]-1,2,3,4-tetrahydro-6-isoquinolinyl]-2-oxo-5-oxazolidinyl]methyl] acetamide (Example 3, 230 mg, 0.591 mmol) in MeOH (5.9 mL) is treated with K₂CO₃ (163 mg, 1.18 mmol), and the resulting mixture is stirred at ambient temperature for 1 hr and is then adjusted to pH 7 with 1M aqueous HCl and concentrated under reduced pressure. The residue is diluted with brine (10 mL) and extracted with CH₂Cl₂ (3×20 mL), and the combined organic phase is dried over anhydrous Na₂SO₄ and concentrated under reduced pressure. The crude product is then chromatographed on a Flash 40S silica gel (40 g, 32–63 μm) cartridge, eluting with a gradient of MeOH/CH₂Cl₂ (2/98–5/95), and those fractions with an R$_f$=0.25 by TLC (MeOH/CHCl₃, 10/90) are pooled and concentrated and the residue triturated with Et₂O to give 146 mg (71%) of the title compound as an amorphous, white solid. MS (ESI+) for C₁₇H₂₁N₃O₅ m/z 348 (M+H)⁺; [α]$^{25}_D$=−18° (c 0.96, DMSO); Anal. Calcd for C₁₇H₂₁N₃O₅: C, 58.78; H, 6.09; N, 12.10. Found: C, 58.59; H, 6.49; N, 11.77.

Example 5

(+)-Methyl 6-[(5S)-5-[(ethanethioylamino)methyl]-2-oxo-3-oxazolidinyl]-3,4-dihydro-2(1H)-isoquinolinecarboxylate

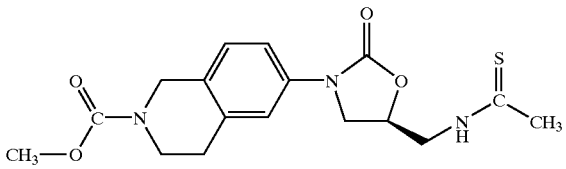

A mixture of methyl 6-[(5S)-5-[(acetylamino)methyl]-2-oxo-3-oxazolidinyl]-3,4-dihydro-2(1H)-isoquinolinecarboxylate (Example 1, 280 mg, 0.806 mmol) and Lawesson's reagent (179 mg, 0.443 mmol) in dry THF (8.1 mL) under N₂ is heated up to 60° C. over 15 mins, stirred at this temperature for 5 mins, and then cooled to ambient temperature and concentrated under reduced pressure. The crude product mixture is then chromatographed on a Flash 40S silica gel (40 g, 32–63 μm) cartridge, eluting with MeOH/CH₂Cl₂ (2/98), and those fractions with an R$_f$=0.57 by TLC (MeOH/CHCl₃, 10/90) are pooled and concentrated and the residue recrystallized from CH₂Cl₂/Et₂O to give 216 mg (74%) of the title compound as an off-white solid, mp 149–150° C. (dec.); [α]$^{25}_D$=5° (c 0.99, DMSO).

Example 6

(+)-N-[[(5S)-3-[2-Formyl-1,2,3,4-tetrahydro-6-isoquinolinyl]-2-oxo-5-oxazolidinyl]methyl]ethanethioamide

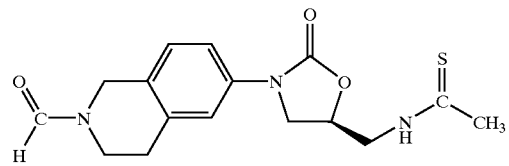

Step 1 Preparation of (−)-phenylmethyl 6-[(5S)-5-[[[(1,1-dimethylethoxy)carbonyl]amino]methyl]-2-oxo-3-oxazolidinyl]-3,4-dihydro-2(1H)-isoquinolinecarboxylate A mixture of phenylmethyl 6-[(5S)-5-(aminomethyl)-2-oxo-3-oxazolidinyl]-3,4-dihydro-2(1H)-isoquinolinecarboxylate (Example 1, Step 4, 1.03 g, 2.70 mmol), di-t-butyl dicarbonate (619 mg, 2.84 mmol) and NaHCO₃ (250 mg, 2.97 mmol) in THF/H₂O (2/1, 21.6 mL) is stirred at ambient temperature for 3.5 hrs and is then diluted with H₂O (10 mL) and extracted with EtOAc (2×15 mL). The combined organic phase is washed with H₂O (10 mL) and brine (10 mL), dried over anhydrous MgSO₄ and concentrated under reduced pressure to give the crude product which is chromatographed on a Flash 40S silica gel (40 g, 32–63 μm) cartridge, eluting with a gradient of MeOH/CH₂Cl₂ (0.5/99.5–2/98). Pooling and concentration of those fractions with an R$_f$=0.65 by TLC (MeOH/CHCl₃, 5/95) provides 1.21 g (93%) of the title compound as an amorphous, white solid. ¹H NMR (400 MHz, CDCl₃) δ 7.37 (m, 7H), 7.10 (m, 1H), 5.19 (s, 2H), 4.98 (m, 1H), 4.75 (m, 1H), 4.62 (s, 2H), 4.03 (t, 1H), 3.83 (m, 1H), 3.72 (m, 2H), 3.50 (m, 2H), 2.86 (m, 2H), 1.42 (s, 9H); MS (ESI−) for C₂₆H₃₁N₃O₆ m/z 480 (M−H)⁻; [α]$^{25}_D$=−25° (c 0.66, DMSO).

Step 2 Preparation of 1,1-dimethylethyl [[(5S)-2-oxo-3-[1,2,3,4-tetrahydro-6-isoquinolinyl]-5-oxazolidinyl]methyl] carbamate A mixture of phenylmethyl 6-[(5S)-5-[[[(1,1-dimethylethoxy)carbonyl]amino]-methyl]-2-oxo-3-oxazolidinyl]-3,4-dihydro-2(1H)-isoquinolinecarboxylate (Step 1, 1.11 g, 2.31 mmol) and 20% Pd(OH)₂/C (324 mg) in MeOH (23 mL) in a Parr bottle is shaken under 20 psi H₂ for 1.25 hr. The resulting mixture is filtered through Celite to remove the catalyst, and the filtrate is concentrated under reduced pressure to give a quantitative yield of the product as an amorphous solid which is used without further purification. ¹H NMR (400 MHz, CD₃OD) δ 7.35 (bd, 1H), 7.31 (s, 1H), 7.08 (d, 1H), 4.75 (m, 1H), 4.14 (t, 1H), 3.97 (s, 2H), 3.87 (m, 1H), 3.42 (m, 2H), 3.11 (m, 2H), 2.87 (m, 2H), 1.42 (s, 9H); MS (ESI+) for C₁₈H₂₅N₃O₄ m/z 348 (M+H)$^{30}$.

Step 3 Preparation of 1,1-dimethylethyl [[(5S)-2-oxo-3-[2-formyl-1,2,3,4-tetrahydro-6-isoquinolinyl]-5-oxazolidinyl]methyl]carbamate A solution of 1,1-dimethylethyl [[(5S)-2-oxo-3-[1,2,3,4-tetrahydro-6-isoquinolinyl]-5-oxazolidinyl]methyl]

carbamate (Step 2, 292 mg, 0.841 mmol) in dry THF (16.8 mL) is treated with 1H-benzotriazol-1-carboxaldehyde (148 mg, 1.01 mmol), and the resulting suspension is stirred at ambient temperature for 1.25 hrs and is then concentrated to remove THF. The residue is rediluted with $CH_2Cl_2$ (25 mL), washed with 1N aqueous NaOH (2×10 mL) and brine (10 mL), dried over $Na_2SO_4$ and concentrated under reduced pressure to give the crude product which is then chromatographed on a Flash 40S silica gel (40 g, 32–63 μm) cartridge, eluting with $MeOH/CH_2Cl_2$ (2.5/97.5). Those fractions with an $R_f$=0.60 by TLC ($MeOH/CHCl_3$, 10/90) are pooled and concentrated to give 310 mg (98%) of the title compound as an amorphous, glassy solid. MS (ESI+) for $C_{19}H_{25}N_3O_5$ m/z 376 (M+H)$^+$.

Step 4 Preparation of (+)-N-[[(5S)-3-[2-formyl-1,2,3,4-tetrahydro-6-isoquinolinyl]-2-oxo-5-oxazolidinyl]methyl]ethanethioamide Ice-cold 4N HCl in dioxane (6.6 mL) is added to a flask containing 1,1-dimethylethyl [[(5S)-2-oxo-3-[2-formyl-1,2,3,4-tetrahydro-6-isoquinolinyl]-5-oxazolidinyl]methyl]carbamate (Step 3, 249 mg, 0.663 mmol), and the resulting slurry is stirred at 0° C. for 1 hr. The mixture is then diluted with MeOH (approx. 6 mL) to give a homogeneous mixture which is stirred for 30 mins and is then concentrated under reduced pressure to give the deprotected aminomethyl oxazolidinone intermediate as its hydrochloride salt [MS (ESI+) for $C_{14}H_{17}N_3O_3$ m/z 276 (M+H)$^+$] which is used without further purification. A solution of this intermediate and triethylamine (277 μL, 1.99 mmol) in dry $CH_2Cl_2$ (6.6 mL) is treated with ethyl dithioacetate (91 μL, 0.796 mmol). The mixture is stirred for 4.5 hrs, during which additional triethylamine (92 μL) and ethyl dithioacetate (91 μL) are added, and is then diluted with $CH_2Cl_2$ (10 mL), washed with $H_2O$ (10 mL) and brine (10 mL), dried over $Na_2SO_4$ and concentrated under reduced pressure. The crude product is chromatographed on a Flash 40S silica gel (40 g, 32–63 μm) cartridge, eluting with a gradient of $MeOH/CH_2Cl_2$ (1/99–2/98), and those fractions with an $R_f$=0.54 by TLC ($MeOH/CHCl_3$, 10/90) are pooled and concentrated and triturated with $Et_2O$ to give 167 mg (76%) of the title compound as an amorphous, white solid. $^1H$ NMR (400 MHz, $CDCl_3$) δ (mixture of rotamers A and B) 8.27 (s, 1H$_B$), 8.21 (s, 1H$_A$), 8.05 (m, 1H$_A$+1H$_B$), 7.36–7.26 (m, 2H$_A$+2H$_B$), 7.13 (m, 1H$_A$+1H$_B$), 4.97(m, 1H$_A$+1H$_B$), 4.66 (s, 2H$_A$), 4.53 (s, 2H$_B$), 4.30 (m, 1H$_A$+1H$_B$), 4.08 (m, 2H$_A$+2H$_B$), 3.85 (m, 1H$_A$+1H$_B$), 3.79 (m, 2H$_B$), 3.65 (m, 2H$_A$), 2.90 (m, 2H$_A$+2H$_B$), 2.61 (s, 3H$_A$+3H$_B$); MS (ESI+) for $C_{16}H_{19}N_3O_3S_1$ m/z 334 (M+H)$^+$; $[α]^{25}_D$=4° (c 0.98, DMSO).

Example 7

(+)-N-[[(5S)-3-[2-[(Hydroxy)acetyl]-1,2,3,4-tetrahydro-6-isoquinolinyl]-2-oxo-5-oxazolidinyl]methyl]ethanethioamide

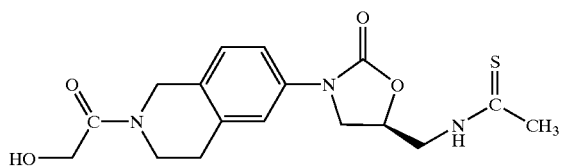

Step 1 Preparation of 1,1-dimethylethyl [[(5S)-2-oxo-3-[1,2,3,4-tetrahydro-2-[(phenylmethoxy)acetyl]-6-isoquinolinyl]-5-oxazolidinyl]methyl]carbamate A solution of 1,1-dimethylethyl [[(5S)-2-oxo-3-[1,2,3,4-tetrahydro-6-isoquinolinyl]-5-oxazolidinyl]methyl]carbamate (Example 6, Step 2, 347 mg, 0.999 mmol) and triethylamine (0.21 mL, 1.50 mmol) in dry $CH_2Cl_2$ at 0° C. under $N_2$ is treated with benzyloxyacetyl chloride (0.19 mL, 1.20 mmol), and the resulting mixture is stirred at 0° C. for 1 hr and then allowed to warm to ambient temperature. The reaction mixture is then diluted with $CH_2Cl_2$ (20 mL), washed with $H_2O$ (10 mL) and brine (10 mL), dried over $Na_2SO_4$ and concentrated under reduced pressure. The residue is chromatographed on a Flash 40S silica gel (40 g, 32–63 μm) cartridge, eluting with a gradient of $MeOH/CH_2Cl_2$ (1/99–2/98), and those fractions with an $R_f$=0.72 by TLC ($MeOH/CHCl_3$, 10/90) are pooled and concentrated to give 425 mg (86%) of the title compound as an amorphous, glassy solid. MS (ESI+) for $C_{27}H_{33}N_3O_6$ m/z 496 (M+H)$^+$.

Step 2 Preparation of (+)-N-[[(5S)-3-[2-[(hydroxy)acetyl]-1,2,3,4-tetrahydro-6-isoquinolinyl]-2-oxo-5-oxazolidinyl]methyl]ethanethioamide Ice-cold 4N HCl in dioxane (3.3 mL) is added to a flask containing 1,1-dimethylethyl [[(5S)-2-oxo-3-[1,2,3,4-tetrahydro-2-[(phenylmethoxy)acetyl]-6-isoquinolinyl]-5-oxazolidinyl]methyl]carbamate (Step 1, 330 mg, 0.666 mmol), and the resulting slurry is stirred at 0° C. for 1 hr. The mixture is then diluted with MeOH (approx. 8 mL) to give a homogeneous mixture which is stirred for 30 mins and is then concentrated under reduced pressure to give the deprotected aminomethyl oxazolidinone intermediate as its hydrochloride salt [MS (ESI+) for $C_{22}H_{25}N_3O_4$ m/z 396 (M+H)$^+$] which is used without further purification. A solution of this intermediate in MeOH/EtOH (1/1, 13.4 mL) is added to a Parr bottle containing 10% Pd-on-C (142 mg, 20 mol %) under $N_2$, and the mixture is shaken under 20 psi $H_2$ for approximately 7 hrs and is then filtered through Celite to remove the catalyst and concentrated under reduced pressure to give the debenzylated intermediate (complete reaction indicated by NMR and HPLC) which is also used without further purification. A solution of this intermediate and triethylamine (278 μL, 2.00 mmol) in dry $CH_2Cl_2$ (6.7 mL) is treated with ethyl dithioacetate (92 μL, 0.800 mmol). The mixture is stirred for 20 hrs, during which additional triethylamine (93 μL) and ethyl dithioacetate (92 μL) are added, and is then diluted with $CH_2Cl_2$ (10 mL), washed with $H_2O$ (10 mL) and brine (5 mL), dried over $Na_2SO_4$ and concentrated under reduced pressure. The crude product is chromatographed on a Flash 40S silica gel (40 g, 32–63 μm) cartridge, eluting with a gradient of $MeOH/CHCl_3$ (1/99–3/97), and those fractions with an $R_f$=0.43 by TLC (MeOH/$CHCl_3$, 10/90) are pooled and concentrated to give 149 mg (62%) of the title compound as an amorphous, white solid. $^1H$ NMR (400 MHz, $CDCl_3$) δ (mixture of rotamers A and B) 8.02 (m, 1H$_A$+1H$_B$), 7.40–7.26 (m, 2H$_A$+2H$_B$), 7.15 (m, 1H$_A$+1H$_B$), 4.98 (m, 1H$_A$+1H$_B$), 4.76 (s, 2H$_A$), 4.42 (s, 2H$_B$), 4.31 (m, 1H$_A$+1H$_B$), 4.26 (s, 2H$_A$+2H$_B$), 4.09 (m, 2H$_A$+2H$_B$), 3.86 (m, 1H$_A$+3H$_B$), 3.50 (m, 2H$_A$), 2.92 (m, 2H$_A$+2H$_B$), 2.61 (s, 3H$_A$+3H$_B$), 2.55 (bm, 1H$_A$+1H$_B$); MS (ESI+) for $C_{17}H_{21}N_3O_4S_1$ m/z 364 (M+H)[30]; HRMS (FAB) calcd for $C_{17}H_{21}N_3O_4S+H_1$ 364.1331, found 364.1340; $[α]^{25}_D$=3° (c 0.78, DMSO).

Example 8

(−)-N-[[(5S)-3-(3,4-Dihydro-1H-2-benzopyran-6-yl)-2-oxo-5-oxazolidinyl]methyl]acetamide

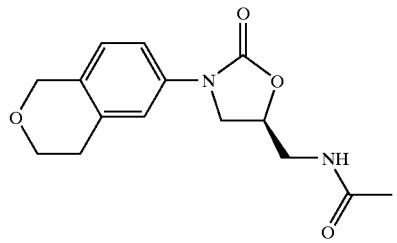

Step 1 Preparation of phenylmethyl (3,4-dihydro-1H-2-benzopyran-6-yl)carbamate

A mixture of PtO$_2$ (10 mol %, 148 mg) in MeOH (65 mL) is degassed and stirred under a hydrogen atmosphere (balloon) for 25 mins to activate the catalyst. Then, a solution of 3,4-dihydro-6-nitro-1H-2-benzopyran (1.17 g, 6.53 mmol, *J. Org. Chem.*, 1998, 63, 4116–4119) in MeOH (65 ml) is added, the mixture is stirred under a hydrogen atmosphere (balloon) for approximately 2 hrs, and the catalyst is then removed by filtration through Celite. The filtrate is concentrated under reduced pressure to give the 6-amino-3,4-dihydro-1H-2-benzopyran intermediate [MS (ESI+) for C$_9$H$_{11}$NO m/z 150 (M+H)$^+$] which is then dissolved in THF/H$_2$O (2:1, 66 mL) and treated with NaHCO$_3$ (576 mg, 6.86 mmol) and benzyl chloroformate (0.979 mL, 6.86 mmol). The resulting mixture is stirred at ambient temperature for 30 mins and is then diluted with EtOAc (100 mL), washed with H$_2$O (25 mL), saturated aqueous NaHCO$_3$ (25 mL) and brine (25 mL), dried over anhydrous MgSO$_4$ and concentrated under reduced pressure. The crude product is then chromatographed on a Flash 40M silica gel (90 g, 32–63 μm) cartridge, eluting with a gradient of EtOAc/heptane (15/85–25/75), and those fractions with an R$_f$=0.60 by TLC (EtOAc/hexane, 50/50) are pooled and concentrated to give 1.71 g (92%) of the title compound as a glassy solid. $^1$H NMR (400 MHz, CDCl$_3$) δ 7.42–7.32 (m, 5H), 7.24 (m, 1H), 7.11 (m, 1H), 6.91 (d, 1H), 6.67 (bs, 1H), 5.20 (s, 2H), 4.73 (s, 2H), 3.96 (t, 2H), 2.84 (t, 2H); MS (ESI+) for C$_{17}$H$_{17}$NO$_3$ m/z 284 (M+H)$^+$.

Step 2 Preparation of N-[[(5S)-3-(3,4-dihydro-1H-2-benzopyran-6-yl)-2-oxo-5-oxazolidinyl]methyl]acetamide A solution of phenylmethyl (3,4-dihydro-1H-2-benzopyran-6-yl)carbamate (Step 1, 1.60 g, 5.65 mmol) and MeOH (0.458 mL, 11.3 mmol) in dry DMF (5.6 mL) under N$_2$ is cooled in an ice bath and treated with LiOtBu (1M in THF, 16.95 mL, 16.95 mmol) dropwise over 2 mins. Then, the (1S)-2-(acetylamino)-1-(chloromethyl)ethyl acetate (2.19 g, 11.3 mmol) is added all at once, the cooling bath is removed and the mixture is stirred at ambient temperature for 2.75 days and is then diluted with H$_2$O (20 mL) and extracted with EtOAc (4×50 mL). The combined organic phase is washed with brine (25 mL), dried over MgSO$_4$ and concentrated under reduced pressure, and the residue is chromatographed on a Flash 40M silica gel (90 g, 32–63 μm) cartridge, eluting with a gradient of MeOH/CH$_2$Cl$_2$ (1/99–2/98). Those fractions with an R$_f$=0.23 by TLC (MeOH/CHCl$_3$, 5/95) are pooled and concentrated and the product triturated with EtOAc to give 828 mg (50%) of the title compound as a white solid, mp 142–145° C. [α]$^{25}_D$=−24° (c 1.01, DMSO).

Example 9

(+)-N-[[(5S)-3-(3,4-Dihydro-1H-2-benzopyran-6-yl)-2-oxo-5-oxazolidinyl]methyl]ethanethioamide

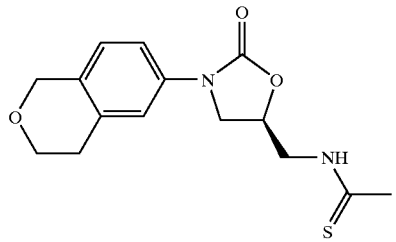

Following the general procedure of Example 5, and making non-critical variations but substituting (−)-N-[[(5S)-3-(3,4-dihydro-1H-2-benzopyran-6-yl)-2-oxo-5-oxazolidinyl]methyl]acetamide (Example 8) for methyl 6-[(5S)-5-[(acetylamino)methyl]-2-oxo-3-oxazolidinyl]-3,4-dihydro-2(1H)-isoquinolinecarboxylate and repurifying the final product by trituration and filtration from MeOH/Et$_2$O, the title compound (70%) is obtained as a white solid, mp 147–148° C. (decomp.). [α]$^{25}_D$=5° (c 0.93, MeOH).

Example 10

(−)-N-[[(5S)-3-(3,4-Dihydro-1H-2-benzothiopyran-6-yl)-2-oxo-5-oxazolidinyl]methyl]acetamide

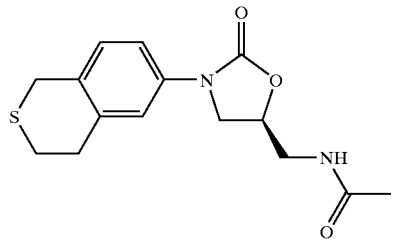

Step 1 Preparation of [2-[2-[(methylsulfonyl)oxy]ethyl]-4-nitrophenyl]methyl methanesulfonate A solution of 2-[2-(hydroxymethyl)-5-nitrophenyl]ethanol (2.95 g, 14.96 mmol, *J. Org. Chem.*, 1998, 63, 4116–4119) and triethylamine (6.26 mL, 44.9 mmol) in dry CH$_2$Cl$_2$ (60 mL) at 0° C. under N$_2$ is treated with methanesulfonyl chloride (2.89 mL, 37.4 mmol) dropwise and stirred at 0° C. for 30 mins. The mixture is then diluted with CH$_2$Cl$_2$ (40 mL), washed with 1M aqueous HCl (20 mL), saturated aqueous NaHCO$_3$ (20 mL) and brine (20 mL), dried over Na$_2$SO$_4$ and concentrated under reduced pressure to give the crude product which is chromatographed on a Flash 40M silica gel (90 g, 32–63 μm) cartridge, eluting with a gradient of EtOAc/heptane (30/70–70/30). Pooling and concentration of those fractions with an R$_f$=0.18 by TLC (EtOAc/hexane, 50/50) provides 4.58 g (87%) of the title compound as a white solid, mp 88–89° C.

Step 2 Preparation of 3,4-dihydro-6-nitro-1H-2-benzothiopyran

A mixture of [2-[2-[(methylsulfonyl)oxy]ethyl]-4-nitrophenyl]methyl methanesulfonate (Step 1, 4.56 g, 12.90 mmol) and potassium thioacetate (1.62 g, 14.20 mmol) in dry DMF (129 mL) under N$_2$ is stirred at ambient temperature for 3 hrs and is then diluted with H$_2$O (250 mL) and extracted with EtOAc (200 mL). The organic phase is washed with H$_2$O (2×100 mL) and brine (50 mL), dried over anhydrous MgSO₄ and concentrated under reduced pressure, and the residue is chromatographed on a Flash 40M silica gel (90 g, 32–63 μm) cartridge, eluting with a gradient of EtOAc/heptane (25/75–50/50). Pooling and concentration of those fractions with an $R_f$=0.44 by TLC (EtOAc/hexane, 50/50) provides 3.90 g (91%) of the benzyl thioacetate intermediate as a viscous oil [MS (ESI–) for $C_{12}H_{15}NO_6S_2$ m/z 332 (M–H)⁻]. The intermediate is taken up in 2M NH₃ in MeOH (250 mL), and the resulting solution is stirred at ambient temperature for 45 mins and then concentrated under reduced pressure. The residue is diluted with H₂O (75 mL) and extracted with Et₂O (75 mL), and the Et₂O layer is dried over anhydrous MgSO₄ and concentrated under reduced pressure to give 2.12 g (93%, 84% overall) of the title compound as a pale yellow solid, mp 60–63° C.

Step 3 Preparation of phenylmethyl (3,4-dihydro-1H-2-benzothiopyran-6-yl)carbamate A mixture of 3,4-dihydro-6-nitro-1H-2-benzothiopyran (Step 2, 2.10 g, 10.76 mmol) and SnCl₂.2H₂O (12.13 g, 53.78 mmol) in 95% EtOH (108 mL) is stirred at 70° C. under N₂ for 2 hrs. The resulting mixture is cooled to ambient temperature, added to ice H₂O (150 mL), adjusted to pH 8 with 5% aqueous NaOH and filtered through a pad of Celite. The filter pad is rinsed with EtOAc (3×100 mL), the layers in the filtrate are separated and the organic phase is dried over anhydrous MgSO₄ and concentrated under reduced pressure to give the 6-amino-3,4-dihydro-1H-2-benzothiopyran intermediate [MS (ESI+) for $C_9H_{11}NS$ m/z 166 (M+H)⁺] which is then dissolved in THF/H₂O (2:1, 108 mL) and treated with NaHCO₃ (1.81 g, 21.5 mmol) and benzyl chloroformate (1.69 mL, 11.8 mmol). The resulting mixture is stirred at ambient temperature for 30 mins and is then diluted with H₂O (50 mL) and extracted with EtOAc (75 mL). The organic phase is then washed with H₂O (50 mL) and brine (25 mL), dried over anhydrous MgSO₄ and concentrated under reduced pressure, and the crude product is chromatographed on a Flash 40M silica gel (90 g, 32–63 μm) cartridge, eluting with EtOAc/heptane (10/90). Pooling and concentration of those fractions with an $R_f$=0.64 by TLC (EtOAc/hexane, 50/50) provides 2.69 g (83%) of the title compound as a white solid, mp 116–118° C.

Step 4 Preparation of (–)-N-[[(5S)-3-(3,4-dihydro-1H-2-benzothiopyran-6-yl)-2-oxo-5-oxazolidinyl]methyl] acetamide A solution of phenylmethyl (3,4-dihydro-1H-2-benzothiopyran-6-yl)carbamate (Step 3, 2.55 g, 8.52 mmol), (1S)-2-(acetylamino)-1-(chloromethyl)ethyl acetate (*Tet. Lett.* 1996 37 (44) 7737–7740; 3.30 g, 17.03 mmol) and MeOH (0.690 mL, 17.03 mmol) in dry DMF (5.6 mL) under N₂ is treated with LiOtBu (1M in hexanes, 25.5 mL, 25.5 mmol) dropwise over 2 hrs, and the resulting biphasic mixture is stirred at ambient temperature for 32 hrs. The mixture is then cooled in an ice bath and treated with glacial HOAc (975 μL), and MeOH (10 mL) is added and the layers are separated. The hexane layer is reextracted with 20% H₂O/MeOH (20 mL), and the combined MeOH/H₂O phase is diluted with H₂O (40 mL) and extracted with EtOAc (3×40 mL). The combined EtOAc phase is then washed with H₂O (2×50 mL) and brine (25 mL), dried over MgSO₄ and concentrated under reduced pressure, and the residue is chromatographed on a Flash 40M silica gel (90 g, 32–63 μm) cartridge, eluting with a gradient of MeOH/CH₂Cl₂ (0.5/99.5–3/97). Those fractions with an $R_f$=0.27 by TLC (MeOH/CHCl₃, 5/95) are pooled and concentrated and the product triturated with EtOAc/Et₂O to give 1.90 g (73%) of the title compound as an off-white solid, mp 112–114° C. (decomp.). MS (ESI+) for $C_{15}H_{18}N_2O_3S$ m/z 307 (M+H)⁺; $[\alpha]^{25}_D$=–24° (c 0.80, DMSO).

Example 11

(+)-N-[[(5S)-3-(3,4-Dihydro-1H-2-benzothiopyran-6-yl)-2-oxo-5-oxazolidinyl]methyl]ethanethioamide

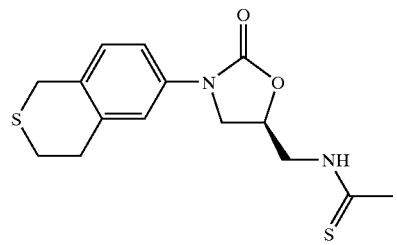

Following the general procedure of Example 5, and making non-critical variations but substituting (–)-N-[[(5S)-3-(3,4-(dihydro-1H-2-benzothiopyran-6-yl)-2-oxo-5-oxazolidinyl]methyl]acetamide (Example 10) for methyl 6-[(5S)-5-[(acetylamino)methyl]-2-oxo-3-oxazolidinyl]-3,4-dihydro-2(1H)-isoquinolinecarboxylate and repurifying the final product by recrystallization from CH₂Cl₂/Et₂O, the title compound (66%) is obtained as a white solid, mp 112–114° C. (decomp.). MS (ESI+) for $C_{15}H_{18}N_2O_2S_2$ m/z 323 (M+H)⁺; $[\alpha]^{25}_D$=5° (c 0.92, DMSO).

Example 12

(+)-N-[[(5S)-3-(3,4-Dihydro-2,2-dioxido-1H-2-benzothiopyran-6-yl)-2-oxo-5-oxazolidinyl]methyl] ethanethioamide

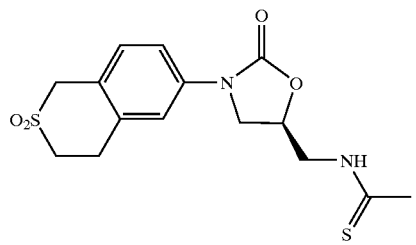

Step 1 Preparation of (–)-N-[[(5S)-3-(3,4-dihydro-2,2-dioxido-1H-2-benzothiopyran-6-yl)-2-oxo-5-oxazolidinyl] methyl]acetamide A solution of (–)-N-[[(5S)-3-(3,4-dihydro-1H-2-benzothiopyran-6-yl)-2-oxo-5-oxazolidinyl]methyl] acetamide (Example 10, 545 mg, 1.78 mmol) in acetone/H₂O (3/1, 36 mL) under N₂ is treated with N-methylmorpholine N-oxide (521 mg, 4.45 mmol) and OsO₄ (2.5 wt % in tBuOH, 1.11 mL, 5 mol %), and the resulting mixture is stirred at ambient temperature for 18 hrs and is then cooled in an ice bath and treated with half-saturated aqueous NaHSO₃ (50 mL). The mixture is extracted with CH₂Cl₂ (3×75 mL), and the combined organic phase is washed with brine (20 mL), dried over anhydrous Na₂SO₄ and concentrated under reduced pressure to give the crude product which is then chromatographed on a Flash 40S silica gel (40 g, 32–63 μm) cartridge, eluting with a gradient of MeOH/CH₂Cl₂ (1/99–4/96). Those fractions with an $R_f$=0.39 by TLC (MeOH/CHCl₃, 10/90) are pooled and concentrated and the product triturated with CH₂Cl₂/Et₂O to give 517 mg (86%) of the title compound as a white solid, mp 177–178° C. MS (ESI+) for $C_{15}H_{18}N_2O_5S$ m/z 339 (M+H)⁺; $[\alpha]^{25}_D$=–23° (c 0.97, DMSO).

27

Step 2 Preparation of (+)-N-[[(5S)-3-(3,4-dihydro-2,2-dioxido-1H-2-benzothiopyran-6-yl)-2-oxo-5-oxazolidinyl]methyl]ethanethioamide Following the general procedure of Example 5, and making non-critical variations but substituting (−)-N-[[(5S)-3-(3,4-dihydro-2,2-dioxido-1H-2-benzothiopyran-6-yl)-2-oxo-5-oxazolidinyl]methyl]acetamide (Step 1) for methyl 6-[(5S)-5-[(acetylamino)methyl]-2-oxo-3-oxazolidinyl]-3,4-dihydro-2(1H)-isoquinolinecarboxylate and repurifying the final product by trituration and filtration from MeOH/Et$_2$O, the title compound (75%) is obtained as a white solid, mp 187° C. (decomp.). MS (ESI+) for $C_{15}H_{18}N_2O_4S_2$ m/z 355 (M+H)$^+$; $[\alpha]^{25}_D$=4° (c 0.91, DMSO).

Example 13

(+)-N-[[(5S)-3-(3,4-Dihydro-1H-2-benzopyran-7-yl)-2-oxo-5-oxazolidinyl]methyl]ethanethioamide

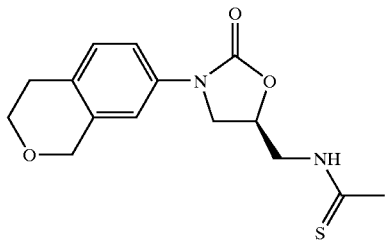

Step 1 Preparation of 2-[2-(hydroxymethyl)-4-nitrophenyl]ethanol

A solution of 4-nitrohomophthalic acid (313.12 g, 58.27 mmol, *J. Amer. Chem. Soc.*, 1969, 91, 2467) in dry THF (291 mL) under N$_2$ is treated with NaBH$_4$ (6.61 g, 174.8 mmol) portionwise over 15 mins. The resulting mixture is cooled in an ice bath and BF$_3$.Et$_2$O (22.15 mL, 174.8 mmol) is added dropwise over 35 mins. The cooling bath is removed, and the reaction mixture is stirred vigorously at ambient temperature for 18 hrs and is then cooled in an ice bath, quenched by the slow addition of 1N aqueous NaOH (233 mL, 4 equiv.) and stirred at ambient temperature for an additional 4 hrs. The THF is then removed under reduced pressure, the resulting precipitate is isolated by filtration, the filtrate is extracted with MeOH/CH$_2$Cl$_2$ (10/90, 3×150 mL), and the precipitate is combined with the organic extracts, diluted with additional MeOH/CH$_2$Cl$_2$ (10/90, 400 mL), dried over anhydrous Na$_2$SO$_4$, concentrated under reduced pressure and recrystallized from EtOAc/hexane to give 8.16 g (71%) of the title compound as a beige solid, mp 80–81° C. (decomp.).

Step 2 Preparation of 3,4-dihydro-7-nitro-1H-2-benzopyran

A solution of 2-[2-(hydroxymethyl)-4-nitrophenyl]ethanol (Step 1, 1.65 g, 8.37 mmol), succinimide (829 mg, 8.37 mmol) and triphenylphosphine (2.46 g, 9.37 mmol) in dry THF at 0° C. under N$_2$ is treated with diethyl azodicarboxylate (1.50 mL, 9.54 mmol) dropwise over 5 mins, and the resulting mixture is stirred at 0° C. for 4 hrs and then concentrated under reduced pressure. The residue is chromatographed on a Flash 40M silica gel (90 g, 32–63 μm) cartridge, eluting with EtOAc/heptane (10/90), and those fractions with an R$_f$=0.60 by TLC (EtOAc/hexane, 50/50) are pooled and concentrated to give 995 mg (66%) of the title compound as a white solid, mp 96–98° C.

Step 3 Preparation of phenylmethyl (3,4-dihydro-1H-2-benzopyran-7-yl)carbamate

Following the general procedure of Example 8, Step 1, and making non-critical variations but substituting 3,4-dihydro-7-nitro-1H-2-benzopyran (Step 2) for 3,4-dihydro-6-nitro-1H-2-benzopyran, the title compound is obtained (92%) as a white solid, mp 94–95° C.

Step 4 Preparation of (−)-N-[[(5S)-3-(3,4-dihydro-1H-2-benzopyran-7-yl)-2-oxo-5-oxazolidinyl]methyl]acetamide Following the general procedure of Example 10, Step 4, and making non-critical variations but substituting phenylmethyl (3,4-dihydro-1H-2-benzopyran-7-yl)carbamate (Step 3) for phenylmethyl (3,4-dihydro-1H-2-benzothiopyran-6-yl)carbamate, the title compound is obtained (63%) as a glassy solid. $^1$H NMR (400 MHz, CDCl$_3$) δ 8.21 (m, 1H), 7.34 (m, 1H), 7.19 (m, 1H), 7.13 (d, 1H), 4.69 (m, 1H), 4.65 (s, 2H), 4.07 (t, 1H), 3.85 (m, 2H), 3.69 (dd, 1H), 3.39 (m, 2H), 2.73 (m, 2H), 1.82 (s, 3H); MS (ESI+) for $C_{15}H_{18}N_2O_4$ m/z 291 (M+H)$^+$; $[\alpha]^{25}_D$=−22° (c 0.98 DMSO).

Step 5 Preparation of (+)-N-[[(5S)-3-(3,4-dihydro-1H-2-benzopyran-7-yl)-2-oxo-5-oxazolidinyl]methyl]acetamide Following the general procedure of Example 5, and making non-critical variations but substituting (−)-N-[[(5S)-3-(3,4-dihydro-1H-2-benzopyran-7-yl)-2-oxo-5-oxazolidinyl]methyl]acetamide (Step 4) for methyl 6-[(5S)-5-[(acetylamino)methyl]-2-oxo-3-oxazolidinyl]-3,4-dihydro-2(1H)-isoquinolinecarboxylate, using 0.7 mol-equivalents of Lawesson's reagent and repurifying the product by trituration with MeOH/Et$_2$O or recrystallization from EtOAc/hexane, the title compound is obtained (84%) as a white solid, mp 165° C. (decomp.). MS (ESI+) for $C_{15}H_{18}N_2O_3S$ m/z 307 (M+H)$^+$; $[\alpha]^{25}_D$=6° (c 0.96, DMSO).

Example 14

(−)-N-[[(5S)-3-(3,4-Dihydro-1H-2-benzothiopyran-7-yl)-2-oxo-5-oxazolidinyl]methyl]acetamide

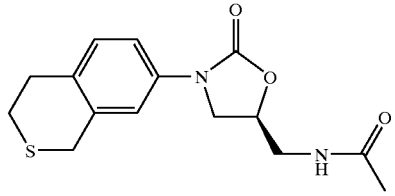

Step 1 Preparation of phenylmethyl 4-(2-hydroxyethyl)-3-(hydroxymethyl) phenylcarbamate A mixture 2-[2-(hydroxymethyl)-4-nitrophenyl]ethanol (Example 13, Step 1, 2.00 g, 10.14 mmol) and PtO$_2$ (10 mol %, 229 mg) in MeOH (50 mL) is degassed, shaken under 15 psi H$_2$ on a Parr hydrogenation apparatus for 3 hrs, and then the catalyst is removed by filtration through Celite. The filtrate is concentrated under reduced pressure to give the aniline intermediate which is then dissolved in THF/H$_2$O (2:1, 101 mL), cooled to 0° C. and treated with NaHCO$_3$ (1.70 g, 20.28 mmol) and benzyl chloroformate (1.59 mL, 11.15 mmol). The resulting mixture is stirred at 0° C. for 30 mins and is then diluted with EtOAc (50 mL), washed with H$_2$O (25 mL) and brine (25 mL), dried over anhydrous MgSO$_4$ and concentrated under reduced pressure. The crude product is then chromatographed on a Flash 40M silica gel (90 g, 32–63 μm) cartridge, eluting with a gradient of MeOH/CH$_2$Cl$_2$ (1/99–5/95), and those fractions with an R$_f$=0.50 by TLC (MeOH/CH$_2$Cl$_2$ (10/90)) are pooled and concentrated to give 2.84 g (93%) of the title compound as a white solid, mp 101–103° C.

Step 2 Preparation of phenylmethyl (3,4-dihydro-1H-2-benzothiopyran-7-yl)carbamate A solution of phenylmethyl 4-(2-hydroxyethyl)-3-(hydroxymethyl)phenylcarbamate (Step 1, 12.29 g, 40.78 mmol) and triethylamine (17.05 mL, 122.3 mmol) in dry CH₂Cl₂ (204 mL) at 0° C. under N₂ is treated with methanesulfonyl chloride (7.89 mL, 101.9 mmol) dropwise and stirred at 0° C. for 1 hr. The mixture is then diluted with CH₂Cl₂ (200 mL), washed with H₂O (200 mL) and brine (50 mL), dried over Na₂SO₄ and concentrated under reduced pressure to give the crude intermediate which is chromatographed on two Flash 40M silica gel (90 g, 32–63 μm) cartridge, eluting with a gradient of EtOAc/heptane (30/70–60/40). Pooling and concentration of those fractions with an $R_f$=0.22 by TLC (EtOAc/hexane, 50/50) provides 11.66 g (62%) of the bismesylate intermediate [MS (ESI+) for $C_{19}H_{23}NO_8S_2$ m/z 456 (M+H)$^+$] as a viscous oil. A mixture of this intermediate (10.58 g, 23.13 mmol) and anhydrous Na₂S (5.41 g, 69.39 mmol) in dry DMSO is then stirred under N₂ for 30 mins, diluted with Et₂O (200 mL) and ice H₂O (200 mL), and the layers are separated. The precipitate remaining in the reaction flask is dissolved in CH₂Cl₂ (50 mL) and washed with brine (20 mL), and the combined organic phase is dried over anhydrous Na₂SO₄ and concentrated under reduced pressure. The crude product is then chromatographed on a Flash 40M silica gel (90 g, 32–63 μm) cartridge, eluting with EtOAc/heptane (10/90), and those fractions with an $R_f$=0.61 by TLC (EtOAc/hexane, 25/75) are pooled and concentrated to give 3.39 g (49%, 30% overall) of the title compound as a white solid, mp 109–111° C.

Step 3 Preparation of (−)-N-[[(5S)-3-(3,4-dihydro-1H-2-benzothiopyran-7-yl)-2-oxo-5-oxazolidinyl]methyl]acetamide Following the general procedure of Example 10, Step 4, and making non-critical variations but substituting phenylmethyl (3,4-dihydro-1H-2-benzothiopyran-7-yl)carbamate (Step 2) for phenylmethyl (3,4-dihydro-1H-2-benzothiopyran-6-yl)carbamate, the title compound (70%) is obtained as a white solid, mp 139–140° C. $[\alpha]^{25}_D$=−24° (c 0.98, DMSO).

Example 15

(+)-N-[[(5S)-3-(3,4-Dihydro-1H-2-benzothiopyran-7-yl)-2-oxo-5-oxazolidinyl]methyl]ethanethioamide

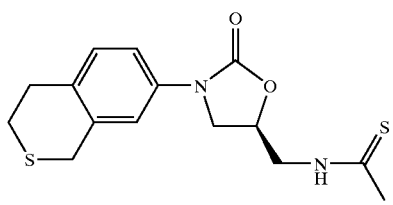

Following the general procedure of Example 5, and making non-critical variations but substituting (−)-N-[[(5S)-3-(3,4-dihydro-1H-2-benzothiopyran-7-yl)-2-oxo-5-oxazolidinyl]methyl]acetamide (Example 14) for methyl 6-[(5S)-5-[(acetylamino)methyl]-2-oxo-3-oxazolidinyl]-3,4-dihydro-2(1H)-isoquinolinecarboxylate, using 0.7 mol-equivalents of Lawesson's reagent and repurifying the final product by trituration and filtration from MeOH/Et₂O, the title compound (72%) is obtained as a white solid, mp 172–173° C. (decomp.). $[\alpha]^{25}_D$=4° (c 0.93, DMSO).

Example 16

(+)-N-[[(5S)-3-(3,4-Dihydro-2,2-dioxido-1H-2-benzothiopyran-7-yl)-2-oxo-5-oxazolidinyl]methyl]ethanethioamide

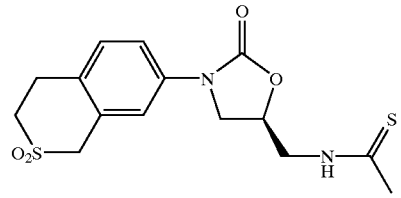

Step 1 Preparation of (−)-N-[[(5S)-3-(3,4-dihydro-2,2-dioxido-1H-2-benzothiopyran-7-yl)-2-oxo-5-oxazolidinyl]methyl]acetamide Following the general procedure of Example 12, Step 1, and making non-critical variations but substituting (−)-N-[[(5S)-3-(3,4-dihydro-1H-2-benzothiopyran-7-yl)-2-oxo-5-oxazolidinyl]methyl]acetamide (Example 14) for (−)-N-[[(5S)-3-(3,4-dihydro-1H-2-benzothiopyran-6-yl)-2-oxo-5-oxazolidinyl]methyl]acetamide, the title compound (95%) is obtained as a white solid, mp 177–179° C. $[\alpha]^{25}_D$=−22° (c 1.02, DMSO).

Step 2 Preparation of (+)-N-[[(5S)-3-(3,4-dihydro-2,2-dioxido-1H-2-benzothiopyran-7-yl)-2-oxo-5-oxazolidinyl]methyl]ethanethioamide Following the general procedure of Example 5, but substituting (−)-N-[[(5S)-3-(3,4-dihydro-2,2-dioxido-1H-2-benzothiopyran-7-yl)-2-oxo-5-oxazolidinyl]methyl]acetamide (Step 1) for methyl 6-[(5S)-5-[(acetylamino)methyl]-2-oxo-3-oxazolidinyl]-3,4-dihydro-2(1H)-isoquinolinecarboxylate, using 0.7 mol-equivalents of Lawesson's reagent and repurifying the final product by recrystallization from (10% MeOH/CH₂Cl₂)/Et₂O, the title compound (84%) is obtained as a white solid, mp 184–185° C. (decomp.). $[\alpha]^{25}_D$=4° (c 0.90, DMSO).

Example 17

N-[[(5S)-3-(3,4-Dihydro-2-oxido-1H-2-benzothiopyran-7-yl)-2-oxo-5-oxazolidinyl]methyl]acetamide

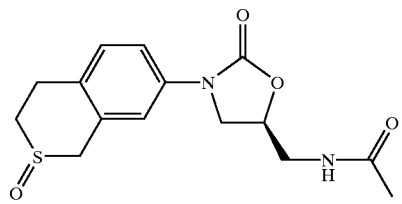

A solution of NaIO₄ (220 mg, 1.03 mmol) in H₂O (4.1 mL) is treated with a solution of (−)-N-[[(5S)-3-(3,4-dihydro-1H-2-benzothiopyran-7-yl)-2-oxo-5-oxazolidinyl]methyl]acetamide (Example 14, 300 mg, 0.979 mmol) in MeOH (20 mL) over approximately 1 min, and the resulting mixture is stirred at ambient temperature for 18 hrs. The mixture is then diluted with brine (25 mL) and extracted with 10% MeOH/CH₂Cl₂ (4×25 mL), and the combined organic phase is dried over anhydrous Na₂SO₄ and concentrated under reduced pressure. The residue is chromatographed on a Flash 40S silica gel (40 g, 32–63 μm) cartridge, eluting with a gradient of MeOH/CH₂Cl₂ (2/98–8/92), and those fractions with an $R_f$=0.20 by TLC (MeOH/CHCl$_3$, 10/90) are pooled and concentrated to give 293 mg (93%) of the title compound (mixture of diastereomers) as an amorphous, white solid.
$^1$H NMR (400 MHz, DMSO-d$_6$) δ 8.22 (m, 1H), 7.43 (m, 1H), 7.34 (m, 1H), 7.23 (d, 1H), 4.71 (m, 1H), 4.10–3.95 (m, 3H), 3.72 (m, 1H), 3.40 (m, 2H), 3.16 (m, 2H), 2.88 (m, 2H), 1.82 (s, 3H); MS (ESI+) for C$_{15}$H$_{18}$N$_2$O$_4$S m/z 323 (M+H)$^+$.

Example 18

(+)-N-[[(5S)-3-[2-Formyl-1,2,3,4-tetrahydro-7-isoquinolinyl]-2-oxo-5-oxazolidinyl]methyl] ethanethioamide Step 1 Preparation of [2-[2-[(methylsulfonyl)oxy]ethyl]-5-nitrophenyl]methyl methanesulfonate Following the general procedure of Example 10, Step 1, and making non-critical variations but substituting 2-[2-(hydroxymethyl)-4-nitrophenyl]ethanol (Example 13, Step 1) for 2-[2-(hydroxymethyl)-5-nitrophenyl]ethanol, the title compound (85%) is obtained as a white solid, mp 83–85° C.

Step 2 Preparation of N-benzyl-7-nitro-1,2,3,4-tetrahydroisoquinoline

A solution of [2-[2-[(methylsulfonyl)oxy]ethyl]-5-nitrophenyl]methyl methanesulfonate (Step 1, 1.75 g, 4.95 mmol) in CH$_2$Cl$_2$ (25 mL) under N$_2$ is treated with benzylamine (2.70 mL, 24.75 mmol), and the resulting mixture is stirred at ambient temperature for 24 hrs and then washed with water (20 mL) and brine (10 mL), dried over anhydrous Na$_2$SO$_4$ and concentrated under reduced pressure. The crude product is then chromatographed on a Flash 40M silica gel (90 g, 32–63 μm) cartridge, eluting with EtOAc/heptane (10/90), and those fractions with an $R_f$=0.32 by TLC (EtOAc/hexane, 25/75) are pooled and concentrated to give 1.33 g (100%) of the title compound as an orange solid, mp 85–86° C.

Step 3 Preparation of phenylmethyl 3,4-dihydro-7-[[(phenylmethoxy)carbonyl]amino]-2(1H)-isoquinolinecarboxylate Following the general procedure of Example 1, Step 2, and making non-critical variations but substituting N-benzyl-7-nitro-1,2,3,4-tetrahydroisoquinoline (Step 2) for N-benzyl-6-nitro-1,2,3,4-tetrahydroisoquinoline, the title compound (77%) is obtained as a white solid, mp 113–115° C.

Step 4 Preparation of (–)-phenylmethyl 7-[(5S)-5-[[[(1,1-dimethylethoxy)carbonyl]amino]methyl]-2-oxo-3-oxazolidinyl]-3,4-dihydro-2(1H)-isoquinolinecarboxylate A solution of phenylmethyl 3,4-dihydro-7-[[(phenylmethoxy)carbonyl]amino]-2(1H)-isoquinolinecarboxylate (Step 3, 5.12 g, 12.29 mmol) and tert-butyl (2S)-3-chloro-2-hydroxypropylcarbamate (which can be prepared according to U.S. patent application, serial No. 60/241122, 3.22 g, 15.36 mmol) in dry DMF (5.6 mL) at 0° C. under N$_2$ is treated with LiOtBu (1M in THF, 29.5 mL, 29.5 mmol) dropwise over 5 mins. The cooling bath is removed, and the resulting mixture is stirred at ambient temperature for 18 hrs, quenched with saturated aqueous NH$_4$Cl (25 mL), diluted with H$_2$O (25 mL) and extracted with EtOAc (50 mL). The EtOAc phase is then washed with H$_2$O (2×50 mL) and brine (25 mL), dried over MgSO$_4$ and concentrated under reduced pressure, and the residue is chromatographed on a Flash 40M silica gel (90 g, 32–63 μm) cartridge, eluting with a gradient of EtOAc/heptane (25/75–50/50). Those fractions with an $R_f$=0.20 by TLC (EtOAc/hexane, 50/50) are pooled and concentrated to give 4.69 g (80%) of the title compound as a white solid, mp 135–137° C. [α]$^{25}_D$=–27° (c 1.00, DMSO).

Step 5 Preparation of (–)-1,1-dimethylethyl [[(5S)-2-oxo-3-[1,2,3,4-tetrahydro-7-isoquinolinyl]-5-oxazolidinyl]methyl] carbamate Following the general procedure of Example 6, Step 2, and making non-critical variations but substituting (–)-phenylmethyl 7-[(5S)-5-[[[(1,1-dimethylethoxy)carbonyl]amino]methyl]-2-oxo-3-oxazolidinyl]-3,4-dihydro-2(1H)-isoquinolinecarboxylate (Step 4) for (–)-phenylmethyl 6-[(5S)-5-[[[(1,1-dimethylethoxy)carbonyl]amino]methyl]-2-oxo-3-oxazolidinyl]-3,4-dihydro-2(1H)-isoquinolinecarboxylate, the title compound (100%) is obtained as an amorphous, white solid which is used without further purification. $^1$H NMR (400 MHz, DMSO-d$_6$) δ 7.29 (m, 1H), 7.17 (m, 2H), 7.06 (d, 1H), 4.65 (m, 1H), 4.05 (t, 1H), 3.85 (s, 2H), 3.74 (dd, 1H), 3.25 (m, 2H), 2.95 (m, 2H), 2.66 (m, 2H), 1.36 (s, 9H); MS (ESI+) for C$_{18}$H$_{25}$N$_3$O$_4$ m/z 348 (M+H)$^+$; [α]$^{25}_D$=–33° (c 0.93, DMSO).

Step 6 Preparation of (–)-1,1-dimethylethyl [[(5S)-2-oxo-3-[2-formyl-1,2,3,4-tetrahydro-7-isoquinolinyl]-5-oxazolidinyl]methyl]carbamate Following the general procedure of Example 6, Step 3, and making non-critical variations but substituting 1,1-dimethylethyl [[(5S)-2-oxo-3-[1,2,3,4-tetrahydro-7-isoquinolinyl]-5-oxazolidinyl]methyl]carbamate (Step 5) for 1,1-dimethylethyl [[(5S)-2-oxo-3-[1,2,3,4-tetrahydro-6-isoquinolinyl]-5-oxazolidinyl]methyl]carbamate, the title compound (97%) is obtained as an amorphous, white solid. $^1$H NMR (400 MHz, DMSO-d$_6$) δ (mixture of rotamers A and B) 8.21 (s, 1H$_B$), 8.16 (s, 1H$_A$), 7.42–7.29 (m, 2H$_A$+2H$_B$), 7.16 (m 2H$_A$+2H$_B$). 4.68 (m, 1H$_A$+1H$_B$), 4.57 (s, 2H$_B$), 4.53 (s, 2H$_A$), 4.08 (t, 1H$_A$+1H$_B$), 3.76 (m, 1H$_A$+1H$_B$), 3.63 (m, 2H$_A$+2H$_B$), 3.26 (m, 2H$_A$+2H$_B$), 2.80 (m, 2H$_A$), 2.73 (m, 2H$_B$), 1.36 (s, 9H$_A$+9H$_B$); MS (ESI+) for C$_{19}$H$_{25}$N$_3$O$_5$ m/z 375 (M+H)$^+$; [α]$^{25}_D$=–32° (c 0.97, DMSO).

Step 7 Preparation of (+)-N-[[(5S)-3-[2-formyl-1,2,3,4-tetrahydro-7-isoquinolinyl]-2-oxo-5-oxazolidinyl]methyl] ethanethioamide A solution of 1,1-dimethylethyl [[(5S)-2-oxo-3-[2-formyl-1,2,3,4-tetrahydro-7-isoquinolinyl]-5-oxazolidinyl] methyl]carbamate (Step 6, 910 mg, 2.42 mmol) in a minimum of MeOH at 0° C. is treated with 4N HCl in dioxane (12.1 mL), and the resulting mixture is stirred at 0° C. for 15 mins and then concentrated down several times from CH$_2$Cl$_2$ to give the deprotected aminomethyl oxazolidinone intermediate as its hydrochloride salt [MS (ESI+) for C$_{14}$H$_{17}$N$_3$O$_3$ m/z 276 (M+H)$^+$] which was used without further purification. A solution of this intermediate (370 mg, 1.19 mmol) and triethylamine (497 μL, 3.57 mmol) in dry CH$_2$Cl$_2$ (12 mL) under N$_2$ is treated with ethyl dithioacetate (273 μL, 2.38 mmol). The homogeneous mixture is stirred for 5 hrs and is then diluted with CH$_2$Cl$_2$ (10 mL), washed with H$_2$O (10 mL) and brine (10 mL), dried over Na$_2$SO$_4$ and concentrated under reduced pressure. The crude product

Example 19

(+)-N-[[(5S)-3-[2-[(Hydroxy)acetyl]-1,2,3,4-tetrahydro-7-isoquinolinyl]-2-oxo-5-oxazolidinyl]methyl]ethanethioamide

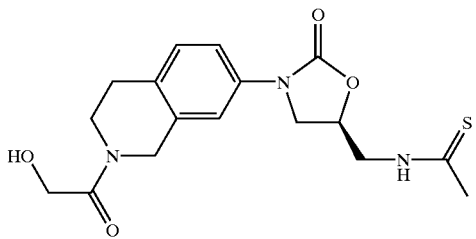

Step 1 Preparation of (−)-1,1-dimethylethyl [[(5S)-2-oxo-3-[1,2,3,4-tetrahydro-2-[(phenylmethoxy)acetyl]-7-isoquinolinyl]-5-oxazolidinyl]methyl]carbamate Following the general procedure of Example 7, Step 1, and making non-critical variations but substituting 1,1-dimethylethyl [[(5S)-2-oxo-3-[1,2,3,4-tetrahydro-7-isoquinolinyl]-5-oxazolidinyl]methyl]carbamate (Example 18, Step 5) for 1,1-dimethylethyl [[(5S)-2-oxo-3-[1,2,3,4-tetrahydro-6-isoquinolinyl]-5-oxazolidinyl]methyl]carbamate, the product (89%) is obtained as an amorphous, white solid. $^1$H NMR (400 MHz, DMSO-$d_6$) δ (mixture of rotamers A and B) 7.43–7.27 (m, 7H$_A$+7H$_B$), 7.17 (m, 2H$_A$+2H$_B$), 4.67 (m, 1H$_A$+1H$_B$), 4.60–4.51 (m, 4H$_A$+4H$_B$), 4.28 (s, 2H$_A$+2H$_B$), 4.08 (m, 1H$_A$+1H$_B$), 3.76 (m, 1H$_A$+3H$_B$), 3.65 (m, 2H$_A$+2H$_B$), 3.26 (m, 2H$_A$+2H$_B$), 2.80 (m, 2H$_A$), 2.74 (m, 2H$_B$), 1.36 (s, 9H$_A$+9H$_B$); MS (ESI+) for $C_{27}H_{33}N_3O_6$ m/z 496 (M+H)$^+$; [α]$^{25}_D$=−27° (c 1.01, DMSO).

Step 2 Preparation of (+)-N-[[(5S)-3-[2-[(hydroxy)acetyl]-1,2,3,4-tetrahydro-7-isoquinolinyl]-2-oxo-5-oxazolidinyl]methyl]ethanethioamide A solution of (−)-1,1-dimethylethyl [[(5S)-2-oxo-3-[1,2,3,4-tetrahydro-2-[(phenylmethoxy)acetyl]-7-isoquinolinyl]-5-oxazolidinyl]methyl]carbamate (Step 1, 1.32 g, 2.66 mmol) in a minimum of MeOH at 0° C. is treated with 4N HCl in dioxane (13.3 mL), and the resulting mixture is stirred at 0° C. for 15 mins and then concentrated down several times from CH$_2$Cl$_2$ to give the deprotected aminomethyl oxazolidinone intermediate as its hydrochloride salt [MS (ESI+) for $C_{22}H_{25}N_3O_4$ m/z 396 (M+H)$^+$] which is used without further purification. A solution of this intermediate in MeOH (53 mL) is added to a Parr bottle containing 10% Pd-on-C (570 mg, 20 mol %) under N$_2$, and the mixture is shaken under 30 psi H$_2$ for approximately 6 hrs and then filtered through Celite to remove the catalyst and concentrated under reduced pressure to give the debenzylated intermediate [894 mg, 98%, MS (ESI+) for $C_{15}H_{19}N_3O_4$ m/z 306 (M+H)$^+$] which is also used without further purification. A solution of this intermediate (470 mg, 1.37 mmol) and triethylamine (573 μL, 4.11 mmol) in dry CH$_2$Cl$_2$ (13.7 mL) under N$_2$ is treated with ethyl dithioacetate (314 μL, 2.74 mmol). The homogeneous mixture is stirred for 15 hrs and is then diluted with CH$_2$Cl$_2$ (10 mL), washed with H$_2$O (10 mL) and brine (10 mL), dried over Na$_2$SO$_4$ and concentrated under reduced pressure. The crude product is chromatographed on a Flash 40S silica gel (40 g, 32–63 μm) cartridge, eluting with a gradient of MeOH/CH$_2$Cl$_2$ (2/98–4/96), and those fractions with an R$_f$=0.41 by TLC (MeOH/CHCl$_3$, 10/90) are pooled and concentrated and the product triturated and filtered from CH$_2$Cl$_2$/Et$_2$O to give 260 mg (52%) of the title compound as a white solid, mp 158–160° C. (decomp). [α]$^{25}_D$=4° (c 0.96, DMSO).

Example 20

N-{[(5S)-3-(1-Formyl-2,3,4,5-tetrahydro-1H-1-benzazepin-7-yl)-2-oxo-1,3-oxazolidin-5-yl]methyl}acetamide

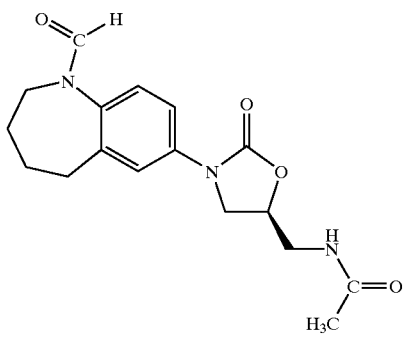

Step 1 Preparation of 2,3,4,5-tetrahydro-1H-1-benzazepin-2-one

A solution of sodium azide (25 g, 370 mmol) in water (13 mL) and chloroform (160 mL) is cooled to 0° C. and treated dropwise with concentrated sulfuric acid (11 mL). Stirring is continued for 30 min and the layers separated. The organic layer is dried over anhydrous sodium sulfate, filtered, and α-tetralone (20 g, 137 mmol) is added in one portion with stirring. The resulting solution is heated at 40° C. and concentrated sulfuric acid (38 mL) is added dropwise to maintain the internal temperature at 40–45° C. and stirring continued for 1 h, then cooled to 20° C. and poured into a sepratory funnel. The bottom layer is added dropwise with stirring to ise water (900 mL). The resulting solids are collected by filtration, and dried in vacuo at 40° C. to give 19.7 g of an off-white solid (89%), mp 139–140° C.; MS (ESI+) m/z 162 (M+H).

Step 2 Preparation of 7-nitro-2,3,4,5-tetrahydro-1H-1-benzazepine.

The previous benzazepinone (5.0 g, 31 mmol) in concentrated sulfuric acid (25 mL) at 0–5° C. is treated dropwise with fuming nitric acid (2.0 mL) in concentrated sulfuric acid (4 mL) and stirred for 30 min. The mixture is poured into ice water (150 mL) and the resulting solids collected by filtration and then chromatographed on silica gel with 20–30% ethyl acetate in dichloromethane to give 1.3 g of a mixture of the 7- and 8-nitro isomers. The regioisomers are dissolved in THF (20 mL) and treated dropwise with 1 M borane-THF (20 mL) and then heated at 60° C. for 3 h, cooled, and quenched with 1N hydrochloric acid (20 mL). The resulting mixture is made basic with saturated aqueous sodium bicarbonate and then extracted with ethyl acetate. The organic layers are washed with brine, dried over anhydrous sodium sulfate, and chromatographed on silica gel with 20% ethyl acetate in heptane to give 460 mg (45%) of the title compound as a yellow foam. Anal. Calcd for $C_{10}H_{12}N_2O_2$: C, 62.49; H, 6.29; N, 14.57. Found: C, 62.15; H, 6.17; N, 14.54; MS (ESI+) m/z 193 (M+H).

Step 3 Preparation of benzyl 7-(benzylcarboxyamino)-2,3,4,5-tetrahydro-1H-1-benzazepine-1-carboxylate The nitrobenzazepinone (450 mg, 2.3 mmol), hydrazine (300 μL), and 10% palladium on carbon (50 mg) in absolute ethanol (10 mL) is heated at 60° C. for 1 h, cooled, filtered through celite, and concentrated in vacuo to give a white solid (430 mg). The solid is dissolved in acetone (10 mL), diluted with water (5 mL), and treated with sodium bicarbonate (1.00 g, 12 mmol) and benzyl chloroformate (750 μL, 5.3 mmol). The mixture is stirred at room temperature for 1 h, diluted with ethyl acetate (50 mL) which is washed with water and brine, dried over anhydrous sodium sulfate, filtered, concentrated, and chromatographed on silica gel with 20% ethyl acetate in heptane to give 885 mg of the title compound (83%) as a white foam. Anal. Calcd for $C_{26}H_{26}N_2O_4$: C, 72.54; H, 6.09; N, 6.51.
Found: C, 72.53; H, 6.18; N, 6.50; MS (ESI+) m/z 431 (M+H).

Step 4 Preparation of phenylmethyl 7-[(5R)-(5-hydroxymethyl)-2-oxo-3-oxazolidinyl]-2,3,4,5-tetrahydro-1H-benzazepine-1-carboxylate.

The previous compound (850 mg, 2.0 mmol) is dissolved in THF (15 mL) cooled to −70° C. and treated dropwise with n-butyllithium (1.22 mL, 2.0 mmol) then stirred for 30 min before adding (R)-(−)-glycidyl butyrate (310 μL, 2.1 mmol). The mixture is stirred at room temperature overnight, diluted with water, extracted with dichloromethane which is dried over anhydrous sodium sulfate, filtered, concentrated, and chromatographed on silica gel with 20% ethyl acetate in dichloromethane to give 564 mg (72%) of a white foam. HRMS (FAB) calcd for $C_{22}H_{24}N_2O_5$+H: 397.1763, found 397.1796; Anal. Calcd for $C_{22}H_{24}N_2O_5$: C, 66.65; H, 6.10; N, 7.07. Found: C, 66.35; H, 6.34; N, 6.91.

Step 5 Preparation of phenylmethyl 7-[(5R)-(5-acetylamino)-2-oxo-3-oxazolidinyl]-2,3,4,5-tetrahydro-1H-benzazepine-1-carboxylate.

The previous compound (540 mg, 1.4 mmol), 3-nitrobenzenesulfonyl chloride (340 mg, 1.5 mmol) and triethylamine (400 μL, 2.9 mmol) are combined in dichloromethane (20 mL) and stirred over night at room temperature. The mixture is washed with water and brine, dried over anhydrous sodium sulfate, filtered, and concentrated. The resulting oil is dissolved in THF (10 mL), methanol (6 mL), and ammonium hydroxide (16 mL) in a sealed tube and heated at 80° C. overnight. After cooling, the solution is diluted with water, extracted with dichloromethane, dried over anhydrous sodium sulfate, filtered, and concentrated. The resulting oil is dissolved in dichloromethane (10 mL), treated with acetic anhydride (260 μL) and stirred at room temperature until the starting material is consumed as determined by TLC. The mixture is then concentrated in vacuo and chromatographed on silica gel with 40% ethyl acetate in dichloromethane to give 530 mg (89%) of the title compound as a white foam. HRMS (FAB) calcd for $C_{24}H_{27}N_3O_5$+H1 438.2029, found 438.2032. Anal. Calcd for $C_{24}H_{27}N_3O_5$: C, 65.89; H, 6.22; N, 9.60. Found: C, 65.19; H, 6.53; N, 9.47.

Step 6 Preparation of N-{[(5S)-3-(2,3,4,5-tetrahydro-1H-1-benzazepin-7-yl)-2-oxo-1,3-oxazolidin-5-yl]methyl}acetamide.

The previous compound (530 mg, 1.2 mmol) and 10% palladium on carbon (50 mg) are hydrogenated in methanol (30 mL) at 30 psi for 18 h, filtered through celite, concentrated, and chromatographed on silica gel with 40–80% ethyl acetate in dichloromethane to give 315 mg (86%) of the title compound as a white solid. Specific Rotation $[\alpha]^{25}_D$=−21 (c 0.60, DMSO). Anal. Calcd for $C_{16}H_{21}N_3O_3$: C, 63.35; H, 6.98; N, 13.85. Found: C, 63.23; H, 7.03; N, 13.83.

Step 7 Preparation of N-{[(5S)-3-(1-formyl-2,3,4,5-tetrahydro-1H-1-benzazepin-7-yl)-2-oxo-1,3-oxazolidin-5-yl]methyl}acetamide.

Acetic anhydride (162 μL, 1.7 mmol) is added to 98% formic acid (70 μL, 2.0 mmol) and heated at 60° C. for 1 h, cooled, and then diluted with THF (1 mL). The previous compound (20 mg, 0.67 mmol) in THF (5 mL) is added to the above mixture and then stirred at room temperature for 1 h. After concentrating in vacuo, the crude product is chromatographed on silsica gel with 3% methanol in dichloromethane to give 170 mg (78%) of the title compound as a white solid. Specific Rotation $[\alpha]^{25}_D$=−23° (c 0.85, DMSO).

Anal. Calcd for $C_{17}H_{21}N_3O_4$: C, 61.62; H, 6.39; N, 12.68. Found: C, 61.41; H, 6.50; N, 12.41.

Example 21

N-{[(5S)-3-(1-Formyl-2,3,4,5-tetrahydro-1H-1-benzazepin-7-yl)-2-oxo-1,3-oxazolidin-5-yl]methyl}ethanethioamide

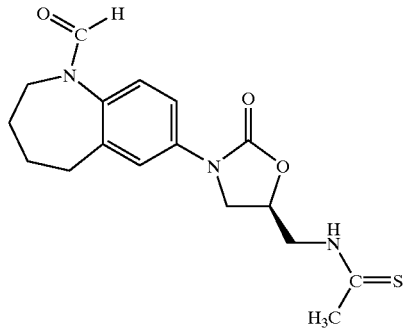

Step 1 Preparation of N-{[(5S)-3-(2,3,4,5-tetrahydro-1H-1-benzazepin-7-yl)-2-oxo-1,3-oxazolidin-5-yl]methyl}ethanethioamide.

The compound from Example 20, Step 6 (200 mg, 0.61 mmol) and Lawesson's Reagent are combined in dioxane (10 mL) and heated at reflux for 18 h. The mixture is cooled, silica gel (2 g) is added and the volitiles removed in vacuo. The resulting material is chromatographed on silica gel with 20–40% ethyl acetate in dichloromethane to give 190 mg (90%) of the title compound. HRMS (FAB) calcd for $C_{16}H_{21}N_3O_2S$+H1 320.1432, found 320.1439.

Step 2 Preparation of N-{[(5S)-3-(1-formyl-2,3,4,5-tetrahydro-1H-1-benzazepin-7-yl)-2-oxo-1,3-oxazolidin-5-yl]methyl}ethanethioamide.

Following the procedure from Example 20 Step 7, the previous compound (150 mg, 0.47 mmol) is converted to the title compound (83 mg, 51%). Specific Rotation $[\alpha]^{25}_D$=7° (c 0.54, DMSO). Anal. Calcd for $C_{17}H_{21}N_3O_3S$: C, 58.77; H, 6.09; N, 12.09; Found: C, 58.41; H, 6.53; N, 11.86.

Example 22

Benzyl 7-{(5S)-5-[acetylamino]-2-oxo-1,3-oxazolidin-3-yl}-1,2,4,5-tetrahydro-3H-3-benzazepine-3-carboxylate

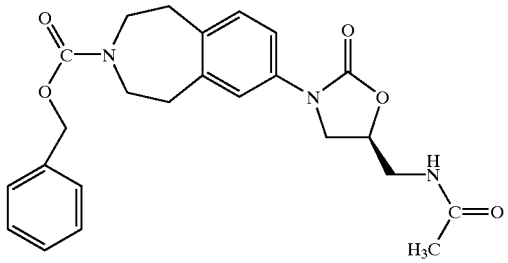

Step 1 Preparation of methyl 7-nitro-2,3,4,5-tetrahydro-1H-3-benzazepine-3-carboxylate Methyl chloroformate (120 mL, 1.53 mol) is added dropwise to 2,3,4,5-tetrahydro-1H-3-benzazepine (*J. Heterocyclic Chem.*, 1971, 779–783) in THF (1 L), water (1 L), and sodium bicarbonate (206 g, 2.46 mmol) at 0° C. The mixture is stirred at room temperature for 4 h, extracted with dichloromethane which is washed with 1 N hydrochloric acid, water, 1 N sodium hydroxide, and brine then dried over anhydrous sodium sulfate, filtered, and concentrated to a amber oil which slowly crystallized. The solid is dissolved in concentrated sulfuric acid (500 mL), cooled to −10° C., and treated dropwise with a solution of ammonium nitrate (82 g, 1.03 mol) in concentrated sulfuric acid (500 mL). The temperature is maintained at 0–5° C. for 3 h then poured onto ice and extracted with dichloromethane. The organic layer is washed with water, saturated aqueous sodium bicarbonate, dried over anhydrous sodium sulfate, filtered, concentrated, and chromatographed on a Chiralcel® AD column with 20% isopropanol in heptane to give 161 g (66%) of the title compound.

Anal. Calcd for $C_{10}H_8BrNO_2$: C, 47.27; H, 3.17; N, 5.51; Found: C, 47.14; H, 3.20; N, 5.54.

Step 2 Preparation of methyl 7-amino-2,3,4,5-tetrahydro-1H-3-benzazepine-3-carboxylate A mixture of the compound from Step 1 (50 g, 200 mmol) and 10% palladium on carbon (2.5 g) in ethanol (800 mL) is hydrogenated with shaking at 20 psi. Methyl t-butyl ether is added and the mixture filtered through celite and concentrated to give 44 g (100%) of the title compound as a white solid, mp 100–104° C.

Step 3 Preparation of phenylmethyl 7-(phenylmethylcarboxyamino)-2,3,4,5-tetrahydro-1H-3-benzazepine-3-carboxylate.

The amine from the previous step (1.0 g, 4.5 mmol) and potassium hydroxide (1.5 g, 27 mmol) in ethanol (40 mL) and water (10 mL) is heated at 90° C. overnight. Additional potassium hydroxide (1.5 g) is added and reflux continued for 24 h. The reaction is cooled, diluted with water, extracted with dichloromethane, and the organic layers concentrated. The resulting oil is dissolved in 4:1 acetone/water (50 mL), treated with sodium bicarbonate (2.0 g, 24 mmol) and benzyl chloroformate (1.6 mL, 11 mmol), stirred overnight at room temperature, then diluted with ethyl acetate and washed with water and brine, dried over anhydrous sodium sulfate, filtered, concentrated, and chromatographed on silica gel with 20% ethyl acetate in heptane to give 1.59 g (81%) of the title compound as a yellow oil which slowly solidified. MS (ESI+) m/z 431 (M+H).

Step 4 Preparation of benzyl 7-{(5S)-5-[hydroxymethyl]-2-oxo-1,3-oxazolidin-3-yl}-1,2,4,5-tetrahydro-3H-3-benzazepine-3-carboxylate.

Following the procedure described in Example 20 Step 4, using the previous compound (1.5 g, 3.5 mmol) as starting material, the title compound (690 mg, 50%) is obtained as a white solid. Specific Rotation $[\alpha]^{25}_D=-32°$ (c 0.47, DMSO). Anal. Calcd for $C_{22}H_{24}N_2O_5$: C, 66.65; H, 6.10; N, 7.07. Found: C, 66.62; H, 6.12; N, 7.02.

Step 5 Preparation of benzyl 7-{(5S)-5-[acetylamino]-2-oxo-1,3-oxazolidin-3-yl}-1,2,4,5-tetrahydro-3H-3-benzazepine-3-carboxylate.

Following the procedure described in Example 20 Step 5, using the previous compound (650 mg, 1.6 mmol) as starting material, the title compound (600 mg, 83%) is obtained as a white solid. Specific $[\alpha]^{25}_D=-17°$ (c 0.56, DMSO). Anal. Calcd for $C_{24}H_{27}N_3O_5$: C, 65.89; H, 6.22; N, 9.60. Found: C, 65.60; H, 6.17; N, 9.44.

Example 23

N-{[(5S)-3-(3-Formyl-1,2,4,5-tetrahydro-1H-3-benzazepin-7-yl)-2-oxo-1,3-oxazolidin-5-yl]methyl}acetamide

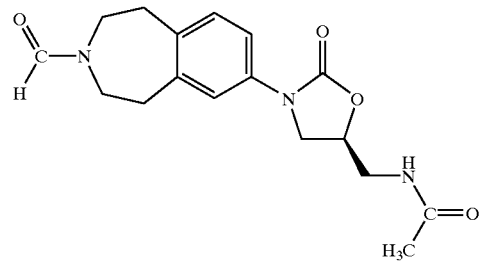

Step 1 Preparation of 7-{(5S)-5-[acetylamino]-2-oxo-1,3-oxazolidin-3-yl}-1,2,4,5-tetrahydro-3H-3-benzazepine.

Following the procedure described in Example 20 Step 6, using the material from Example 20 Step 5 (500 mg, 1.1 mmol) as starting material, the title compound (350 mg, 100%) is obtained as a white solid. MS (ESI+) m/z 304 (M+H).

Step 2 Preparation of N-{[(5S)-3-(3-formyl-1,2,4,5-tetrahydro-1H-3-benzazepin-7-yl)-2-oxo-1,3-oxazolidin-5-yl]methyl}acetamide.

Following the procedure described in Example 20 Step 7, using the previous compound (100 mg, 0.33 mmol) as starting material, the title compound (94 mg, 86%) is obtained as a white solid. Specific $[\alpha]^{25}_D=-22°$ (c 0.38, DMSO). Anal. Calcd for $C_{17}H_{21}N_3O_4$: C, 61.62; H, 6.39; N, 12.68. Found: C, 61.30; H, 6.68; N, 12.22.

Example 24

N-{[(5S)-3-(3-Glycoloyl-1,2,4,5-tetrahydro-1H-3-benzazepin-7-yl)-2-oxo-1,3-oxazolidin-5-yl]methyl}acetamide

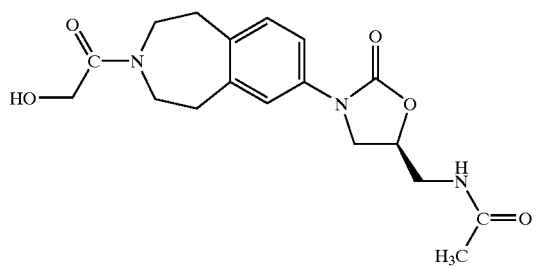

The product from Example 24 Step 1 (100 mg, 0.33 mmol) and triethyl amine (80 μL, 0.57 mmol in dichloromethane (5 mL) at 0° C. are treated with acetoxyacetyl chloride (50 μL, 0.41 mmol), stirred overnight at room temperature, and then concentrated in vacuo. The residue is dissolved in methanol (5 mL) and treated with potassium carbonate (100 mg, 0.7 mmol), stirred overnight at room temperature and then chromatographed on silica gel with 4% methanol in dichloromethane to give 100 mg (84%) of the title compound as a white solid. HRMS (FAB) calcd for $C_{18}H_{23}N_3O_5$+H1 362.1716, found 362.1725. Specific Rotation $[\alpha]^{25}_D$=-19° (c 0.53, DMSO).

Example 25

N-{[(5S)-3-(3-Acetyl-1,2,4,5-tetrahydro-1H-3-benzazepin-7-yl)-2-oxo-1,3-oxazolidin-5-yl]methyl}acetamide

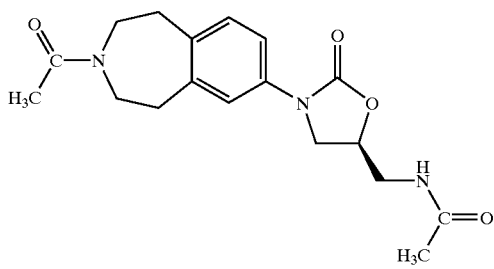

Using the material from Example 23 Step 1 (250 mg, 0.82 mmol) in dichloromethane (10 mL), triethyl amine (460 μL, 3.3 mmol) and acetic anhydride (160 μL, 1.7 mmol) are added and stirred overnight at room temperature, concentrated in vacuo and chromatographed on silica gel with 5% methnol in dichloromethane to give 250 mg (88%) of the title compound as a white solid. Specific Rotation $[\alpha]^{25}_D$=-23° (c 0.58, DMSO). Anal. Calcd for $C_{18}H_{23}N_3O_4$: C, 62.59; H, 6.71; N, 12.17. Found: C, 62.43; H, 6.87; N, 11.74.

Example 26

Methyl 7-{(5S)-5-[(acetylamino)methyl]-2-oxo-1,3-oxazolidin-3-yl}-1,2,4,5-tetrahydro-3H-3-benzazepine-3-carboxylate

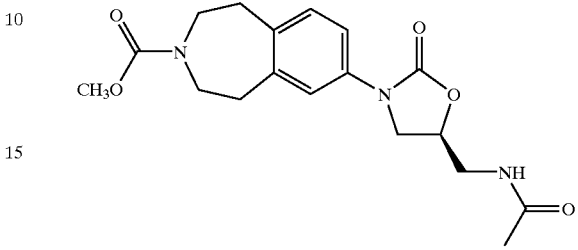

Following the procedure described in Example 25, using the material from Example 23 Step 1 (250 mg, 0.82 mmol) and methyl chloroformate (100 μL, 1.3 mmol) the title compound (183 mg, 61%) is obtained as a white solid. Specific Rotation $[\alpha]^{25}_D$=-21° (c 0.40, DMSO). Anal. Calcd for $C_{18}H_{23}N_3O_5$: C, 59.82; H, 6.41; N, 11.63. Found: C, 59.53; H, 6.53; N, 11.20.

Example 27

N-{[(5S)-3-(3-Benzoyl-1,2,4,5-tetrahydro-1H-3-benzazepin-7-yl)-2-oxo-1,3-oxazolidin-5-yl]methyl}acetamide

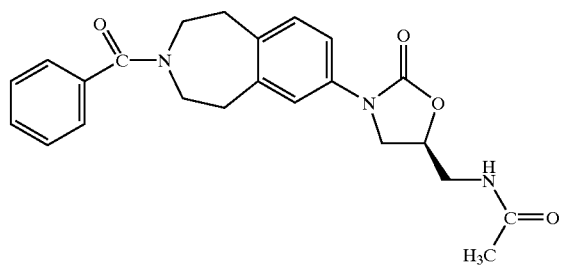

Following the procedure described in Example 25, using the material from Example 23 Step 1 (250 mg, 0.82 mmol) and benzoyl chloride (140 μL, 1.3 mmol) the title compound (277 mg, 82%) is obtained as a white solid. Specific Rotation $[\alpha]^{25}_D$=-17° (c 0.70, DMSO). Anal. Calcd for $C_{23}H_{25}N_3O_4$: C, 67.80; H, 6.18; N, 10.31.

Found: C, 67.53; H, 6.30; N, 10.01.

Example 28

N-({(5)-3-[3-(Methylsulfonyl)-1,2,4,5-tetrahydro-1H-3-benzazepin-7-yl]-2-oxo-1,3-oxazolidin-5-yl}methyl)acetamide

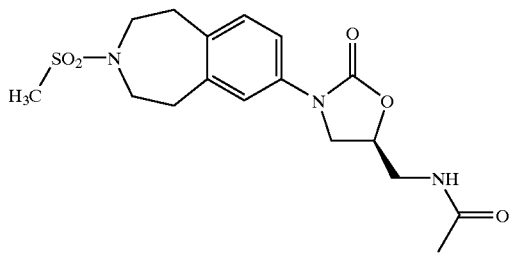

Following the procedure described in Example 25, using the material from Example 23 Step 1 (250 mg, 0.82 mmol) and methylsulfonyl chloride (130 μL, 1.3 mmol) the title compound (170 mg, 54%) is obtained as a white solid. Specific Rotation $[\alpha]^{25}_D = -18°$ (c 0.37, DMSO). Anal. Calcd for $C_{17}H_{23}N_3O_5S$: C, 53.53; H, 6.08; N, 11.02. Found: C, 52.98; H, 6.14; N, 10.53.

Example 29

Phenyl 7-{(5S)-5-[(acetylamino)methyl]-2-oxo-1,3-oxazolidin-3-yl}-1,2,4,5-tetrahydro-3H-3-benzazepine-3-carboxylate

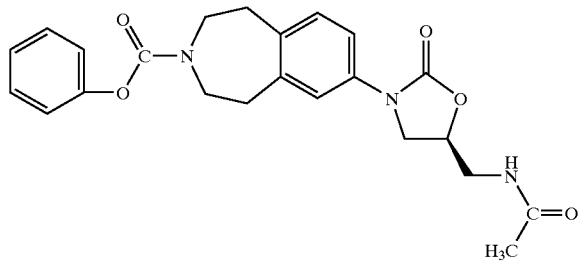

Following the procedure described in Example 25, using the material from Example 23 Step 1 (250 mg, 0.82 mmol) and benzene chloroformate (125 μL, 1.3 mmol) the title compound (192 mg, 55%) is obtained as a white solid. Specific Rotation $[\alpha]^{25}_D = -17$ (c 0.51, DMSO). Anal. Calcd for $C_{23}H_{25}N_3O_5$: C, 65.24; H, 5.95; N, 9.92. Found: C, 65.56; H, 6.14; N, 9.41.

Example 30

N-[((5S)-3-{3-(Phenyl)acetyl-1,2,4,5-tetrahydro-1H-3-benzazepin-7-yl}-2-oxo-1,3-oxazolidin-5-yl)methyl]acetamide

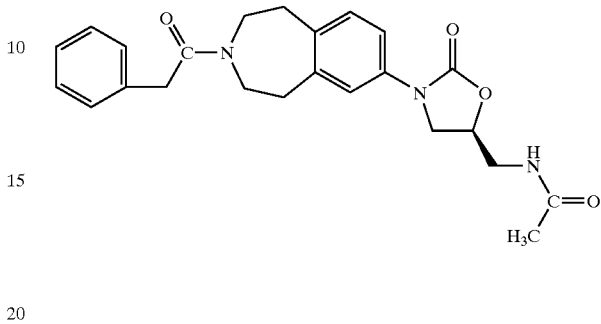

Following the procedure described in Example 25, using the material from Example 23 Step 1 (250 mg, 0.82 mmol) and phenylacetyl chloride (130 μL, 1.3 mmol) the title compound (165 mg, 48%) is obtained as a white solid. Specific Rotation (25 C D)=−17° (c 0.67, DMSO). Anal. Calcd for $C_{24}H_{27}N_3O_4$: C, 68.39; H, 6.46; N, 9.97. Found: C, 67.98; H, 6.57; N, 9.79

Example 31

N-[((5S)-3-{3-[(4-Iodophenyl)acetyl]-1,2,4,5-tetrahydro-1H-3-benzazepin-7-yl}-2-oxo-1,3-oxazolidin-5-yl)methyl]acetamide

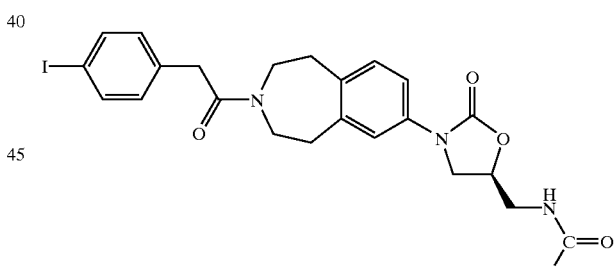

The product from Example 23 step 1 (250 mg, 0.82 mmol) is dissolved in pyridine (5 mL) and 4-iodo phenyl acetic acid(260 mg, 1.0 mmol), 1-(3-dimethylaminopropyl)-3-ethylcarbodiimide hydrochloride (235 mg, 1.2 mmol), and dimethylaminopyridine (10 mg) are added and stirred at room temperature overnight. The mixture is diluted with ethyl acetate, washed with water and brine, dried over anhydrous sodium sulfate, filtered, concentrated and chromatographed on silica gel with 5% methanol in dichloromethane to give 320 mg of the title compound (71%) as white solid. HRMS (FAB) calcd for $C_{24}H_{26}IN_3O_4$+H1 548.1048, found 548.1045. Specific Rotation $[\alpha]^{25}_D = -10°$ (c 0.53, DMSO).

Example 32

N-[((5S)-3-{3-[(3-Trifluoromethyl)phenyl)acetyl]-1,2,4,5-tetrahydro-1H-3-benzazepin-7-yl}-2-oxo-1,3-oxazolidin-5-yl)methyl]acetamide

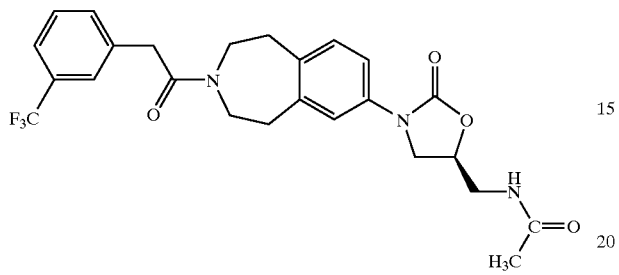

Following the procedure described in Example 31, using the material from Example 23 Step 1 (250 mg, 0.82 mmol) and 3-trifluoromethylphenyl acetic acid (200 mg, 1.0 mmol) the title compound (280 mg, 69%) is obtained as white solid. HRMS (FAB) calcd for $C_{25}H_{26}F_3N_3O_4$+H1 490.1953, found 490.1966. Specific Rotation $[\alpha]^{25}_D$=−13° (c 0.55, DMSO).

Example 33

N-[((5S)-3-{3-[(4-Trifluoromethyl)phenyl)acetyl]-1,2,4,5-tetrahydro-1H-3-benzazepin-7-yl}-2-oxo-1,3-oxazolidin-5-yl)methyl]acetamide

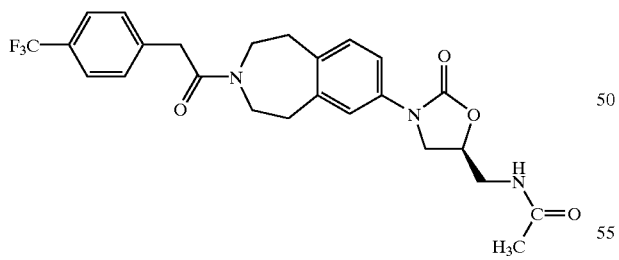

Following the procedure described in Example 31, using the material from Example 23 Step 1 (250 mg, 0.82 mmol) and 4-trifluoromethylphenyl acetic acid (200 mg, 1.0 mmol) the title compound (235 mg, 58%) is obtained as white solid. HRMS (FAB) calcd for $C_{25}H_{26}F_3N_3O_4$+H1 490.1953, found 490.1958. Specific Rotation $[\alpha]^{25}_D$=−13 (c 0.56, DMSO).

Example 34

N-({(5S)-2-Oxo-3-[3-(5-oxopentanoyl)-1,2,4,5-tetrahydro-1H-3-benzazepin-7-yl]-1,3-oxazolidin-5-yl}methyl)acetamide

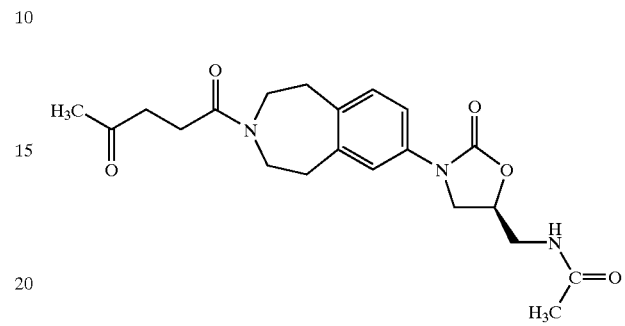

Following the procedure described in Example 31, using the material from Example 23 Step 1 (100 mg, 0.33 mmol) and levulonic acid (40 μL, 0.39 mmol) the title compound (75 mg, 57%) is obtained as white solid. HRMS (FAB) calcd for $C_{21}H_{27}N_3O_5$+H1 402.2029, found 402.2028.

Example 35

N-({(5S)-2-Oxo-3-[3-(5-oxohexanoyl)-1,2,4,5-tetrahydro-1H-3-benzazepin-7-yl]-1,3-oxazolidin-5-yl}methyl)acetamide

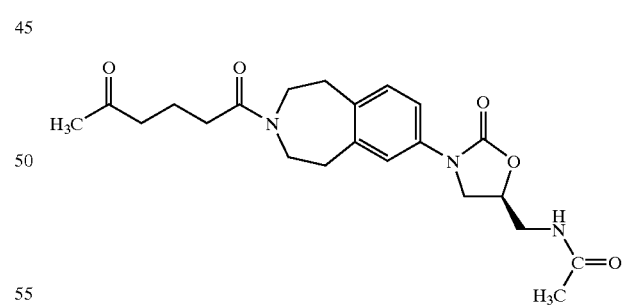

Following the procedure described in Example 31, using the material from Example 23 Step 1 (100 mg, 0.33 mmol) and acetylbutyric acid (50 μL, 0.39 mmol) the title compound (33 mg, 24%) is obtained as yellow solid. MS (FAB) m/z 416 (MH+), 417, 416, 415, 376, 332, 304, 113, 85, 56, 43. HRMS (FAB) calcd for $C_{22}H_{29}N_3O_5$+H1 416.2185, found 416.2187.

Example 36

N-{[(5S)-3-(2-Formyl-1,3,4,5-tetrahydro-1H-2-benzazepin-7-yl)-2-oxo-1,3-oxazolidin-5-yl]methyl}acetamide

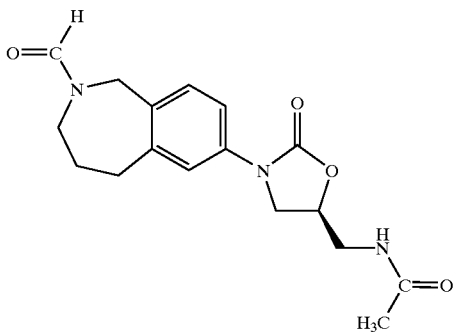

Step 1 Preparation of phenylmethyl 7-(phenylmethylcarboxyamino)-1,3,4,5-tetrahydro-1H-2-benzazepine-2-carboxylate To 6-aminotetralone (10.00 g, 62 mmol) in ethanol (12 ml) and water (6 mL) is added hydroxylamine hydrochloride (6.50 g, 93 mmol) and sodium acetate (7.65 mg, 93 mmol) and the mixture heated at 90° C. for 2 h. The ethanol is removed by distillation, water (60 mL) is added and the resulting solid collected by filtration and air dried. This solid is added to polyphosphoric acid (400 g) at 120–125° C. and stirred 1 h, then cooled and added to ice water (100 mL). The aqueous mixture is basified with concentrated ammonium hydroxide to pH 8–9, extracted with dichloromethane which is then dried over anhydrous sodium sulfate, filtered, and concentrated to a solid (5.6 g). The solid is dissolved in toluene (120 mL) and 2,5-hexandione (4.4 mL, 38 mmol) and p-toluenesulfonic acid (10 mg) are added and refluxed overnight using a Dean-Starke trap to remove water. The mixture is then cooled, filtered through a pad of silica gel, washing with ethyl acetate, and the combined organics concentrated in vacuo to give 8.1 g of a residue. This residue is dissolved in THF (100 mL) and added via cannula to lithium aluminum hydride (1.8 g, 47 mmol) in THF (50 mL), stirred at ambient temperature over night, then carefully quenched with water (1.8 mL), 2 N aqueous sodium hydroxide (1.8 mL), and water (5.4 mL). The resulting mixture is filtered through celite, washing with ethyl acetate, and the combined organics concentrated to a white solid. The solid is dissolved in ethanol (70 mL) and water (35 mL) and treated with hydroxylamine hydrochloride (21 g) and triethylamine (8.5 mL) and refluxed overnight, then cooled, basified with concentrated ammonium hydroxide, and extracted with dichloromethane. The organics are concentrated in vacuo and the residue dissolved in 2:1 acetone/water (150 mL), treated with benzylchloroformate (10.5 mL, 74 mmol) and sodium bicarbonate (25 g, 300 mmol) and stirred at room temperature overnight. The acetone is removed by rotary evaporation, the aqueous layer is extracted with dichloromethane, dried over anhydrous sodium sulfate, filtered, concentrated, and chromatographed on silica gel with 30% ethyl acetate in heptane to give 5.14 g (19%) of the title compound as white solid. MS (ESI+) m/z 431 (M+H). Anal. Calcd for $C_{26}H_{26}N_2O_4$: C, 72.54; H, 6.09; N, 6.51.

Found: C, 72.28; H, 6.34; N, 6.30.

Step 2 Preparation of phenylmethyl 7-{[(5S)-5-[(hydroxy)methyl]-2-oxo-3-oxazolidinyl]-(1,3,4,5-tetrahydro)-1H-2-benzazepine}carboxylate.

Following the procedure described in Example 20 Step 4, using the compound from the previous step as starting material the title compound (730 mg, 1.7 mmol) is obtained as a white solid. HRMS (FAB) calcd for $C_{22}H_{24}N_2O_5$+H1 397.1763, found 397.1774.

Step 3 Preparation of benzyl 7-{(5S)-5-[(acetylamino)methyl]-2-oxo-1,3-oxazolidin-3-yl}-1,3,4,5-tetrahydro-2H-2-benzazepine-2-carboxylate.

Following the procedure described in Example 25 Step 5, using the compound from the previous step as starting material the title compound is obtained as a white solid. Specific Rotation $[\alpha]^{25}_D$=−10° (c 0.66, methylene chloride). Anal. Calcd for $C_{24}H_{27}N_3O_5$: C, 65.89; H, 6.22; N, 9.60. Found: C, 65.37; H, 6.30; N, 9.47.

Step 4 Preparation of N-{[(5S)-3-(1,3,4,5-tetrahydro-1H-2-benzazepin-7-yl)-2-oxo-1,3-oxazolidin-5-yl]methyl}acetamide.

Following the procedure described in Example 20 Step 6, using the from the previous step as starting material (1.5 g, 3.5 mmol) the title compound is obtained as a white solid. MS (+ESI) m/z 304.1 (M+H).

Step 5 Preparation of N-{[(5S)-3-(2-formyl-1,3,4,5-tetrahydro-1H-2-benzazepin-7-yl)-2-oxo-1,3-oxazolidin-5-yl]methyl}acetamide Following the procedure described in Example 20 Step 7, using the compound from the previous step as starting material (500 mg, 1.65 mmol) the title compound is obtained as a white solid. HRMS (FAB) calcd for $C_{18}H_{23}N_3O_5$+H1 362.1716, found 362.1721. Anal. Calcd for $C_{17}H_{21}N_3O_4$: C, 61.62; H, 6.39; N, 12.68. Found: C, 61.31; H, 6.43; N, 12.43; Specific Rotation $[\alpha]^{25}_D$=−22° (c 0.70, DMSO).

Example 37

N-{[(5S)-3-(2-Glycoloyl-1,3,4,5-tetrahydro-1H-3-benzazepin-7-yl)-2-oxo-1,3-oxazolidin-5-yl]methyl}acetamide

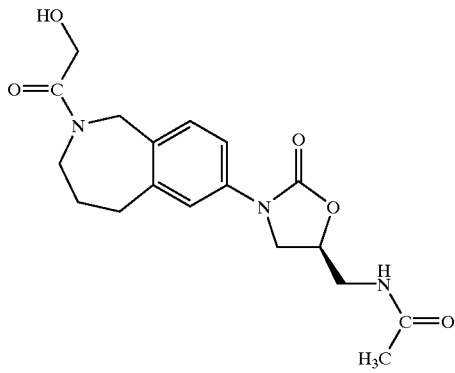

Following the procedure described in Example 24, using the compound from Example 36 Step 4 as starting material (80 mg, 0.26 mmol) the title compound is obtained as a white solid (75 mg, 79%). MS (ESI−) m/z 360 (M−H).

Example 38

N-{[(5S)-3-(2-Acetyl-1,3,4,5-tetrahydro-1H-2-benzazepin-7-yl)-2-oxo-1,3-oxazolidin-5-yl]methyl}acetamide

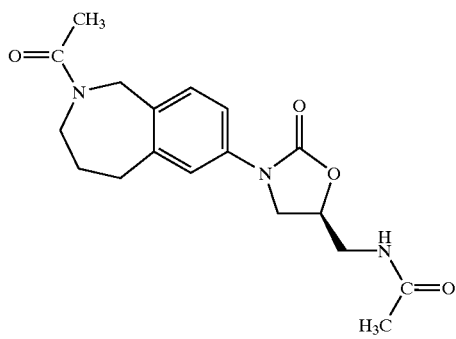

Following the procedure described in Example 25, using the compound from Example 36 Step 4 as starting material (250 mg, 0.82 mmol) the title compound is obtained as a white solid (235 mg, 82%). HRMS (FAB) calcd for $C_{18}H_{23}N_3O_4$+H1 346.1767, found 346.1777. Specific Rotation $[\alpha]^{25}_D$=-21° (c 0.53, DMSO).

Example 39

Methyl 7-{(5S)-5-[(acetylamino)methyl]-2-oxo-1,3-oxazolidin-3-yl}-1,3,4,5-tetrahydro-3H-2-benzazepine-2-carboxylate

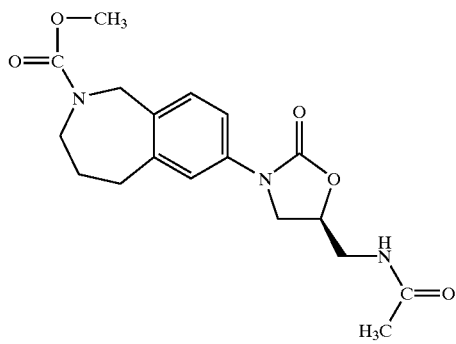

Following the procedure described in Example 26, using the compound from Example 36 Step 4 as starting material (250 mg, 0.82 mmol) the title compound is obtained as a white solid (155 mg, 52%). Specific Rotation $[\alpha]^{25}_D$=-19 (c 0.46, DMSO). Anal. Calcd for $C_{18}H_{23}N_3O_5$: C, 59.82; H, 6.41; N, 11.63. Found: C, 59.53; H, 6.62; N, 11.45.

Example 40

7-{(5S)-5-[(Acetylamino)methyl]-2-oxo-1,3-oxazolidin-3-yl}-N-phenyl-1,3,4,5-tetrahydro-2H-2-benzazepine-2-carboxamide

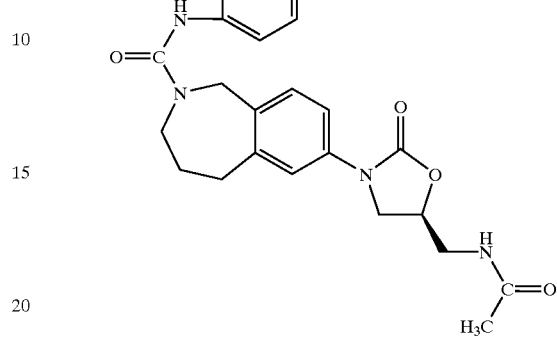

The compound from Example 36 Step 4 (100 mg, 0.33 mmol) in DMF (1 ml) is treated with phenylisocyanate (39 µL, 0.36 mmol), stirred over night at room temperature, absorbed on silica gel (5 g), and flush chromatographed eluting with 7% methanol in CH2Cl2 to give 135 mg (97%) of the title compound as a white solid. HRMS (FAB) calcd for $C_{23}H_{26}N_4O_4$+H1 423.2032, found 423.2038.

Example 41

N-{[(5S)-3-(3-Glycoloyl-1,2,4,5-tetrahydro-1H-3-benzazepin-7-yl)-2-oxo-1,3-oxazolidin-5-yl]methyl}ethanethioamide

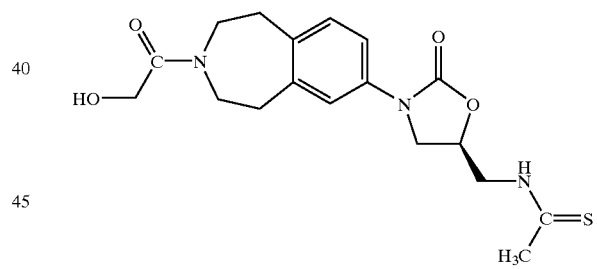

Step 1 Preparation of N-{[(5S)-3-(1,2,4,5-tetrahydro-1H-3-benzazepin-7-yl)-2-oxo-1,3-oxazolidin-5-yl]methyl}ethanethioamide The compound from Example 23 Step 1 (200 mg, 6.5 mmol) and Lawesson's Reagent (260 mg, 6.5 mmol) in dioxane (10 mL) is heated at reflux for 18 h under nitrogen, then cooled, diluted with ethyl acetate and washed with water and brine, dried, concentrated and chromatographed on silica gel eluting with 40% ethyl acetate in dichloromethane to give 120 mg (57%) of the title compound as a white solid. MS (ESI+) m/z 320.4 (M+H).

Step 2 Preparation of N-{[(5S)-3-(3-glycoloyl-1,2,4,5-tetrahydro-1H-3-benzazepin-7-yl)-2-oxo-1,3-oxazolidin-5-yl]methyl}ethanethioamide Following the procedure for Example 23 using the compound from the previous step the title compound is prepared as a white solid. HRMS (FAB) calcd for $C_{18}H_{23}N_3O_4S$+H1 378.1487, found 378.1489.

Example 42

N-({(5S)-3-[3-(5-Amino-1,3,4-thiadiazol-2-yl)-1,2,4,5-tetrahydro-1H-3-benzazepin-7-yl]-2-oxo-1,3-oxazolidin-5-yl}methyl)acetamide

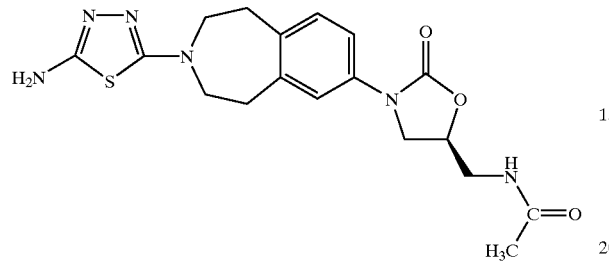

The compound from Example 22 Step 5 (500 mg, 1.6 mmol), 5-amino-2-bromo-1,3,4-thidiazole (320 mg, 1.8 mmol), and diisopropylethylamine (700 µL) in acetonitrile (20 mL) is heated at 60° C. for 3 days, cooled, concentrated in vacuo and chromatographed on silica gel eluting with 10% methanol in dichloromethane to give 507 mg (76%) as an amber solid. HRMS (FAB) calcd for $C_{18}H_{22}N_6O_3S+H^1$ 403.1552, found 403.1559. Specific Rotation $[\alpha]^{25}_D = -18°$ (c 0.88, DMSO).

Example 43

N-({(5S)-3-[3-(5-Methylthio-1,3,4-thiadiazol-2-yl)-1,2,4,5-tetrahydro-1H-3-benzazepin-7-yl]-2-oxo-1,3-oxazolidin-5-yl}methyl)acetamide

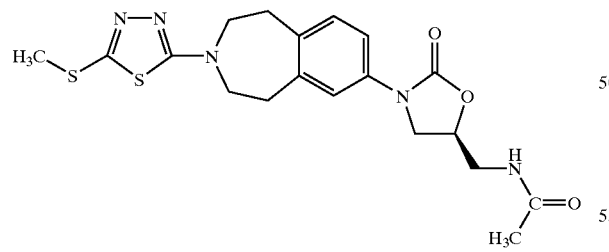

Following the procedure from Example 42 using the compound from Example 22 Step 5 (250 mg, 0.82 mmol) and 5-methylthio-2-bromo-1,3,4-thidiazole (190 mg, 0.90 mmol) the title compound (112 mg, 31%) is obtained as a white solid. HRMS (FAB) calcd for $C_{19}H_{23}N_5O_3S_2+H1$ 434.1320, found 434.1321. Specific Rotation $[\alpha]^{25}_D = -18°$ (c 0.49, DMSO).

Example 44

N-({(5S)-3-[3-(5-Methyl-1,3,4-thiadiazol-2-yl)-1,2,4,5-tetrahydro-1H-3-benzazepin-7-yl]-2-oxo-1,3-oxazolidin-5-yl}methyl)acetamide

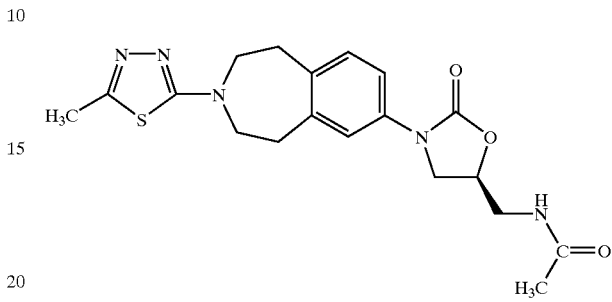

Following the procedure from Example 42 using the compound from Example 22 Step 5 (250 mg, 0.82 mmol) and 5-methyl-2-bromo-1,3,4-thidiazole (160 mg, 0.90 mmol) the title compound (49 mg, 15%) is obtained as a white solid. HRMS (FAB) calcd for $C_{19}H_{23}N_5O_3S+H1$ 402.1600, found 402.1607.

Example 45

N-[((5S)-3-{3-[5-(Formylamino)-1,3,4-thiadiazol-2-yl]-1,2,4,5-tetrahydro-1H-3-benzazepin-7-yl}-2-oxo-1,3-oxazolidin-5-yl)methyl]acetamide

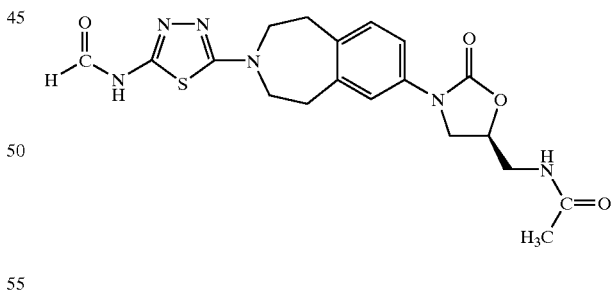

Following the procedure described in Example 20 Step 7 beginning with the product from Example 42 (150 mg, 0.37 mmol) the title compound is obtained as a white solid (105 mg, 66%). HRMS (FAB) calcd for $C_{19}H_{22}N_6O_4S+H^1$ 431.1501, found 431.1510.

Anal. Calcd for $C_{19}H_{22}N_6O_4S$: C, 53.01; H, 5.15; N, 19.52; S, 7.45. Found: C, 52.87; H, 5.30; N, 19.15.

Example 46

N-[5-(7-{(5S)-5-[(Acetylamino)methyl]-2-oxo-1,3-oxazolidin-3-yl}-1,2,4,5-tetrahydro-3H-3-benzazepin-3-yl)-1,3,4-thiadiazol-2-yl]-2-hydroxyacetamide

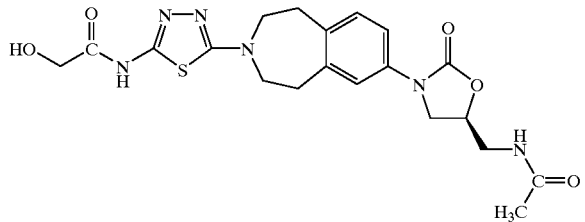

Following the procedure described in Example 24 beginning with the product from Example 42 (200 mg, 0.5 mmol) the title compound is obtained as a white solid (155 mg, 67%). Specific Rotation $[\alpha]^{25}_D = -16°$ (c 0.63, DMSO). Anal. Calcd for $C_{20}H_{24}N_6O_5S$: C, 52.16; H, 5.25; N, 18.25; S, 6.96. Found: C, 51.84; H, 5.49; N, 17.95.

Example 47

N-[[(5S)-2-Oxo-3-(1,2,4,5-tetrahydro-3-benzothiepin-7-yl)-5-oxazolidinyl]methyl]acetamide

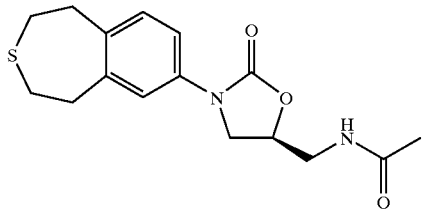

Step 1 Preparation of 4-nitro-1,2-benzenediacetic acid

To a stirred solution of 1,2-phenylenediacetic acid (10.2 g, 52.5 mmol) in conc. sulfuric acid (33 mL), cooled to −10° C., is added over 10 min a mixture of nitric acid (3.9 mL) and sulfuric acid (1.3 mL). After stirring at −10° C. for 4 h, the resulting mixture is poured onto ice (250 cc). The resulting mixture is extracted with ethyl acetate (3×300 mL). The combined organic phases are washed with H$_2$O (100 mL), dried (MgSO$_4$), filtered and concentrated to afford a white solid. The solid is recrystallized from methyl-tert-butyl ether in hexane to give 8.2 g (34.3 mmol, 65%) of the desired product. mp 187–188° C.

Step 2 Preparation of 4-nitro-1,2-benzenediethanol

To a stirred solution of the diacid (8.2 g, 34.3 mmol) (from step 1) in dry THF (140 mL), cooled to 0° C., is added dropwise over 30 min., a solution of 1 M borane-tetrahydrofuran complex (68.6 mL). The reaction mixture is stirred at 0° C. for 30 min., then at RT overnight. The reaction mixture is quenched with H$_2$O (63 mL) and then partitioned between ethyl acetate (60 mL) and H$_2$O (150 mL). The phases are separated. The aqueous layer is extracted with ethyl acetate (200 mL). The combined organic layers are washed with 1 N aqueous NaOH (200 mL), brine (200 mL) and dried (MgSO$_4$), filtered and concentrated to give 7.2 g (34.1 mmol, 99%) of the diol. mp 108–110° C.

Step 3 Preparation of (4-nitro-1,2-phenylene)di-2,1-ethanediyl dimethanesulfonate To a stirred suspension of the diol (from step 2) (7.2 g, 34.1 mmol) in CH$_2$Cl$_2$ (200 mL), cooled to 0° C., is added triethylamine (28.5 mL, 204.6 mmol) followed by methane sulfonyl chloride (7.9 mL, 102.3 mmol). The reaction mixture is stirred at RT for 2 h, then poured into H$_2$O (200 mL). The phases are separated. The aqueous phases was etracted with CH$_2$Cl$_2$ (200 mL). The combined organic phases were dried (MgSO$_4$), filtered and concentrated. The residue was dissolved in CH$_2$Cl$_2$, absorbed onto silica gel and is purified on a Biotage 40M (column with SIM using 60 5 ethyl acetate in hexane as the eluent to afford 8.76 g (23.7 mmol, 70%) of the desired bis-mesylate. mp 89–91° C.

Step 4 Preparation of phenylmethyl [3,4-bis[2-[(methylsulfonyl)oxy]ethyl]phenyl]carbamate To a stirred suspension of the nitro compound (from step 3) (7.74 g, 21.1 mmol) in 95% EtOH (110 mL) is added tin (II) chloride dihydrate (18.5 g, 82.1 mmol). The reaction mixture is heated at 70° C. for 1 h. The cooled reaction mixture is poured into ice (500 mL) and the pH is adjusted to 8 with 10% aqueous NaOH. A thick white precipitate formed. The reaction mixture is filtered through a plug of celite. The filter cake is washed with ethyl acetate (4×200 mL). The filtrate phases are separated. The aqueous phase is extracted with ethyl acetate (2×250 mL). The combined organic phases are dried (MgSO$_4$), filtered and concentrated to afford the desired aniline which is used immediately in the next reaction.

The above aniline is dissolved in THF (1.50 ml) and solid sodium bicarbonate (2.76 g 32.8 mmol) is added. The stirred reaction mixture is cooled to 0° C. and benzyl chloroformate (2.6 mL, 18.1 mmol) is added. The reaction mixture is stirred at RT overnight and then poured into CH$_2$Cl$_2$ (300 mL) and H$_2$O (150 mL). The phases are separated. The aqueous layer is extracted with CH$_2$Cl$_2$ (2×150 mL). The combined organic phases are dried (MgSO$_4$), filtered and concentrated. The residue is dissolved in CH$_2$Cl$_2$, absorbed onto silica gel and is purified on a Biotage 40M column with SIM using 40–60% ethyl acetate in hexane as the eluent to afford 5.25 g (11.2 mmol, 53%) of the desired product. mp 58–60° C.

Step 5 Preparation of phenylmethyl (1,2,4,5-tetrahydro-3-benzothiepin-7-yl)carbamate To a stirred solution of the bis mesylate (from step 4) (5.0 g, 10.6 mmol) in dry DMSO (72 mL) is added anhydrous sodium sulfide (2.48 g, 31.8 mmol). The reaction mixture is stirred at RT for 1 h. The reaction mixture is partitioned between H$_2$O (250 mL) and ethyl acetate (250 mL). The phases are separated, the aqueous phases is extracted with ethyl acetate (3×200 mL). The combined organic phases are dried (MgSO$_4$), filtered and concentrated. The residue is dissolved in CH$_2$Cl$_2$, absorbed onto silica gel and is purified on a Biotage 40M column with SIM using 10–20% ethyl acetate in hexane as the eluent to afford 2.37 g (7.6 mmol, 71%) of the desired product as a white solid. mp 118–120° C.

Step 6 Preparation of N-[[(SS)-2-oxo-3-(1,2,4,5-tetrahydro-3-benzothiepin-7-yl)-5-oxazolidinyl]methyl]acetamide To a stirred solution of the carbamate, from step 5, (646.s mg, 2.1 mmol) in DMF (1.3 mL) is added methanol (0.17 mL, 4.13 mmol). The reaction mixture is cooled to 15° C. and a solution of 1 M lithium t-butoxide in hexane is added (6.2 mL, 6.18 mmol) over 1 h. The reaction mixture is cooled to 0° C. and the chloroacetate (797.6 mg, 4.12 mmol) is added in one portion. The reaction mixture is stirred at RT overnight. The reaction mixture is treated with saturated aqueous NH$_4$Cl. The reaction mixture is poured into CH$_2$Cl$_2$ (60 mL) and H$_2$O (30 mL). The phases were separated. The aqueous phases are extracted with CH$_2$Cl$_2$ (2×20 mL). The combined organic phases are dried (MgSO$_4$), filtered and concentrated. The residue is dissolved in CH2Cl2, absorbed onto silica gel and purified on a Biotage 40S column with SIM using 15–100% ethyl acetate in hexane as the eluent to afford 488.8 mg (1.53 mmol, 74%) of the desired product. mp 178–180° C.

Example 48

N-[[(5S)-2-Oxo-3-(1,2,4,5-tetrahydro-3,3-dioxido-3-benzothiepin-7-yl)-5-oxazolidinyl]methyl]acetamide

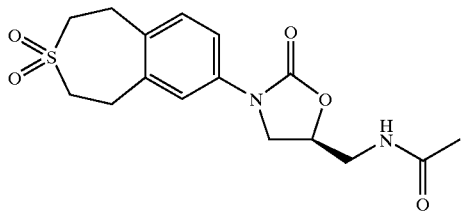

To a stirred solution of the sulfide, (from step 6 of example 47) (223.2 mg, 0.70 mmol) in 25% H$_2$O/acetone (10 mL) is added N-methyl-morpholine-N-oxide (245.0 mg, 2.10 mmol) followed by a solution of 2.5% osmium tetroxide in t-butanol (39 μL, 0.11 mmol). The reaction mixture is stirred at RT overnight, then treated with 10% aqueous NaHSO$_4$. The reaction mixture is poured into CH$_2$Cl$_2$ (20 mL) and the phases are separated. The aqueous phase is extracted with CH$_2$Cl$_2$ (2×20 mL). The combined organic phases are dried (MgSO$_4$), filtered and concentrated. The residue is dissolved in CH$_3$OH/CH$_2$Cl$_2$, absorbed onto silica gel and is purified on a Biotage 40S column with a SIM using 5% CH$_3$OH in CH$_2$Cl$_2$ as the eluent to afford 201.6 mg, (0.57 mmol, 82%) of the desired product. mp 142–144° C.

Example 49

N-[[(5S)-2-Oxo-3-(1,2,4,5-tetrahydro-3-benzothiepin-7-yl)-5-oxazolidinyl]methyl]ethanethioamide

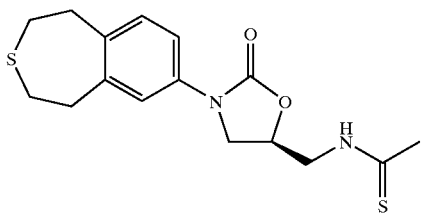

Step 1 Preparation of 1,1-dimethyl [[(SS)-2-oxo-3-(1,2,4,5-tetrahydro-3-benzothiepin-7-yl)-5-oxazolidinyl]methyl]carbamate To a stirred solution of phenylmethyl (1,2,4,5-tetrahydro-3-benzothiepin-7-yl)carbamate (from example 47, step 5) (662.9 mg, 2.1 mmol) in dry DMF (1.4 mL) is added 1,1-dimethylethyl[(2S)-3-chloro-2-hydroxypropyl]carbamate (557.8 mg, 2.7 mmol). The resulting mixture is cooled to 0° C. and a solution of 1 M lithium t-butoxide in THF (5.1 mL, 5.1 mmol) is added dropwise over 20 min. The reaction mixture is stirred at RT for 18 h, then treated with saturated NH$_4$Cl (10 mL). The reaction mixture is poured into CH$_2$Cl$_2$ (40 mL) and the phases are separated. The aqueous layer is extracted with CH$_2$Cl$_2$ (2×20 mL). The combined organic phases are washed with brine (20 mL), dried (MgSO$_4$), filtered and concentrated. The resulting residue is dissolved in CH$_2$Cl$_2$, absorbed onto silica gel and is purified on a Biotage 40S column with SIM using 10–35% ethyl acetate in hexane as the eluent to afford 664.7 mg (1.76 mmol, 83%) of the desired product as a white solid. mp 118–120° C.

Step 2 Preparation of N-[[(SS)-2-oxo-3-(1,2,4,5-tetrahydro-3-benzothiepin-7-yl)-5-oxazolidinyl]methyl]ethanethioamide To a stirred solution of the above Boc protected compound (152.8 mg, 0.4 mmol) in CH$_3$OH (3 mL) is added 4M HCl in dioxane (3 mL). The reaction mixture is stirred at RT for 90 min, then concentrated. The white solid is suspended in CH$_3$OH (10 mL) and triethylamine (0.14 mL, 1.0 mmol) is added, To this stirred solution is added ethyl dithioacetate (55 μL, 0.48 mmol). The reaction mixture is heated at reflux for 1 h. The cooled reaction mixture is concentrated. The resulting residue is dissolved in CH$_2$Cl$_2$/CH$_3$OH, absorbed onto silica gel and is purified on a Biotage 12M column with a Sim using 2% CH$_3$OH in CH$_2$Cl$_2$ as the eluent to afford 113.0 mg (0.33 mmol, 84%) of the desired sulfide thioamide, as a white solid. mp 146–147° C.

Example 50

N-[[(5S)-2-Oxo-3-(1,2,4,5-tetrahydro-3,3-dioxido-3-benzothiepin-7-yl)-5-oxazolidinyl]methyl]ethanethioamide

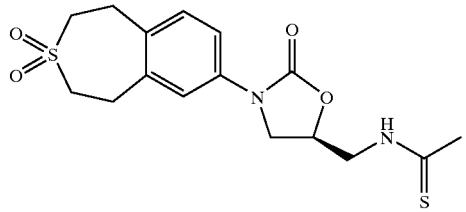

Step 1 Preparation of 1,1-dimethyl [[(SS)-2-oxo-3-(1,2,4,5-tetrahydro-3,3-dioxido-3-benzothiepin-7-yl)-5-oxazolidinyl]methyl]carbamate To a stirred solution of the Boc protected compound (132.2 mg, 0.35 mmol) (from step 1 of example 49) in 25% H$_2$O /acetone (5 mL) is added N-methylmorpholine-N-oxide (122.8 mg, 1.05 mmol) followed by 2.5% osmium tetroxide in t-butanol (16.5 μL, 0.05 mmol). The reaction mixture is stirred at RT for 18 h then treated with 10% aqueous NaHSO$_4$. The reaction mixture is poured into CH$_2$Cl$_2$ (40 mL). The phases are separated. The aqueous layer is extracted with CH$_2$Cl$_2$ (20 mL). The combined organic phases are dried (MgSO$_4$), filtered and concentrated. The residue is dissolved in CH$_2$Cl$_2$, absorbed onto silica gel and is purified on a Biotage 12M column with a SIM using 2% CH$_3$OH in CH$_2$Cl$_2$ as the eluent to afford 130.4 mg, (0.32 mmol, 91%) of desired sulfone.

Step 2 Preparation of N-[[(SS)-2-oxo-3-(1,2,4,5-tetrahydro-3,3-dioxido-3-benzothiepin-7-yl)-5-oxazolidinyl]methyl]ethanethioamid The above compound (99.9 mg, 0.24 mmol) in CH$_3$OH (1 mL) is added 4M HCl in dioxane (2 mL). The reaction mixture is stirred at RT for 2 h, then concentrated. The residue is dissolved in CH$_3$OH (2 mL) and triethylamine (84 μL, 0.60 mmol) is added followed by ethyl dithioacetate (34 μL, 0.29 mmol). The reaction mixture is heated at reflux for 1 h, cooled and is concentrated. The residues is dissolved in CH$_2$Cl$_2$, absorbed onto silica gel and is purified on a Biotage 12M column with a SIM using 2% CH$_3$OH in CH$_2$Cl$_2$ as the eluent to afford 64.1 mg (0.17 mmol, 73%) of the desired sulfone. mp 134–136° C.

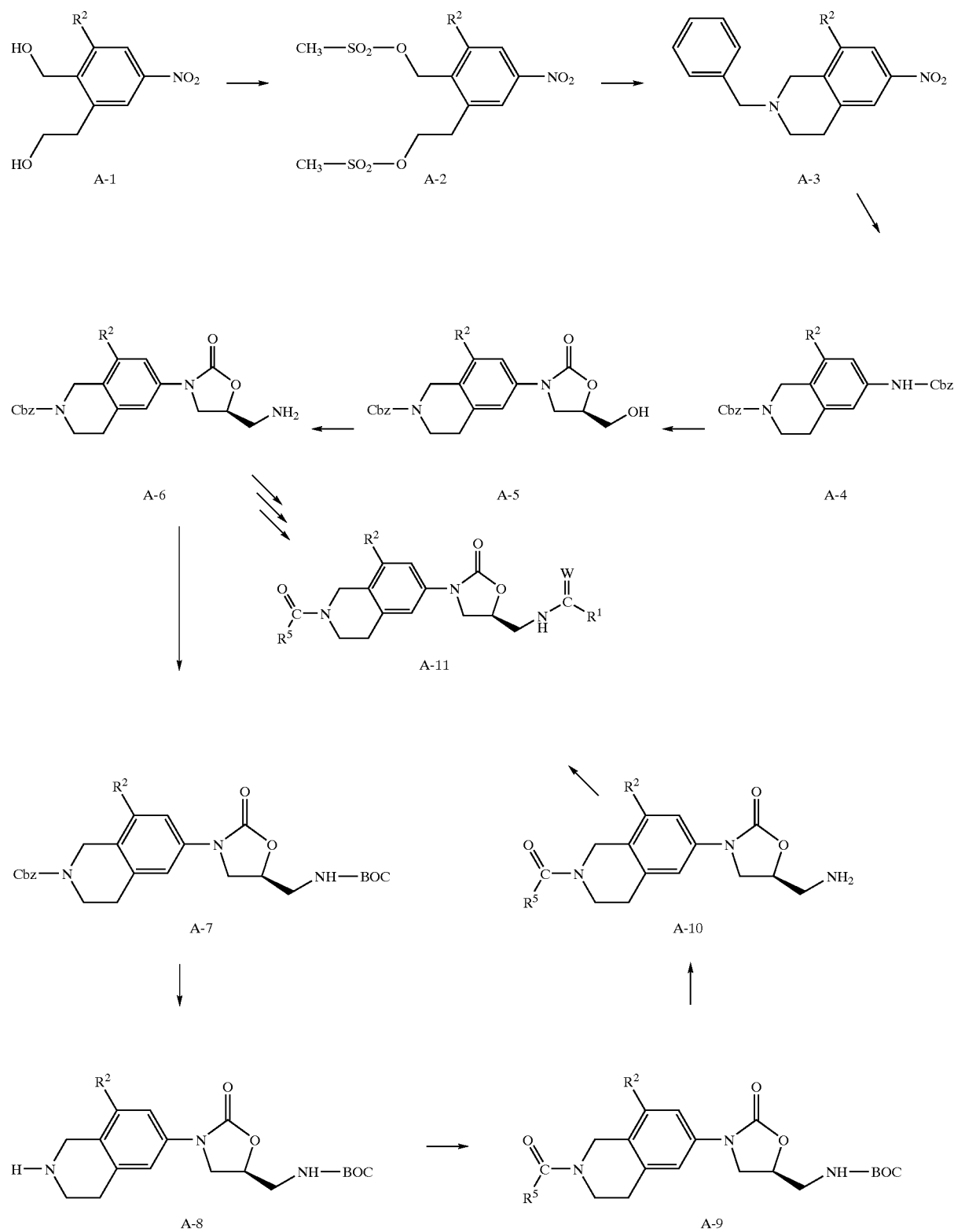
Scheme A

Scheme B
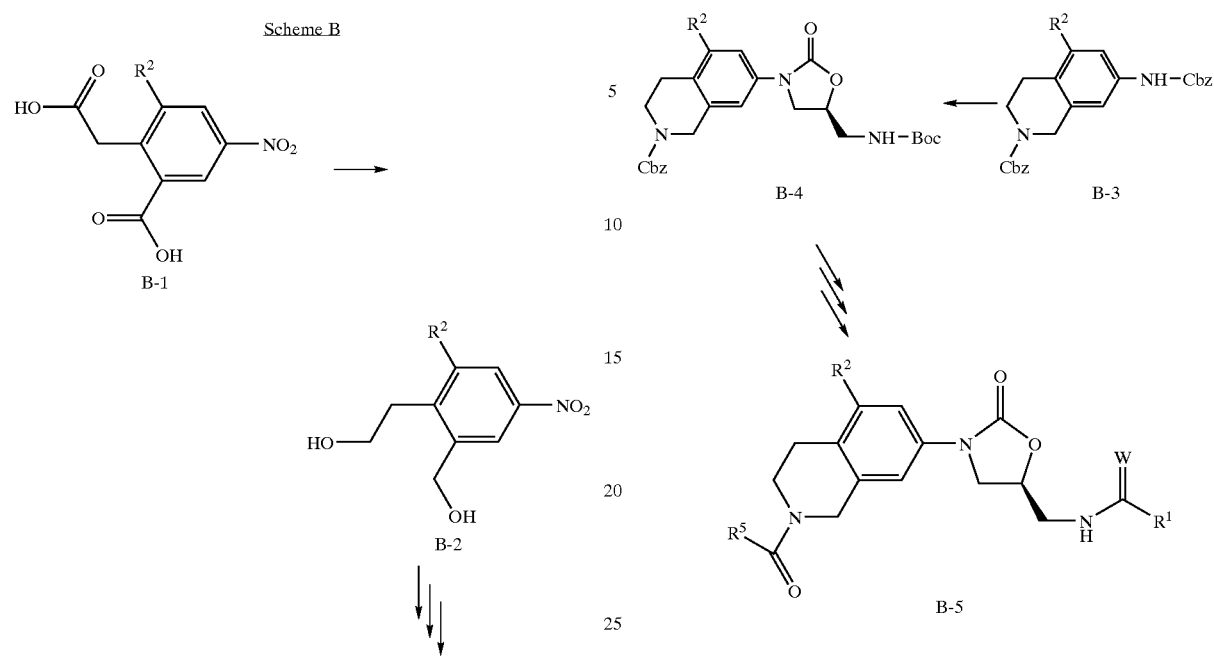
Scheme C
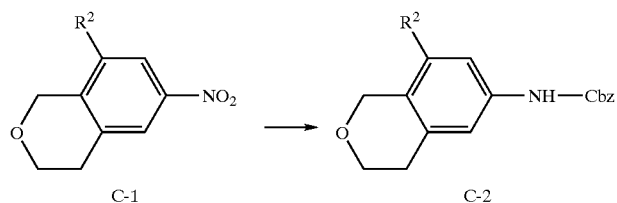
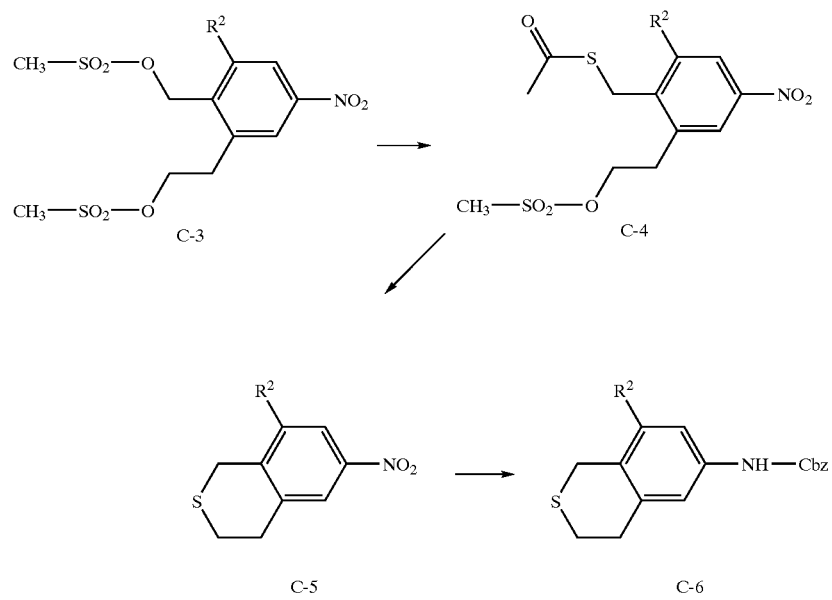

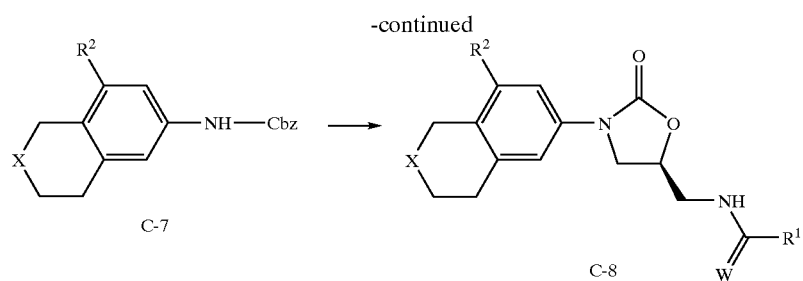
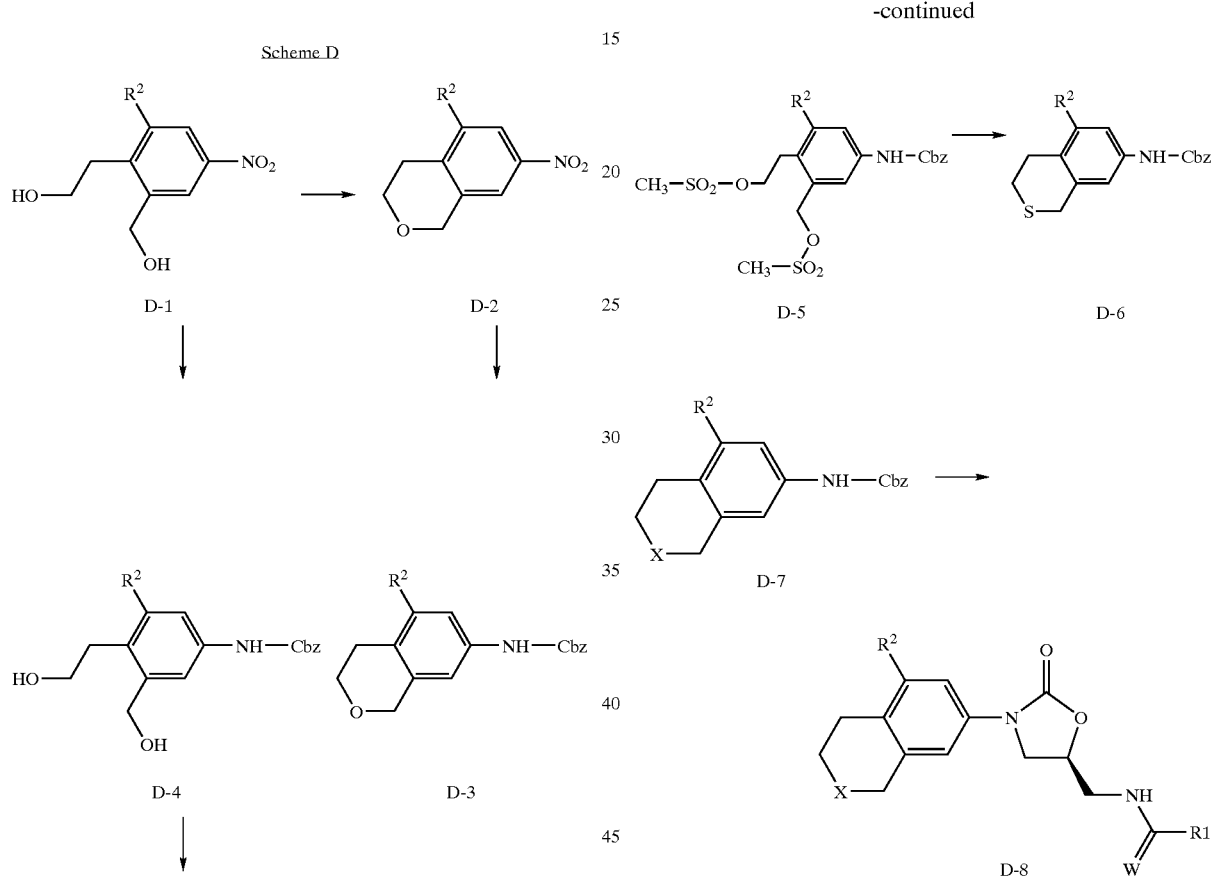
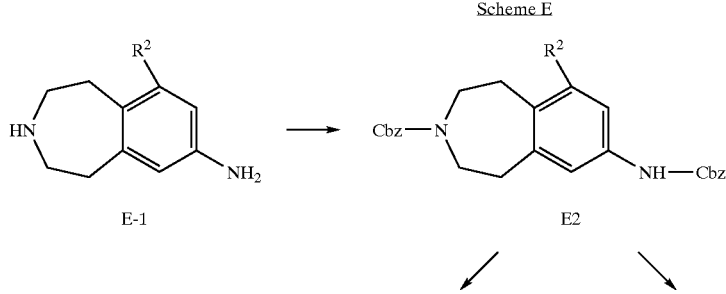

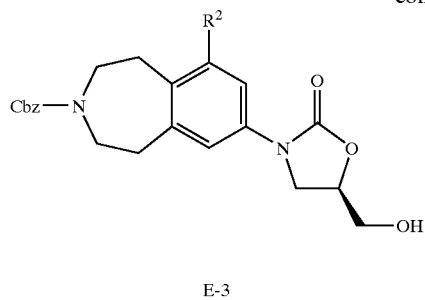
E-3
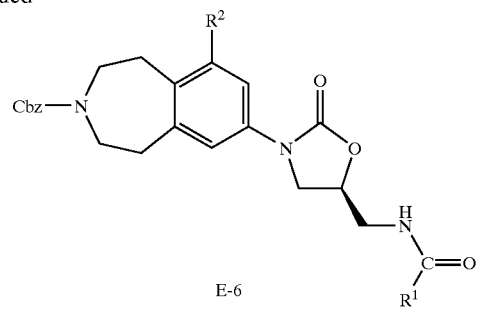
E-6
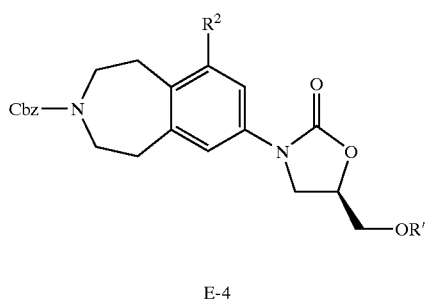
E-4
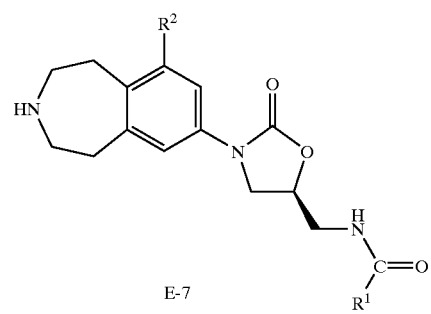
E-7
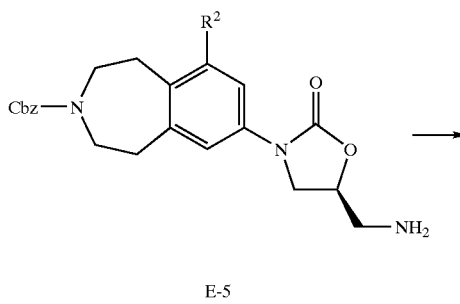
E-5
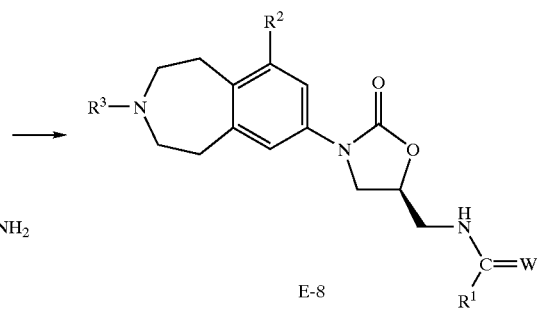
E-8
Scheme F
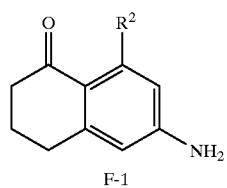
F-1
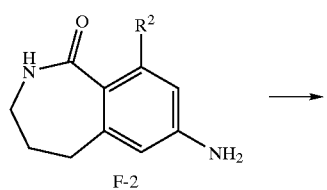
F-2
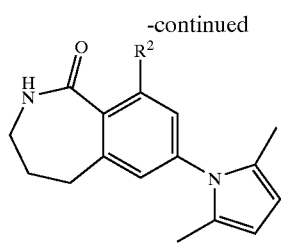
F-3
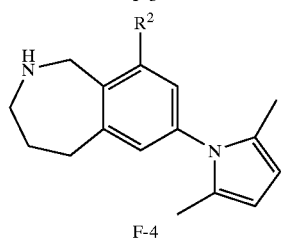
F-4

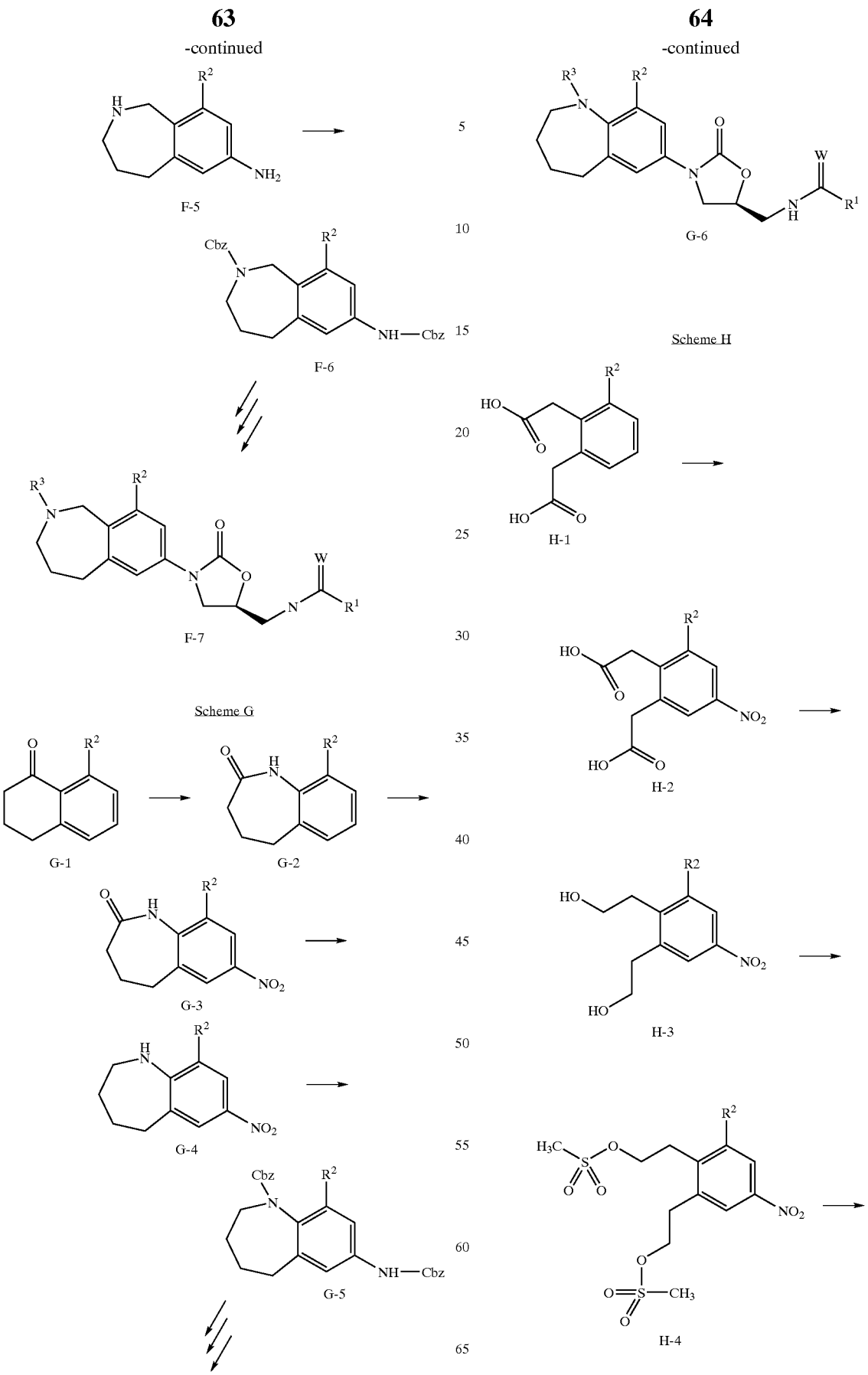

-continued
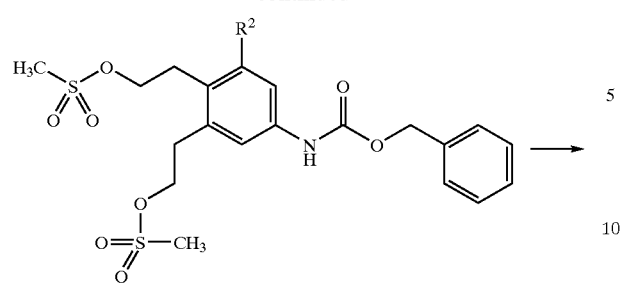
H-5
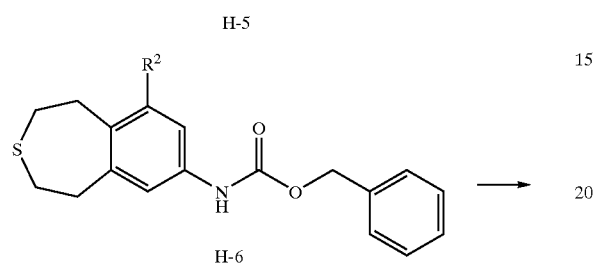
H-6
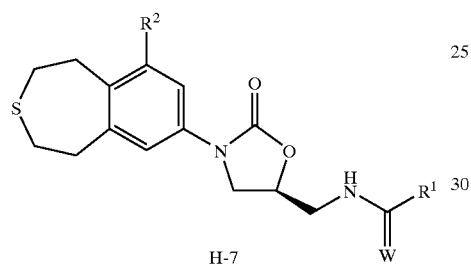
H-7
Scheme I
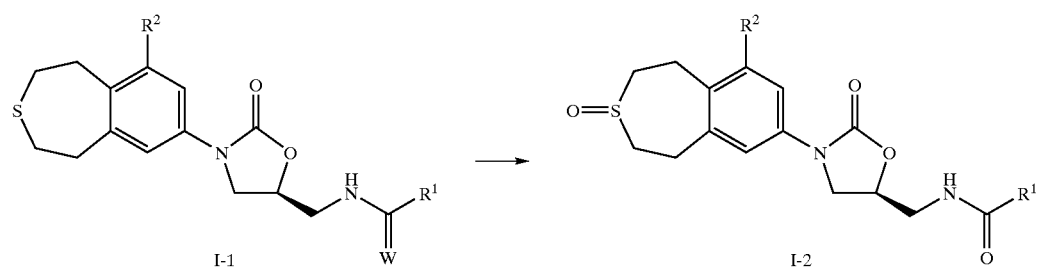
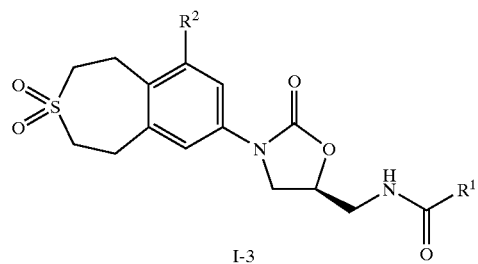
I-3

Scheme J
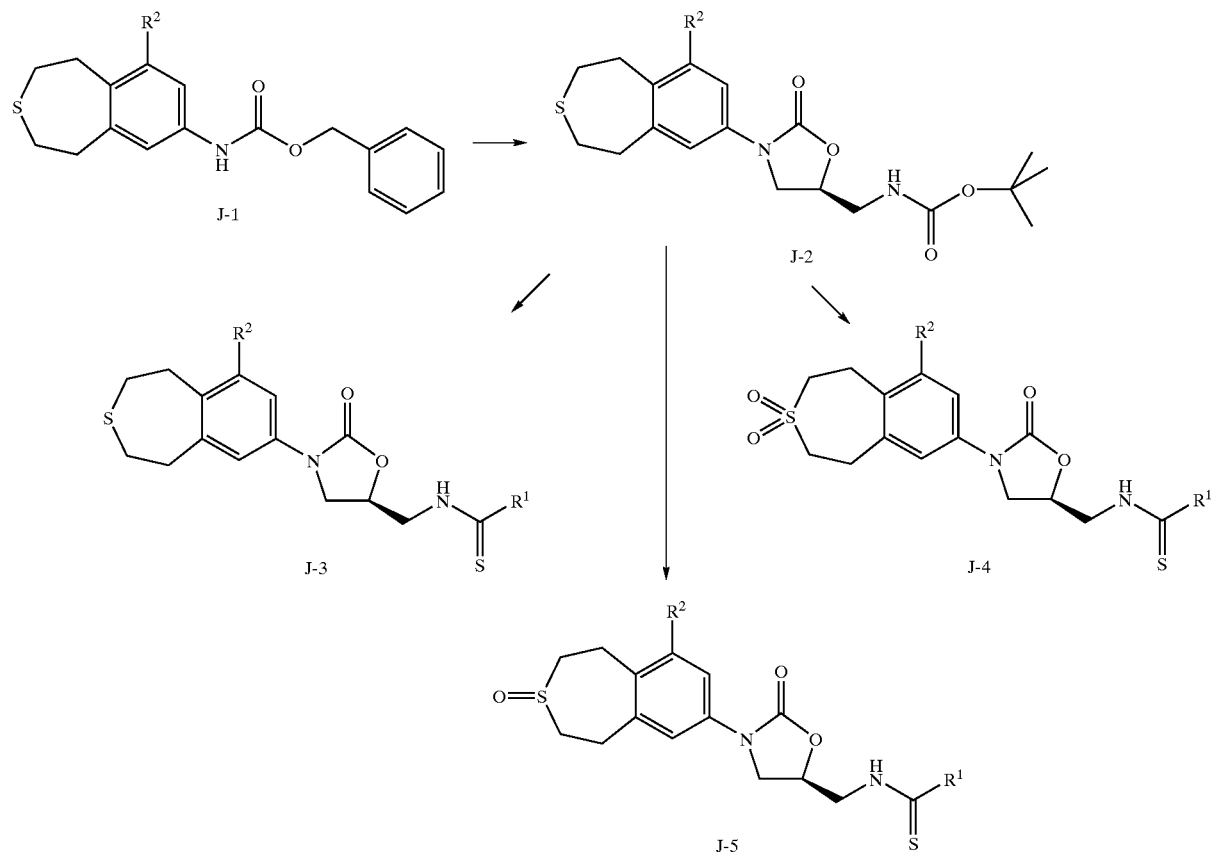
Scheme K
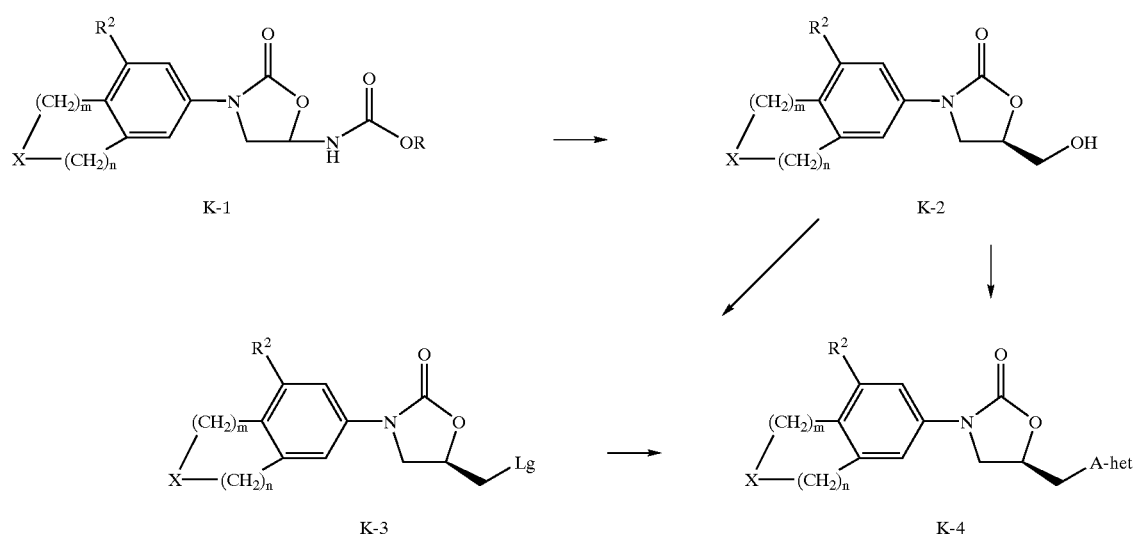

Scheme L

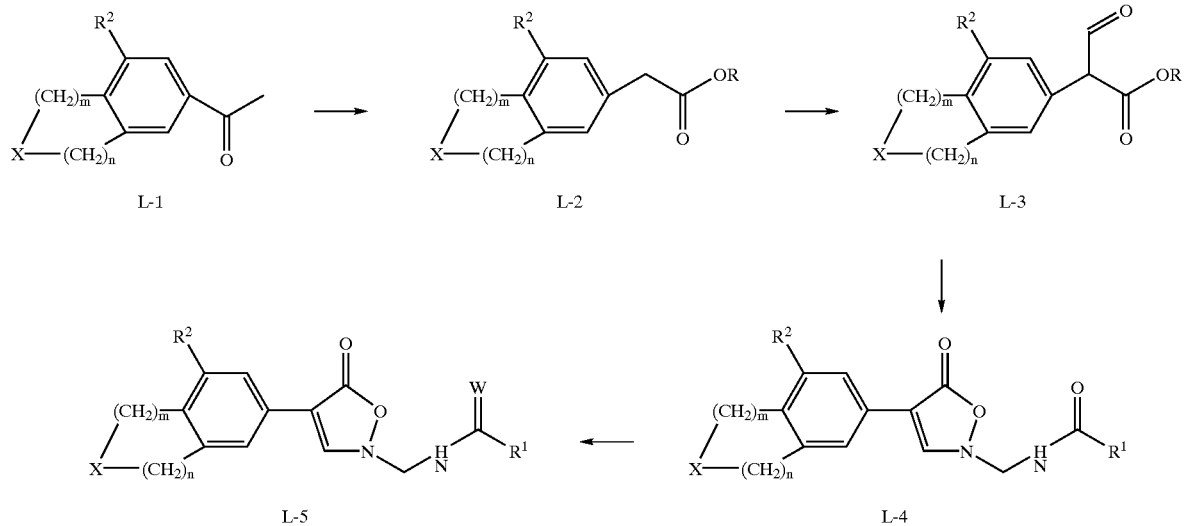

We claim:
1. A compound of formula I

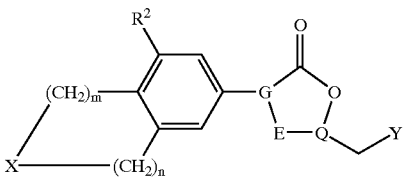

or a pharmaceutically acceptable salt thereof wherein
Y is
  a) —NHC(=W)R$^1$;
  b) —O-het, —S-het, or —NH-het;
X is —NR$^3$—,
W is
  a) O, or
  b) S;
R$^1$ is
  a) H,
  b) C$_{1-8}$alkyl,
  c) C$_{3-6}$cycloalkyl,
  d) OC$_{1-4}$alkyl
  e) SC$_{1-4}$alkyl,
  f) NH$_2$,
  g) NHC$_{1-6}$alkyl, or
  h) N(C$_{1-6}$alkyl)$_2$;
R$^2$ is
  a) H,
  b) halo, or
  c) C$_{1-4}$alkyl;
R$^3$ is
  a) H,
  b) C$_{1-8}$alkyl,
  c) aryl,
  d) C(=W)R$^5$,
  e) C(=O)OR$^6$, or
  f) S(=O)$_i$R$^7$;
R$^4$ is
  a) H, or
  b) C$_{1-8}$alkyl;

R$^5$ is
  a) H,
  b) aryl,
  c) NR$^8$R$^9$, or
  d) C$_{1-8}$alkyl;
R$^6$ is
  a) C$_{1-8}$alkyl,
  b) aryl, or
R$^7$ is
  a) aryl,
  b) NR$^8$R$^9$, or
  c) C$_{1-8}$alkyl;
R$^8$ and R$^9$ are independently
  a) H,
  b) C$_{1-8}$alkyl, or
  c) aryl;
wherein >G-E- is >N—C— and Q is a carbon atom;
aryl is a phenyl radical or an ortho-fused bicyclic carbocyclic radical wherein at least one ring is aromatic;
het is a C-linked five- (5) or six- (6) membered saturated or unsaturated heterocyclic ring having 1, 2, or 3 heteroatoms selected from the group consisting of oxygen, sulfur, and nitrogen, which is optionally fused to a benzene ring;
at each occurrence, alkyl or cycloalkyl is optionally substituted with one or more OR$^8$, halo, aryl, S(=O)$_i$R$^7$, C(=W)R$^8$, OC(=O)C$_{1-6}$alkyl, or NR$^8$R$^9$;
at each occurrence, aryl is optionally substituted with one or more halo, OH, CF$_3$, OC$_{1-6}$alkyl, CN, C$_{1-6}$ alkyl, S(=O)$_i$R$^7$, C(=W)R$^8$, OC(=O)R$^8$, NHC(=O)R$^8$, or NR$^8$R$^9$;
at each occurrence, het is optionally substituted with one or more halo, OH, CF$_3$, OC$_{1-6}$alkyl, CN, C$_{1-6}$ alkyl, S(=O)$_i$R$^7$, C(=W)R$^8$, OC(=O)R$^8$, NHC(=O)R$^8$, or NR$^8$R$^9$, oxo, or oxime;
m is 2;
n is 2; and
i is 0, 1, or 2.

2. A compound of claim 1 which is a compound of formula IA:

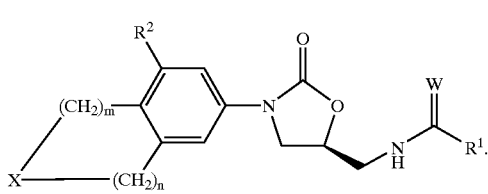

IA

3. A compound of claim 2 wherein $R^2$ is H.
4. A compound of claim 2 wherein $R^1$ is $C_{1-6}$alkyl.
5. A compound of claim 2 wherein $R^1$ is methyl.
6. A compound of claim 4 wherein X is $NR^3$.
7. A compound of claim 4 wherein $R^3$ is $C(=O)R^5$, or $C(=O)OR^5$.
8. A compound of claim 6 wherein $R^3$ is $C(=O)CH_2OH$.
9. A compound of claim 6 wherein $R^3$ is CHO.
10. A compound of claim 7 wherein $R^5$ is $C_{1-4}$alkyl, optionally substituted with $C(=O)C_{1-4}$alkyl, $OC(=O)C_{1-4}$alkyl, $C(=O)$phenyl, or phenyl, wherein said phenyl is optionally substituted with I, or $CF_3$.
11. A compound of claim 7 wherein $R^5$ is phenyl.
12. A compound of claim 6 wherein $R^3$ is $C(=S)R^5$, wherein $R^5$ is alkyl, alkyl or $NR^8R^9$, wherein $R^8$ and $R^9$ are independently H, $C_{1-4}$alkyl or aryl.
13. A compound of claim 6 wherein $R^3$ is $S(=O)_iC_{1-4}$alkyl.
14. A compound of claim 6 wherein $R^3$ is H, $C_{1-8}$alkyl, or aryl.

15. A compound of claim 1 which is a compound of formula IB:

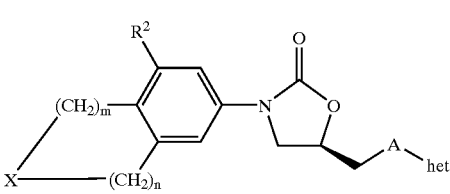

IB wherein A is O, S or NH and het is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

16. A method for treating microbial infections comprising: administering to a mammal in need thereof an effective amount of a compound of claim 1.
17. The method of claim 16 wherein said compound is administered orally, parenterally, transdermally, or topically.
18. The method of claim 16 wherein said compound is administered in an amount of from about 0.1 to about 150 mg/kg of body weight/day.
19. The method of claim 16 wherein said compound is administered in an amount of from about 3 to about 100 mg/kg of body weight/day.
20. The method of claim 16 wherein said infection is skin infection.
21. The method of claim 16 wherein the infection is eye infection.

* * * * *